United States Patent
Johnston et al.

(10) Patent No.: US 12,082,847 B2
(45) Date of Patent: Sep. 10, 2024

(54) IMPLANT FOR BONE FRACTURE STABILIZATION

(71) Applicant: University of Saskatchewan, Saskatoon (CA)

(72) Inventors: Geoffrey H. F. Johnston, Saskatoon (CA); Nima Ashjaee, Saskatoon (CA); James Duncan Johnston, Saskatoon (CA)

(*) Notice: Subject to any disclaimer, the term of this patent is extended or adjusted under 35 U.S.C. 154(b) by 787 days.

(21) Appl. No.: 17/268,892

(22) PCT Filed: Aug. 15, 2019

(86) PCT No.: PCT/CA2019/051113
§ 371 (c)(1),
(2) Date: Feb. 16, 2021

(87) PCT Pub. No.: WO2020/037397
PCT Pub. Date: Feb. 27, 2020

(65) Prior Publication Data
US 2021/0177465 A1    Jun. 17, 2021

Related U.S. Application Data

(60) Provisional application No. 62/719,646, filed on Aug. 18, 2018.

(51) Int. Cl.
*A61B 17/68* (2006.01)
*A61F 2/28* (2006.01)

(52) U.S. Cl.
CPC ............... *A61B 17/68* (2013.01); *A61F 2/28* (2013.01)

(58) Field of Classification Search
CPC ...... A61F 2002/2835; A61F 2002/2825; A61F 2002/2846; A61F 2002/2892;
(Continued)

(56) References Cited

U.S. PATENT DOCUMENTS

| | | | | |
|---|---|---|---|---|
| 2,998,007 A | * | 8/1961 | Herzog | A61B 17/7266 606/63 |
| 4,055,172 A | * | 10/1977 | Ender | A61B 17/7208 606/62 |

(Continued)

FOREIGN PATENT DOCUMENTS

| CA | 2868087 A1 | 9/2014 |
|---|---|---|
| CA | 2870017 A1 | 10/2014 |
| JP | 2003335574 A | 11/2003 |

OTHER PUBLICATIONS

Tanzer et al., "Enhancement of bone growth into porous intramedullary implants using non-invasive low intensity ultrasound". Journal of Orthopaedics Research 19 (2001) 195-199.

(Continued)

*Primary Examiner* — Jessica Weiss
(74) *Attorney, Agent, or Firm* — Viridant IP

(57) ABSTRACT

Implants and methods for stabilizing bone fractures are provided. In one embodiment, the implants are spheres. In another embodiment, the implants are rods. The rods can be used to stabilize peripheral portions of a bone fracture. The rods can be shaped and configured to correspond to the shape of a region of bone against which the rod will be deployed. The rods can be provided with surface features for engaging adjacent rods and/or adjacent regions of bone to further stabilize the rods. The spheres can be inserted to fill a remaining volume of the fracture cavity. The implants can be made from orthobiologic materials.

20 Claims, 33 Drawing Sheets

(58) Field of Classification Search
CPC ...... A61F 2002/2896; A61F 2002/2871; A61F 2/28; A61B 17/68
USPC ........................................................ 606/331
See application file for complete search history.

(56) References Cited

U.S. PATENT DOCUMENTS

| | | | |
|---|---|---|---|
| 4,429,691 | A | 2/1984 | Niwa et al. |
| 5,084,050 | A | 1/1992 | Draenert |
| 6,709,462 | B2 | 3/2004 | Hanssen |
| 7,044,968 | B1 | 5/2006 | Yaccarino, III et al. |
| 7,621,912 | B2 | 11/2009 | Harms et al. |
| 8,153,148 | B2 | 4/2012 | Maspero et al. |
| 9,247,972 | B2 | 2/2016 | Longepied |
| 2001/0018614 | A1 | 8/2001 | Bianchi |
| 2001/0018615 | A1 | 8/2001 | Biegun et al. |
| 2002/0147499 | A1 | 10/2002 | Shea et al. |
| 2002/0151978 | A1* | 10/2002 | Zacouto ................. A61F 2/3609 606/301 |
| 2004/0186576 | A1* | 9/2004 | Biscup ................... A61F 2/442 623/17.14 |
| 2007/0093912 | A1* | 4/2007 | Borden ................... A61L 27/48 606/76 |
| 2008/0183177 | A1* | 7/2008 | Fox ..................... A61B 17/1764 623/20.14 |
| 2010/0087821 | A1 | 4/2010 | Trip et al. |
| 2011/0144764 | A1 | 6/2011 | Bagga et al. |
| 2012/0116515 | A1* | 5/2012 | Semler ...................... A61F 2/28 623/23.63 |
| 2012/0265167 | A1 | 10/2012 | Simonson et al. |
| 2013/0165540 | A1 | 6/2013 | Delaney et al. |
| 2013/0178947 | A1 | 7/2013 | Monaghan et al. |
| 2013/0218288 | A1 | 8/2013 | Fonte et al. |
| 2017/0020673 | A1* | 1/2017 | Colclough ........ A61M 37/0069 |

OTHER PUBLICATIONS

He et al., "Fabrication of Beta-tricalcium phosphate composite ceramic sphere-based scaffolds with hierarchical pore structure for bone regeneration". Biofabrication. Apr. 24, 2017;9(2):025005. doi: 10.1088/1758-5090/aa6a62.

Klein, "Bone augmentation for cancellous bone using variable injectable composites as biomimetic agents". 2015, University of Zurich, Vetsuisse Faculty.

Kehoe, "Issue 4: Calcium Phosphates for Medical Applications". Jun. 2008. Dublin City University.

Conventus Orthopaedics, "Conventus CAGE™ PH Surgical Techniques". 2016.

* cited by examiner

IMPLANT FOR BONE FRACTURE STABILIZATION

REFERENCE TO RELATED APPLICATIONS

This application is a 371 national phase entry of PCT/CA2019/051113, which claims priority to, and the benefit of, U.S. provisional patent application No. 62/719,646 filed 18 Aug. 2018. Both of the foregoing applications are incorporated by reference herein in their entireties for all purposes.

TECHNICAL FIELD

Some embodiments of the present invention pertain to apparatus for stabilizing bone fractures. Some embodiments of the present invention pertain to apparatus comprising synthetic bone implants for stabilizing bone fractures. Some embodiments of the present invention pertain to methods for stabilizing bone fractures using such apparatus.

BACKGROUND

Bone fractures are a relatively common occurrence in modern society. Aging weakens bone in all individuals, and the risk of a fall that might fracture a bone increases with age. Thus, the likelihood of breaking a bone can increase with age. This risk increases for individuals suffering from osteoporosis, who are predisposed to fractures.

The architecture of normal bone in the inner metaphysis is one of a loose lattice of trabecular bone. That is to say the "marrow" of the metaphysis is characterized by a web or trellis of intertwined thin strands of bone; there is no mass of solid bone. With increasing age, the limbs of that lattice become even thinner and fewer in number. Osteoporosis is characterized by even greater loss of those lattice limbs.

Fracture healing is a 3-phase biologic process which is not significantly impaired or slowed by increasing age. It consists of inflammatory, reparative and remodeling phases. The phases see establishment of stability of upper extremity fractures within 4-6 weeks, and in general, somewhat longer in the lower extremities. A key to fracture healing is the microvascular environment and its integrity. Surgical techniques serve to provide immediate stability, but in so doing substantially lessen the contribution of external bridging callus to early fracture stabilization and healing, and disrupt the local soft tissue environment to further delay the normal fracture healing process.

In adults, the bones that are most often broken include the proximal femur (hip) and distal radius (wrist). The cost of dealing with such fractures is high, both in terms of the financial cost to the health care system and personal costs for the affected individual, including loss of functional freedom and mobility, as well as the obvious pain and suffering associated with a broken bone.

Fractures of the hip and wrist are often linked. One in four women over the age of 50 years has osteoporosis, which predisposes them to fractures. If such women experience such a fragility fracture they are up to seven times more likely to fracture another bone than a woman who does not have osteoporosis.

Conventional treatment for management of a distal radius fracture involves initial assessment, manipulation of the fracture in an effort to correct the deformity (which may be done under an anesthetic technique), and application of the first of one or more casts the patient will experience over the following six weeks. Generally, treatment is non-surgical, with surgical treatment being a lesser-used alternative (i.e. occurring in a minority of cases). The determination of whether to proceed by way of surgery is often made following the initial assessment, and may be made solely on the basis of the extent of bone reduction (i.e. how close to normal the bone appears). For non-operative treatment, the patient is subsequently clinically evaluated (including conduct of x-rays) on one or more occasions, and may be referred for physical therapy when the cast is removed, often after about six weeks. During the first six week period (even with diligent cast use), and to a lesser extent the second six week period following the fracture, there is some loss of the initial fracture reduction/position. There may often be a residual and predictable deformity.

The deformity may be predictable based on the initial fracture pattern. In some patients, based on the age-related brittleness, when the bone breaks it shatters rather than simply snaps. After reduction (i.e. an attempt to return the fracture to the correct alignment), there is no intrinsic stability afforded by the reduction—it has to collapse. While a cast can stabilize a fracture, to an extent facilitating healing, it cannot prevent such collapse. With the collapse there is an associated clinical deformity, a feature which offends many patients. It is also presumed, but not well established, that greater residual deformity is associated with poorer functional outcomes.

Surgical treatment can provide more predictable correction of fracture deformity. There are, however, technique-specific and general risks associated with surgery that can adversely impact the patient's ultimate outcome, and which can even necessitate one or more additional surgeries. Surgery is also more costly to the healthcare system than non-operative treatment.

If surgical treatment is selected, the patient may be brought to the hospital for outpatient surgical management. The surgical implant most often used is a rigid metal plate and screws that maintains the corrected fracture reduction. On occasion the surgeon may opt to augment the stability of this fixation by filling the void created by the crush of the fracture with bone graft taken from the patient (autograft), from a bone bank (allograft), or by using a synthetic material such as an orthobiologic bone substitute material (e.g., ceramic).

One of the ceramics that can be used as a suitable orthobiologic material is Norian SRS™, available as an injectable and moldable paste or as preformed solid granules, and FDA approved for use in distal radial fractures as a fracture void filler. One advantage of this biocompatible calcium phosphate product is that it can withstand compressive loading, with a compressive strength of approximately 50 MPa. This strength is 4-10 times greater than the compressive strength of metaphyseal cancellous bone, and is therefore capable of preventing fracture collapse. Another advantage is that it is gradually absorbed over time, as it closely resembles the mineral phase of bone. Thus, the biocompatible calcium phosphate fracture void filler ultimately remodels to new, structurally sufficient bone via cellular new bone formation.

Such fillers have been used to support surgical fixation, and are introduced in the operating room. As the paste is initially injected in a fluid state it is apt to spread to unintended areas unless local measures are taken to avoid this and to remove any material that has spread into the surrounding soft tissues. After injection the material is left undisturbed for a few minutes as it "cures" at body temperature into its solid state as a carbonated apatite.

Subsequent to surgical treatment, the patient adopts a post-operative program similar to that of the patient treated non-operatively, except that the duration of casting is considerably less (e.g. generally 2-4 weeks, rather than 6). The loss of reduction frequently seen in non-operative care is rare in the surgically treated patient.

Regardless of the treatment type, it has been the inventors' experience with conventional bone fracture treatments that by three months post-fracture patients have regained approximately 80-90% of their motion and 40% of their grip strength. At six months grip strength is about 60% of normal, and at one year is close to but still less than normal.

As mentioned previously, key to fracture healing are the microvascular environment and mechanical integrity. Surgical techniques serve to provide immediate stability (mechanical integrity) but, in so doing, disrupt the local soft tissue environment (including microvascular environment) and necessarily delay the normal fracture healing process. Thus, less invasive surgical stabilization techniques that are less disruptive of the microvascular environment are desirable. Also, small amounts of movement can be a stimulant to promote the early healing of a fracture external bridging callus. The use of plates and screws can prevent such movement from occurring, thereby potentially delaying healing.

Ceramic augments, such as Norian SRS™ described above, are provided as an injected paste or as prefabricated granules (2-3 mm diameter), and are solid. Bone cannot penetrate the material, and as such, the solid impedes local fracture repair and remodeling processes that would otherwise normally occur, at least until the material begins to resorb.

Worldwide, autografts and allografts are used in over two million orthopaedic procedures annually. Owing to the limitations and associated problems inherent with autografts and allografts, alternative bone substitute materials have been sought. So far, many of these have employed a variety of materials, including natural and synthetic polymers, ceramics, and composites, whereas others have incorporated factor- and cell-based strategies that are used either alone or in combination with other materials. However, despite the many advances in bone graft substitutes, no ideal bone substitute has been found. There remains a need for an alternative with optimal bone regeneration properties. In the orthobiologics' sector, there appears to be a growing preference towards the use of synthetic materials rather than traditional autografts and allografts. Synthetic materials and growth factors may be perceived as safer than allograft-based bone tissue.

A desirable surgical implant would provide rapid fracture stability, would not disturb the local microvascular network and trabecular bone architecture, and, once redundant (e.g. when fracture healing has occurred, typically approximately 6 to 12 weeks post-fracture), would be absorbed by the body, rather than requiring an additional surgical event to remove it. A desirable surgical implant should also allow for ease of deployment by the surgeon to minimize the complexity of using such implants. A desirable surgical implant could also minimize the amount of movement of the implant once inserted in place within a fracture cavity by the surgeon. There remains a need for new surgical techniques and new surgical implants for stabilizing bone fractures that provide improvements in one or more of the foregoing properties.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides an implant for insertion into a fracture cavity to stabilize a bone fracture, the implant comprising a rod having a curved or angled configuration, wherein the degree of curvature of the rod along its longitudinal axis or the angular configuration of the rod along its longitudinal axis is selected to correspond to a degree of curvature or flare of a portion of bone within the fracture cavity against which the rod is intended to be inserted. In some aspects, the shape of the rod is configured to be complementary to a shape of the local peripheral cortical bone adjacent to which the rod is to be deployed within the bone fracture. In some aspects, the rod is provided with structural features to minimize movement of the rod in its deployed position. In some aspects, the structural features include a projection for limiting rotational movement of the rod in its deployed position, the projection being configured to engage against the local peripheral cortical bone when the implant is in its deployed configuration to minimize rotational movement of the rod in the deployed position. In some aspects, the structural features are a component for engaging with a second rod to be deployed within the bone fracture.

In some aspects, a spherical implant is provided. In some aspects, the spherical implant is a perforated hollow sphere, a solid sphere with at least one perforation formed therein, or a solid sphere. In some aspects, once one or more rods have been inserted into a fracture cavity, a plurality of spherical implants are inserted into the fracture cavity to help stabilize the fracture cavity.

In some aspects, an implant for stabilizing a bone fracture has a first rod having a shape configured to be complementary to a shape of the local peripheral cortical bone adjacent to which the first rod is to be deployed within the fracture cavity, a second rod having a shape configured to be complementary to a shape of the local peripheral cortical bone adjacent to which the second rod is to be deployed within the fracture cavity, the first rod and the second rod having complementary engaging features so that the first rod and the second rod can be structurally linked together to limit relative movement of the first and second rods when deployed within the fracture cavity.

In some aspects, a method for stabilizing a bone fracture using an implant is provided. At least two rods are inserted into a fracture cavity within the bone to stabilize peripheral portions of the fracture cavity, and a plurality of spherical implants are inserted into the fracture cavity. In some aspects, the at least two rods are structurally linked together to minimize movement of the linked rods relative to one another when deployed in the fracture cavity.

In some aspects, a method of optimizing the shape and configuration of an implant for use in stabilizing a fracture where the implant is to be positioned adjacent to a particular surface of a fracture cavity defined by the fracture. The method includes preparing a model of the implant using an additive manufacturing method, inserting the model of the implant to a deployed configuration against the particular surface of the fracture in a model of the fracture cavity, evaluating fit and stability of the model of the implant against the particular surface of the fracture in the model of the fracture cavity, adjusting a shape of the model of the implant to enhance stability of the model of the implant in the deployed configuration to produce a revised model of the implant, preparing the revised model of the implant using the additive manufacturing method, inserting the revised model of the implant in the deployed configuration within the model of the fracture cavity, and evaluating fit and stability of the revised model of the implant against the particular surface of the fracture in the model of the fracture cavity.

In some aspects, kits comprising two or more of the implants and/or spherical implants as described herein are provided.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 7A is a front view, FIG. 7B is a side view, FIG. 7C is an end view, and FIGS. 7D, 7E and 7F are different perspective views thereof.

FIG. 8A is a front view, FIG. 8B is a side view, FIG. 8C is an end view and FIGS. 8D and 8E are different perspective views thereof.

DESCRIPTION

Figure 1A:
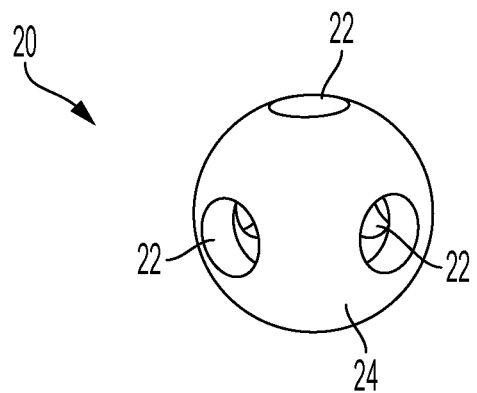
FIG. 1A is an example embodiment of a perforated hollow sphere for use in the stabilization of fractures.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Tertiary structures, such as orthobiologic rods or spheres, made from an orthobiologic material, including for example, a ceramic material such as calcium phosphate, can be used in the surgical management of bone fractures. In some embodiments, the tertiary structures made from an orthobiologic material are used in the management of metaphyseal fractures. In some embodiments, the tertiary structures made from an orthobiologic material are used in the management of distal radial fractures. It is anticipated that some embodiments of the present invention may minimize loss of function for patients, reduce overall healthcare costs, and/or return patients to work faster than conventional treatments.

In some example embodiments, an implant for stabilizing a bone fracture comprises a sphere made from an orthobiologic material. In some embodiments, the sphere is solid. In some embodiments, the sphere is hollow. In some embodiments, the sphere is hollow with perforations formed through a shell of the sphere, i.e. a perforated hollow sphere. In some embodiments, the sphere is solid with perforations formed in an outer surface of the sphere. In some embodiments, the sphere is solid and is provided with a plurality of interconnected perforations.

In one example embodiment, an implant for stabilizing a bone fracture comprises a hollow, perforated sphere made from an orthobiologic material. In one example embodiment, the orthobiologic material is a ceramic. By "hollow", it is meant that there is a significant void volume within the sphere, i.e. that the central region of the sphere is free of orthobiologic material. By "perforated", it is meant that one or more passageways are provided through the shell of the hollow sphere, to allow materials outside the sphere to enter the hollow portion of the sphere. In the context of a solid sphere, the term "perforated" means that one or more passageways are provided in the sphere. Such passageways can extend partially or fully through the sphere in various embodiments. In some embodiments, such passageways can be interconnected.

To clarify the meaning of "hollow" with an example, a hypothetical solid sphere with an outer diameter of 0.65 cm has a volume of approximately 0.144 $cm^3$ that comprises entirely solid material (and therefore 0.144 $cm^3$ of orthobiologic material would be required to manufacture such a sphere). A hypothetical example of a hollow sphere with an outer diameter of 0.65 cm and a wall thickness of 0.1 cm will have a "hollow" interior comprising approximately 0.048 $cm^3$ of that 0.144 $cm^3$ sphere volume. With this hollow centre of the sphere, 33% less material would be required to manufacture the hollow sphere compared to a solid sphere with the same diameter, i.e. each sphere would require approximately 0.096 $cm^3$ of orthobiologic material to manufacture such a sphere rather than 0.144 $cm^3$. In another example, if the sphere outer diameter measures 0.65 cm and the wall thickness is 0.05 cm, the total volume of the sphere would still be 0.144 $cm^3$ and the volume of the central hollow portion of the sphere would be 0.087 $cm^3$. In this scenario 60% less material would be required to manufacture the hollow sphere compared to the solid sphere with the same diameter, i.e. each hollow sphere would require approximately 0.057 $cm^3$ of orthobiologic material to manufacture. Thus, in some embodiments, the use of hollow spheres maximizes filling of the volume of the fracture void (i.e. the volume of the fracture void that is stabilized by tertiary orthobiologic structures), while minimizing the volume of orthobiologic material required for the manufacture of such spheres.

In some example embodiments, the spheres are provided with a plurality of rib-like reinforcements within the hollow sphere. In some example embodiments, the spheres are provided with a plurality of reinforcement struts within the hollow sphere. In some embodiments, for example embodiments where the diameter of the sphere is too small for providing a hollow sphere, one or more perforations in and/or through the sphere are provided. In some embodiments, one or a plurality of interconnected channels that extend through a solid sphere are provided.

In some example embodiments, the spheres have a diameter of approximately 5.5 to 7.5 mm, or any value therebetween, including 6.0, 6.5 or 7.0 mm. In some example embodiments, the spheres have a diameter in the range of 6.0 to 6.5 mm. In some example embodiments, a shell of a hollow sphere has a wall thickness of in the range of approximately 0.5 to 1.0 mm, or any value therebetween, e.g. 0.6, 0.7, 0.8 or 0.9 mm. In some example embodiments, the wall thickness of the shell of the hollow sphere is adjusted depending on the anticipated required load carrying capacity of the spheres. For example, in some embodiments in which it is anticipated that the hollow spheres should support high load, the thickness of the shell of the hollow sphere is increased, the number and/or thickness of rib-like reinforcements within the hollow sphere could be increased, and/or the number of perforations provided through the hollow sphere could be decreased.

In one example embodiment, a hollow, perforated sphere has a diameter of approximately 6.5 mm and a thickness of approximately 0.5 mm, and has six apertures therethrough providing perforations. In one example embodiment, the hollow, perforated sphere has a diameter of approximately 6.5 mm and a thickness of approximately 1 mm, and has six apertures therethrough providing perforations. In one example embodiment, the hollow, perforated sphere has a diameter of approximately 7 mm and a thickness of approximately 0.5 mm, and has six apertures therethrough providing perforations. In one example embodiment, the hollow, perforated sphere has a diameter of approximately 7 mm and a thickness of approximately 1 mm, and has six apertures therethrough providing perforations. In one example embodiment, the hollow, perforated sphere has a diameter of approximately 7 mm and a thickness of approximately 1 mm, and has five apertures therethrough providing perforations.

In some example embodiments, the hollow, perforated spheres have other diameters and thicknesses. For example, in some example embodiments intended for use with bones of a larger size, the diameter of the hollow perforated spheres may be increased. In some embodiments intended for use with bones of a smaller size, the diameter of the hollow perforated spheres may be decreased. For example, in some embodiments, the hollow perforated spheres have a diameter in the range of about 7.5 to about 10 mm, including any value therebetween, for example, 8.0 mm, 8.5 mm, 9.0 mm, or 9.5 mm. In some embodiments, the hollow perforated spheres have a diameter of greater than about 10 mm, e.g. 10.5 mm, 11.0 mm, 11.5 mm, 12.0 mm, or more. In some embodiments, the hollow perforated spheres have a diameter in the range of about 2.5 mm to about 5.5 mm, including any value therebetween, e.g. 3.0, 3.5, 4.0, 4.5 or 5.0 mm.

In some embodiments, the implants, e.g. spheres or rods, are made from an orthobiologic material. In some embodiments, the implants are made from a ceramic. In some embodiments, the implants are made from calcium phosphate. In some example embodiments, the implants are made from Norian™ calcium phosphate ceramic, e.g. Norian™ SRS™ or equivalent. In some other example embodiments, the implants are made from any other form of orthobiologic, ceramic or calcium phosphate suitable for introduction into bone; for example, hydroxyapatite, biphasic calcium phosphate, α- or β-tricalciumphosphate, or the like, or from any other type of bone filler or substitute ceramic material, including for example coralline hydroxyapatite, collagen-based matrices including mineralized collagen matrices, calcium phosphate, calcium sulfate, calcium carbonate, demineralized bone matrix, including fibers prepared using demineralized bone matrix, bioactive glass, hydroxyapatite/calcium carbonate composites, suitable polymers or copolymers, or the like. Examples of potentially suitable materials for making implants according to example embodiments of the present invention include those listed by the American Academy of Orthopaedic Surgeons (AAOS) in their Bone Graft Substitutes Table entitled "Summary of typical bone-graft substitutes that are commercially available—2010", e.g. AlloFuse™, BonePlast™, BonePlast™ Quick Set, InterGro™, ProOsteon™ 500R, CONDUIT™ TCP Granules, HEALOS™ Bone Graft Replacement, Optecure™, Optecure™+cortical cancellous chips, Optefil™, Opteform™, OpteMx™, Accell Connexus™, Accell Evo3™, Accell TMB™, DynaGraft II, OrthoBlast II, Integra Mozaik™, IC Graft Chamber™, Optium DBM™, INFUSE™ Bone Graft, MasterGraft™ Granules, MasterGraft™ Matrix, MasterGraft™ Strip, Osteofil™ DBM, Progenix™ Plus, Trinity Evolution™, DBX™, NovaBone™, Vitoss™, GRAFTON™ A-Flex™, GRAFTON™ Crunch™, GRAFTON™ Flex™, GRAFTON™ Matrix PLF, GRAFTON™ Matrix Scoliosis Strips, GRAFTON™ Orthoblend Large Defect, GRAFTON™ Orthoblend Small Defect, BioSet™, VIAGRAF, OP-1™ Implant, Calceon™ 6, chronOS™, Norian™ SRS™, ALLOMATRIX™, ALLO-MATRIX™ RCS, ALLOPURE™, CANCELLO-PURE™ Wedges, CELLPLEX™, IGNITE™, OSTOSET™, CopiOs™ Bone Void Filler, CopiOs™ Cancellous Bone Graft, Puros™ DBM. Other suitable materials for use in some embodiments of the invention can be selected by those skilled in the art, and the appended claims include within their scope bone graft substitute materials now known or developed in future. As used herein, the term "orthobiologic material" encompasses all such potentially suitable materials disclosed in this paragraph.

Figure 1B:
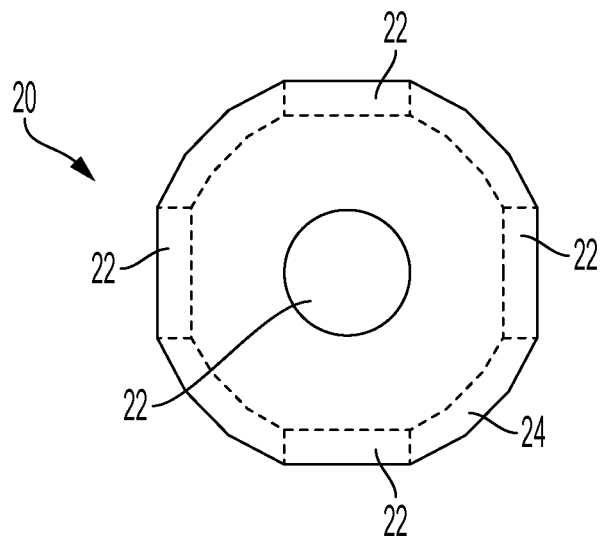
FIG. 1B is a cross-sectional view of an example embodiment of a perforated hollow sphere having an exemplary wall thickness of 0.5 mm and six apertures therethrough providing perforations.

In one example embodiment of an implant for stabilizing a bone fracture, as illustrated in FIGS. 1A and 1B, the sphere 20 is hollow and is provided with a plurality of apertures 22 through a thickness of the shell 24 of sphere 20. Apertures 22 are perforations through the shell 24 of sphere 20. In the illustrated embodiment, sphere 20 is provided with six apertures 22 spaced approximately equidistantly on the surface of sphere 20. In alternative embodiments, the number and/or position of apertures 22 could be varied, so long as apertures 22 provide access through shell 24 from the outside of sphere 20 to the inside of sphere 20. In the illustrated embodiment of FIG. 1B, sphere 20 can be provided with an exemplary wall thickness of 0.5 mm. Other wall thicknesses could be used in alternative embodiments.

In some embodiments, shell 24 is porous. In some embodiments, shell 24 is microporous. In some embodiments, the pores in shell 24 have an average diameter on the order of about 1 μm to about 100 μm or any value therebetween, including for example 5, 10, 15, 20, 25, 30, 35, 40, 45, 50, 55, 60, 65, 70, 75, 80, 85, 90 or 95 μm.

In some embodiments, at least the outer surface of shell 24 has a rough finish or texture. A "rough finish" is distinguished from a smooth or highly polished surface. In some embodiments, the rough finish of the outer surface of shell 24 arises as a result of the porous nature of the material used to form sphere 20. In some embodiments, surface treatments could be applied to provide a rough texture to the outer and/or inner surface of shell 24. For example, in some embodiments, an implant could be produced in a mold, and then the surface of the implant could be polished or slightly roughened in order to alter the texture of the outer and/or inner surfaces of the implant.

Without being bound by theory, because the orthobiologic spheres 20 are hollow and perforated, they take up little volume of the void in the bone fracture, which is intended to minimally impede the process of normal bone healing, and in fact to facilitate normal bone healing by providing a ready-made structural scaffold, or lattice, on which new bone can be laid. In some embodiments, the orthobiologic material from which the spheres are made is gradually reabsorbed over time. Further without being bound by theory, embodiments of the spheres that have a rough finish or texture on at least the outer surface of shell 24 may minimize sliding of the implants once inserted into a fracture cavity, which may increase overall fracture stability.

Without being bound by theory, the apertures 22 in the illustrated embodiment allow blood from the fracture hematoma to enter the inside of sphere 20. The influx of this blood into sphere 20 can facilitate the process of normal bone healing, as the process of new bone formation associated with fracture healing is believed to occur not only outside, but also within, the hollow sphere.

While in the illustrated embodiment the structure of sphere 20, including the shape and position of apertures 22, has been illustrated as generally symmetrical and uniform, in other embodiments, sphere 20 could have other shapes, be of asymmetrical or imperfect spherical shape, and apertures 22 could have different shapes and be distributed in varying locations on shell 24.

Figure 1C:
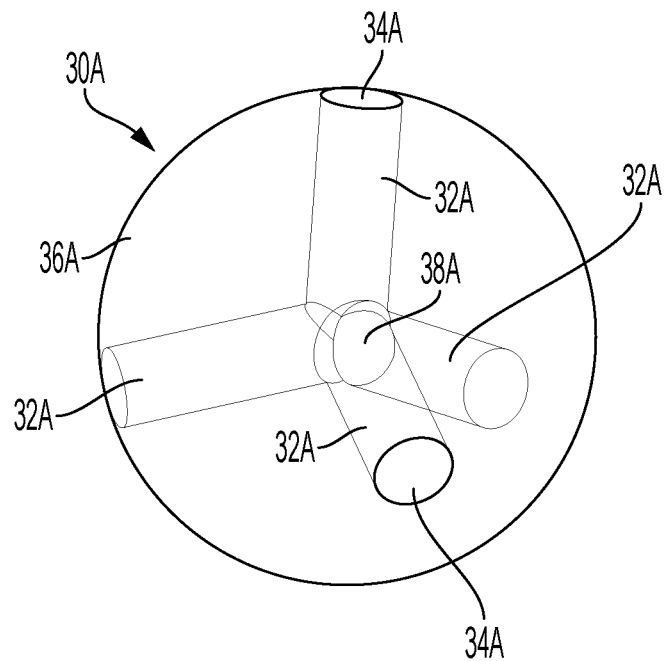
FIG. 1C is an example embodiment of a 4-hole sphere having four interconnected channels.
Figure 1D:
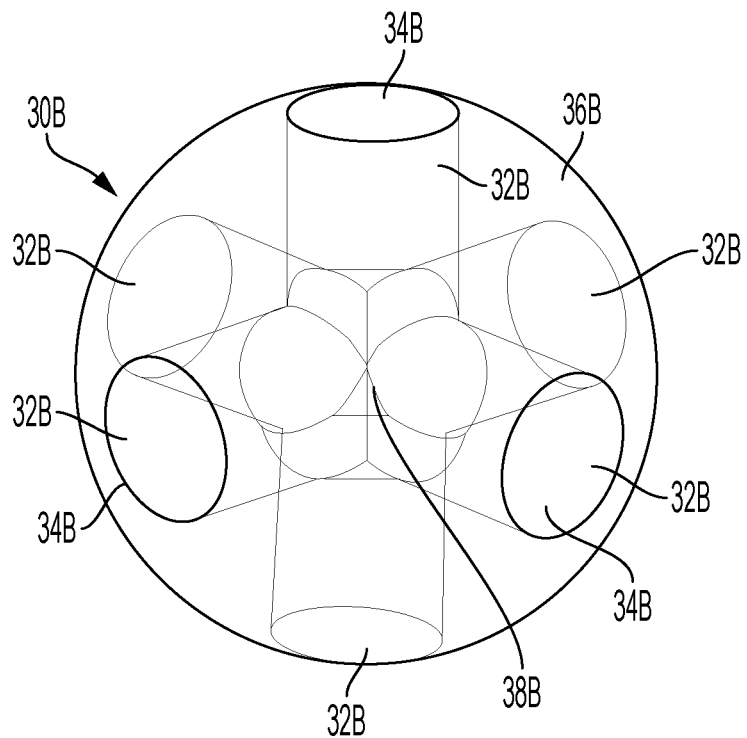
FIG. 1D is an example embodiment of a 6-hole sphere having six interconnected channels.

In another example embodiment, as illustrated in FIGS. 1C and 1D, a solid sphere, illustrated as 30A and 30B, respectively, and referred to throughout this disclosure as sphere 30, is provided with at least one or a plurality of interconnected channels or perforations formed therethrough. In the embodiment illustrated in FIG. 1C, a solid sphere 30A with four interconnected channels 32A is provided. Each one of channels 32A forms a hole 34A at the location where channel 32A intersects the outer surface 36A of sphere 30A.

In the illustrated embodiment, each one of holes 34A are equidistant from the other holes 34A. Thus, when a first one of the channels 32A is oriented vertically and its corresponding hole 34A is positioned at the topmost point of sphere 30A, each one of the lower holes 34A is oriented at an angle of 109.5 degrees from the hole 34A positioned at the topmost point of sphere 30A, and at an angle of 120 degrees with respect to the other lower holes 34A. In the illustrated embodiment, the axes of each one of channels 32A extend through the centrepoint 38A of sphere 30A.

As shown in FIG. 1D, in an alternative embodiment, a solid sphere 30B is provided with six interconnected channels 32B. Each one of channels 32B forms a hole 34B at the location where channel 32B intersects the outer surface 36B of sphere 30B.

In the illustrated embodiment, each one of holes 32B is equidistant from the other holes 32B. Thus, the angle between each respective adjacent pair of holes 32B is 90 degrees. In the illustrated embodiment, the axes of each one of channels 32B extend through the centerpoint 38B of sphere 30B.

Figure 1E:
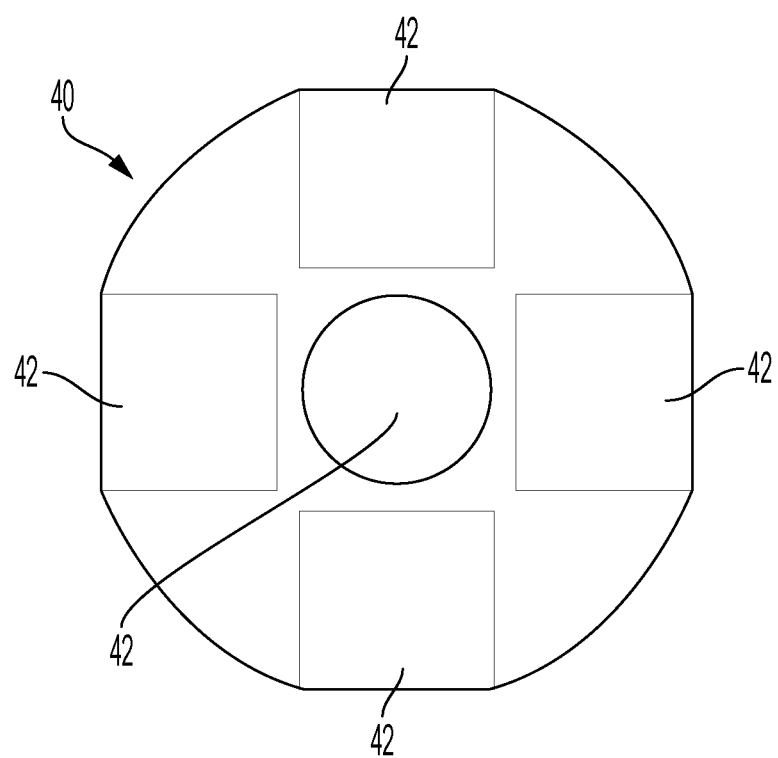
FIG. 1E is an example embodiment of a perforated solid sphere. This example embodiment of a perforated solid sphere has six perforations.

As illustrated in FIG. 1E, in some embodiments, a solid sphere with at least one or a plurality of perforations formed in an outside surface thereof is provided. In the illustrated embodiment, sphere 40 is provided with six perforations 42 formed in an outside surface thereof. Unlike channels 32, perforations 42 do not intersect with one another (i.e. are not interconnected) and do not extend through a centrepoint of sphere 40. Without being bound by theory, it is believed that embodiments in which perforations 42 do not pass through a centrepoint of sphere 40 may be stronger than embodiments in which the channels 32 do intersect and extend through a centrepoint of the sphere 30, since the interconnected channels 32 may weaken the core of sphere 30.

In some embodiments, the material from which spheres 30 or 40 are made is porous. In some embodiments, the material from which spheres 30 or 40 are made is microporous. In some embodiments, the pores in the material from which spheres 30 or 40 are made have an average diameter on the order of about 1 µm to about 100 µm or any value therebetween, including for example 5, 10, 15, 20, 25, 30, 35, 40, 45, 50, 55, 60, 65, 70, 75, 80, 85, 90 or 95 µm.

In some embodiments, at least the outer surface of spheres 30 or 40 has a rough finish or texture. A "rough finish" is distinguished from a smooth or highly polished surface. In some embodiments, the rough finish of the outer surface of spheres 30 or 40 arises as a result of the porous nature of the material used to form spheres 30 or 40. In some embodiments, surface treatments could be applied to provide a rough texture to the outer surface and/or channels or perforations formed in spheres 30 or 40. For example, in some embodiments, an implant could be produced in a mold, and then the surface of the implant could be polished or slightly roughened in order to alter the texture of the outer and/or inner surfaces of the implant.

In another example embodiment of an implant for stabilizing a bone fracture, an implant that is a rod is provided. In some embodiments, the rod is solid. In some embodiments, the rod could be a perforated hollow shell, optionally containing reinforcing ribs or struts. Without being bound by theory, in some embodiments rods that are solid and porous may be stronger than rods that are perforated hollow shells. In some embodiments, the rods include apertures or other openings therein or therethrough rather than being completely solid. In some embodiments, the apertures or other openings are constructed so that they do not significantly adversely impact the load carrying capacity of the rods. In some embodiments, the rods are provided with protrusions or projections that can engage with other rods, spheres, and/or anatomical features of a patient, to better secure the rods in place within a fracture cavity. In some embodiments, the rods are made from a non-resorbable material, e.g. a biocompatible metal. In some embodiments, the rods are made from an orthobiologic material.

In various embodiments, the rod can be provided with any height and configuration, depending on the local peripheral cortical bone anatomy of the location where the rod will be implanted. In some embodiments, the rods are generally cylindrical about a longitudinally-extending axis. In some embodiments, the rods are generally cylindrical, but are curved and/or angled relative to their longitudinally-extending axis, for example to conform to the local peripheral cortical bone anatomy of the location where the rod will be implanted in use at a location where the bone flares. In some embodiments, the degree of curvature and/or angle of the rod is selected to correspond generally with an angle or degree of flare exhibited by a portion of a bone in which the rod is to be inserted, so that the rod can be better retained in position within the fracture cavity. For example, in one example embodiment, a rod that is intended to be inserted adjacent the volar floor of a distal radius is provided with a significant angle and/or degree of bend away from its longitudinal axis, to enable the rod to conform to the flare of the distal radius. In another example embodiment, a rod that is intended to be inserted radially within a distal radius is provided with a slight angle and/or degree of bend away from its longitudinal axis, to enable the rod to conform to the mild flare of the distal radius at that location.

In some embodiments, a pair of rods that are engageable with one another are provided. Each rod of the pair of rods is provided with surface features that are complementary to corresponding surface features provided on the other one of the pair of rods. For example, in some embodiments, a first rod of the pair of rods is provided with a projection, and a second rod of the pair of rods is provided with a corresponding aperture for receiving the projection. In some embodiments, the connection between the first and second rods of the pair of rods is moveable to provide for an insertion configuration, in which the first and second rods are engaged together but configured to have a relatively narrow diameter (for example to allow for insertion through an aperture drilled or formed in a bone), and a deployed configuration, in which the first and second rods are rigidly engaged together in a configuration complementary to the bone in which the pair of rods is deployed, to minimize movement of the pair of rods within the bone.

In some embodiments, the rods are made from a non-resorbable material, e.g. a biocompatible metal. Examples of biocompatible metals include titanium, stainless steel, or titanium alloys. In some embodiments, the rods are made from an orthobiologic material.

Figures 2A, 2B, 2C:
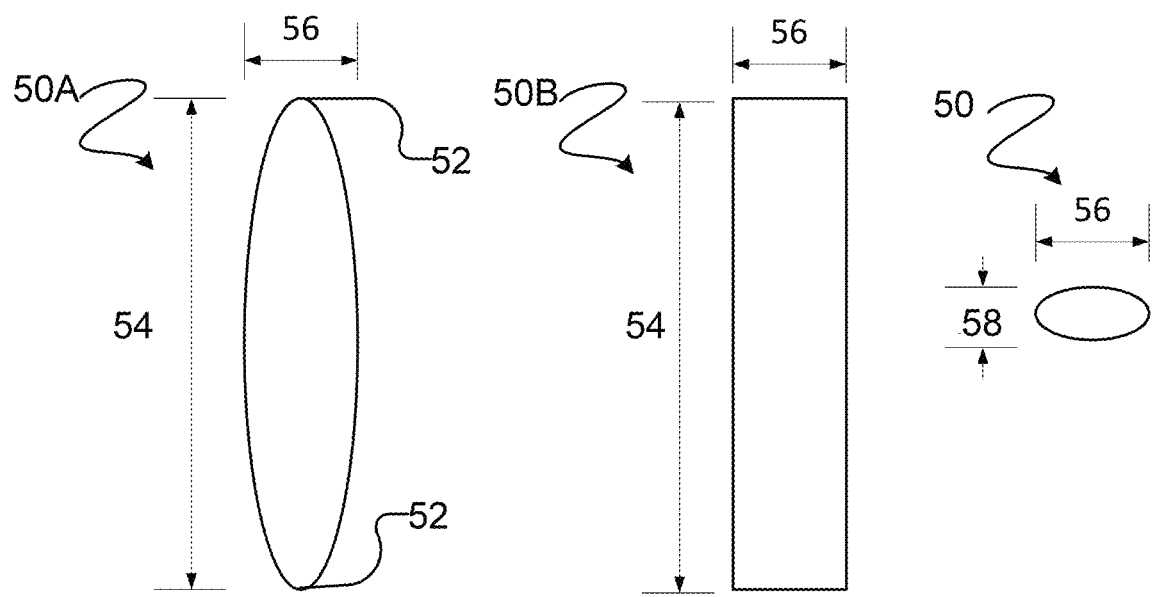
FIG. 2A is a side view of an example embodiment of a rod for use in the stabilization of fractures, highlighting the elliptical shape of the implant.
FIG. 2B is a side view of a second example embodiment of a rod for use in the stabilization of fractures.
FIG. 2C is an end view of an example embodiment of a rod for use in the stabilization of fractures.

With reference to FIG. 2A, in one example embodiment, rod 50A is generally cylindrical along its longitudinal axis (the direction of height 54 in FIG. 2A) and has axially-opposite tapered ends 52. With reference to FIG. 2B, in another example embodiment, rod 50B is generally cylindrical throughout its axial height and has no curved ends. In alternative embodiments, the rod may be provided with other shapes, for example, generally rectangular. With reference to FIG. 2C, in some embodiments, including the embodiments illustrated in FIGS. 2A and 2B, the rod 50 has a generally elliptical cross-section when viewed looking down its longitudinal axis. In some embodiments, the length 56 of rod 50 is greater than the width 58 (FIG. 2C) of rod 50 to provide this elliptical cross-section. In some embodiments, rod 50 has a generally circular cross-section, i.e. the length 56 is equal or approximately equal to the width 58.

In some example embodiments, the rod has an axial height 54 in the range of about 25 mm to about 50 mm or any value therebetween (including 30 mm, 35 mm, 40 mm or 45 mm), a length 56 in the range of about 2 to 4 mm, and a width 58 in the range of about 2 to 4 mm. In some embodiments, the rod has a length 56 of about 4 mm and a width 58 of about 2 mm.

In one embodiment, the rods have an axial height 54 in the range of about 25 to about 35 mm and are generally straight along their axial height. In some embodiments, such rods are referred to as "short rods". In some embodiments in which the rods are generally straight along their axial height, such rods are referred to as "straight rods". Thus, in some embodiments, a "short straight rod" refers to a rod having an axial height in the range of about 25 to about 35 mm that is generally straight (i.e. not bent or angled) along its axial height.

In one embodiment, the rods have an axial height 54 of about 35 mm to about 50 mm. In some embodiments, such rods are referred to as "long rods". In some embodiments, the long rods are provided with a curvature and/or one or more angled regions (or bends) along their axial height. In some embodiments, rods with a curvature or angled region (s) along their axial height are referred to as "curved rods". In some embodiments, the long rods are curved along their axial height to match the curvature of the local peripheral cortical bone anatomy of the location where the rod is intended to be implanted. In some embodiments, rods with one or more angled portions (or bends) along their axial height are referred to as "angled rods". In some embodiments, the long angled rods are angled at one or more locations along their axial height to match approximately the curvature of the local peripheral cortical bone anatomy of the location where the rod is intended to be implanted. In some embodiments, the rods are provided with a curvature and/or cumulative angle provided by one or more bends provided along their axial height in the range of about 10 degrees to about 30 degrees, including any value therebetween, e.g. 11, 12, 13, 14, 15, 16, 17, 18, 19, 20, 21, 22, 23, 24, 25, 26, 27, 28 or 29 degrees.

Figure 3A:
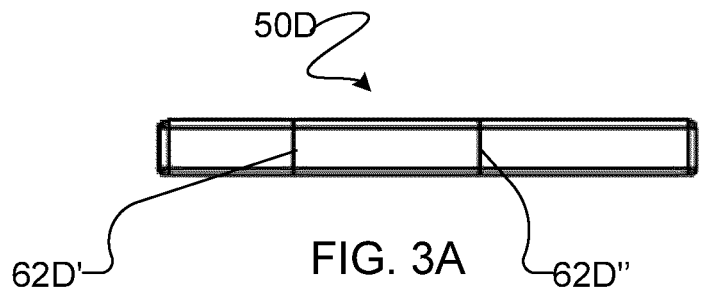
FIGS. 3A, 3B and 3C show top, side and isometric views, respectively, of an example embodiment of a rod for use in the stabilization of fractures, the rod having two bends with angular changes totaling 10 degrees along its axial height.
Figure 3B:
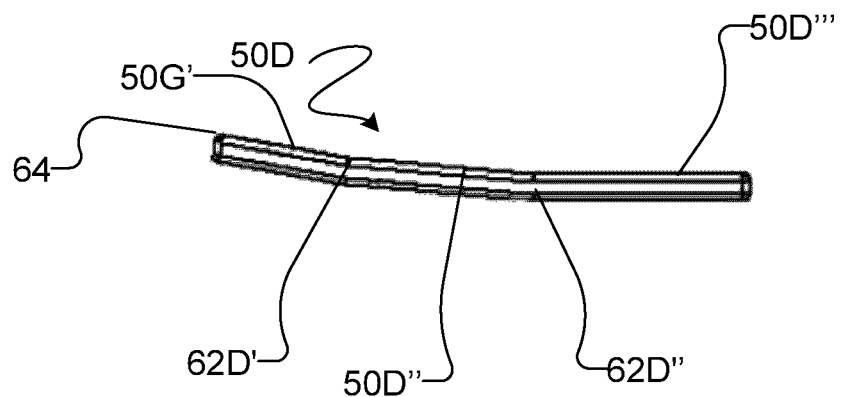
Figure 3C:
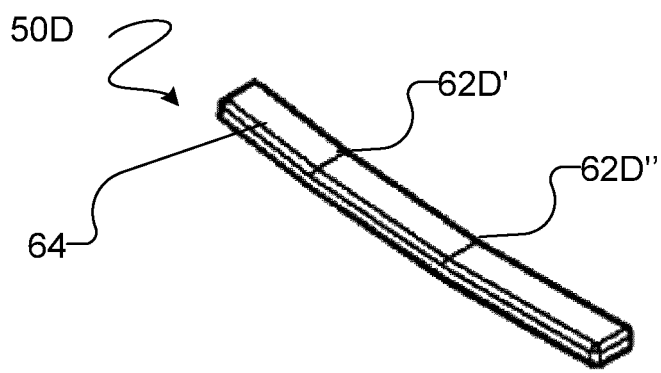

In some embodiments, the rod is provided with two or more bends or elbows. In the example embodiment illustrated in FIGS. 3A, 3B and 3C, an example embodiment of a rod 50D has two bends 62D' and 62D" along its axial height. The dimensions described with reference to FIGS. 3A-3C are exemplary only. In this example embodiment, first bend 62D' is provided approximately 9.5 mm from a first distal end of rod 50D, and second bend 62D" is provided approximately 25.5 mm from the first distal end, while rod 50D has a total axial height of approximately 39 mm. First bend 62D' provides an angle of approximately 5 degrees between first portion 50D' and second portion 50D" of rod 50D. Second bend 62D" provides an angle of approximately 5 degrees between second portion 50D" and third portion 50D''' of rod 50D. Thus, first and second bends 62D' and 62D" together provide a total angular change of 10 degrees along the axial height of rod 50D. Rod 50D is provided with a length of approximately 4 mm, a width of approximately 2 mm, and a cornered edge 64 approximately 0.5 mm across around its outer periphery.

Figure 4A:
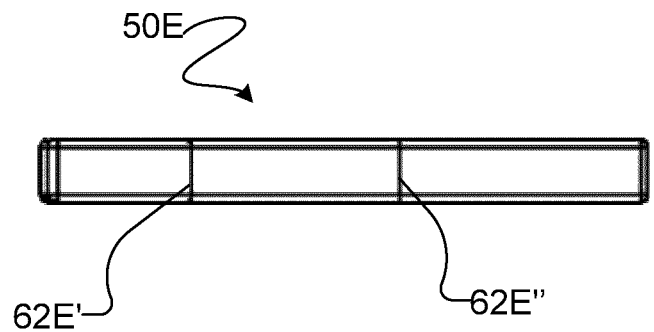
FIGS. 4A, 4B and 4C show top, side and isometric views, respectively, of an example embodiment of a rod for use in the stabilization of fractures, the rod having two bends with angular changes totaling 25 degrees along its axial height.
Figure 4B:
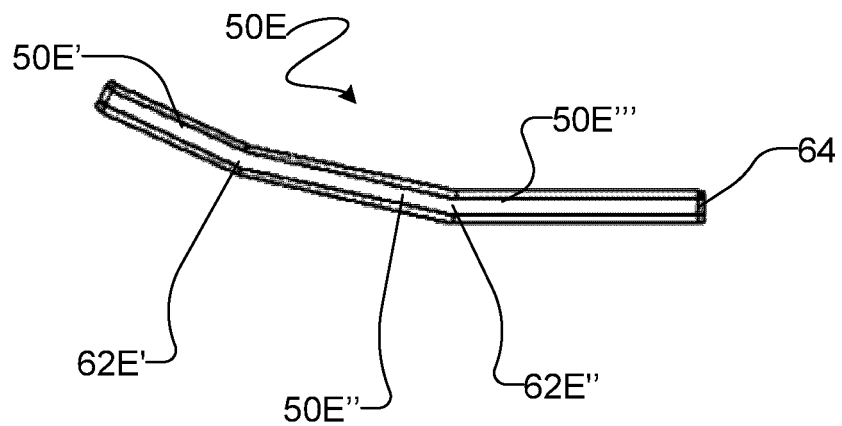
Figure 4C:
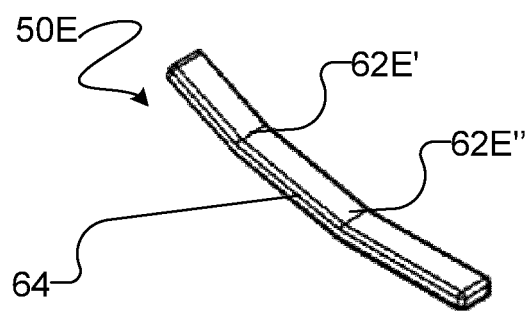
Figure 5A:
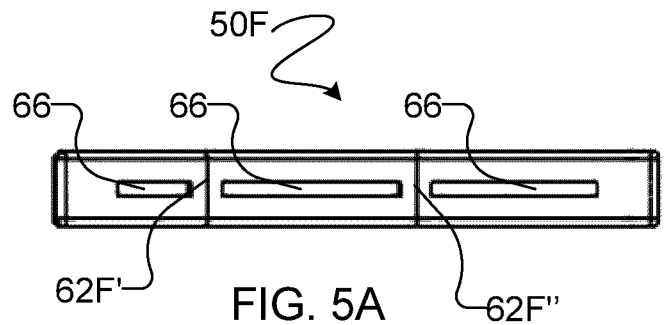
FIGS. 5A, 5B and 5C show top, side and isometric views, respectively, of an example embodiment of a rod for use in the stabilization of fractures, the rod having two bends with angular changes totaling 10 degrees along its axial height, the rod further comprising a plurality of longitudinally extending apertures therethrough, referred to as "through holes".
Figure 5B:
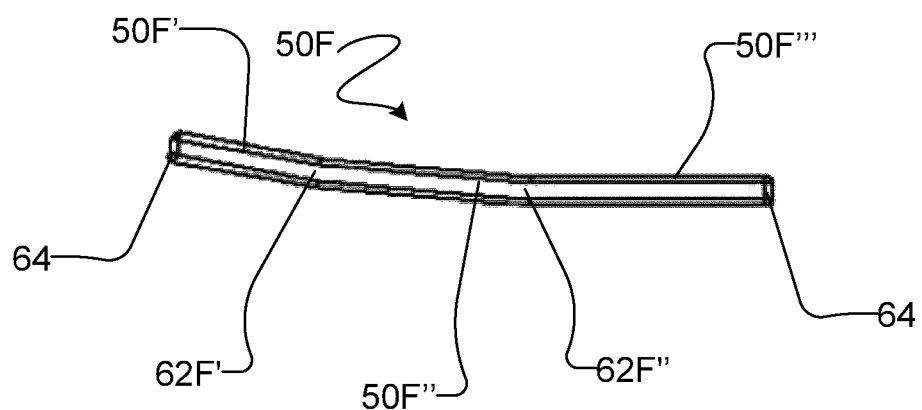
Figure 5C:
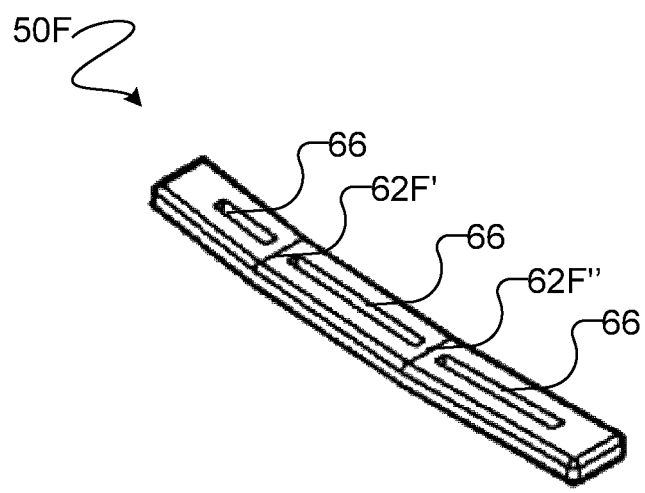
Figure 6A:
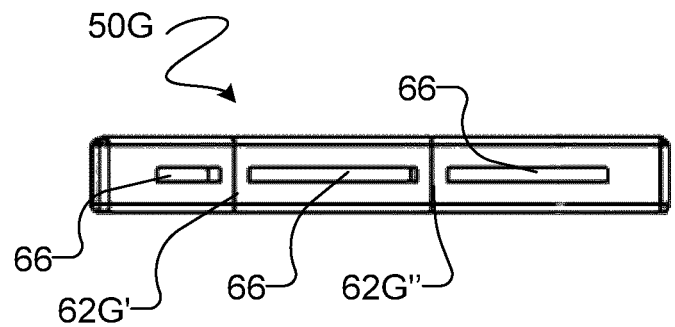
FIGS. 6A, 6B and 6C show top, side and isometric views, respectively, of an example embodiment of a rod for use in the stabilization of fractures, the rod having two bends with angular changes totaling 25 degrees along its axial height, the rod further comprising a plurality of longitudinally extending apertures therethrough, referred to as "through holes".
Figure 6B:
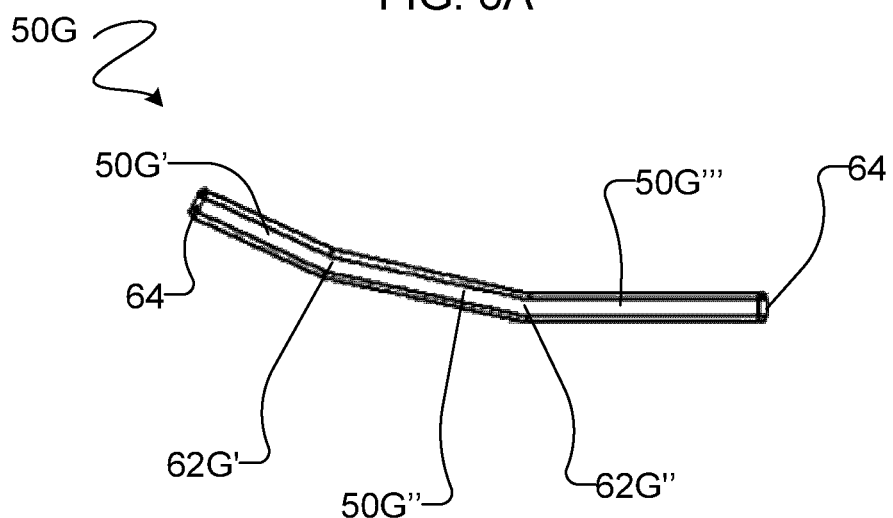
Figure 6C:
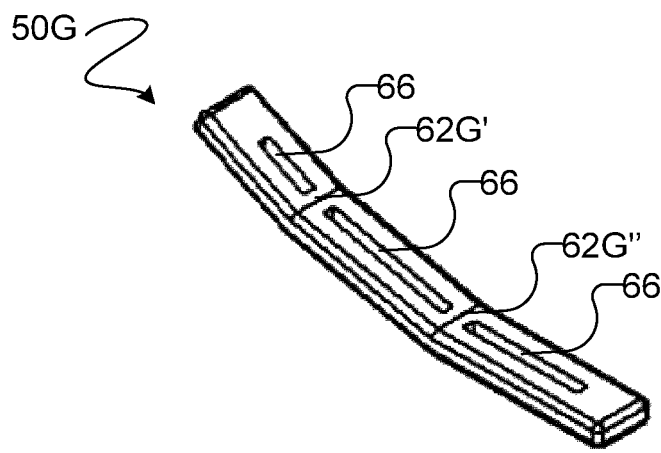

In the example embodiment illustrated in FIGS. 4A, 4B and 4C, an example embodiment of a rod 50E has two bends 62E' and 62E" along its axial height. The dimensions described with reference to FIGS. 4A-4C are exemplary only. In this example embodiment, first bend 62E' is provided approximately 9.5 mm from a first distal end of rod 50E, and second bend 62E" is provided approximately 23.5 mm from the first distal end, while rod 50E has a total axial height of approximately 39 mm. First bend 62E' provides an angle of approximately 12.5 degrees between first portion 50E' and second portion 50E" of rod 50E. Second bend 62E" provides an angle of approximately 12.5 degrees between second portion 50E" and third portion 50E''' of rod 50E. Thus, first and second bends 62E' and 62E" together provide a total angular change of 25 degrees along the axial height of rod 50E. Rod 50E is provided with a length of approximately 4 mm, a width of approximately 2 mm, and a cornered edge 64 approximately 0.5 mm across around its outer periphery.

While in the illustrated embodiment rods 50D and 50E have been illustrated as having a generally smooth surface and cornered edges, in other embodiments, the rods are provided with a rough surface and/or with rounded edges.

In the example embodiments illustrated in FIGS. 5A, 5B, 5C and 6A, 6B and 6C, rods 50F and 50G are generally similar to rods 50D and 50E, described above, respectively. However, rods 50F and 50G further include apertures 66 therethrough. In the illustrated embodiment, apertures 66 comprise longitudinally extending channels extending transversely through first, second and third portions 50F', 50F", 50F''' and 50G', 50G'', 50G'''. In the illustrated embodiment, apertures 66 have a width of approximately 1 mm, although this is an exemplary value only. In consequence of the presence of apertures 66, the width of rods 50F and 50G has been increased as an example only from 4 mm to 5 mm, relative to the embodiments illustrated in FIGS. 3A-3C and 4A-4C.

Apertures 66 can take any suitable form and shape, so long as they do not significantly adversely affect the load carrying capacity of the rods 50.

In some embodiments similar to those shown in FIG. 3A-3C, 4A-4C, 5A-5C or 6A-6C in which the rod is intended to be implanted in the distal radius, the rod has an axial height in the range of about 35 to about 50 mm, a pair of bends are located approximately 10 and 25 mm from one of the distal ends of the rod, and the bends together provide a combined bend in the range of about 15 degrees to about 30 degrees. In some embodiments in which the rod is intended to be implanted in the ulnar or dorsal portion of the distal radius, the bends subtend an angle in the range of about 10 to about 20 degrees. In some embodiments in which the rod is intended to be implanted in the volar portion of the distal radius, the bends subtend an angle in the range of about 15 to about 30 degrees. In some embodiments in which the rod is intended to be implanted in the radial portion of the distal radius, the bends subtend an angle in the range of about 5 to about 20 degrees.

In some embodiments, without being bound by theory, it is believed that providing a rod with a shape that conforms approximately with the shape of the local peripheral cortical bone anatomy of the location where the rod will be implanted increases the overall stability of the fracture by better retaining the implanted rod in position.

With reference to FIGS. 7A, 7B, 7C, 7D, 7E and 7F, a further example embodiment of a rod 50H is illustrated. The dimensions described with reference to FIGS. 7A-7F are exemplary only and are not limiting. Rod 50H is an example of a first rod that is engageable with a second rod 50I described below to provide an increased degree of stabilization within the fracture cavity. Rod 50H is a volar rod, i.e. is intended to be inserted on the volar aspect of a fracture cavity. Rod 50H is shaped and configured to have a shape complementary to the peripheral cortical bone along the volar aspect of the fracture cavity into which rod 50H is intended to be inserted.

Volar rod 50H is provided with surface features that enable it to conform to the shape of the volar aspect of a fracture cavity. In the illustrated embodiment, volar rod 50H is generally elongate and has a proximal end 102, a middle portion 104 and a distal portion 106. Volar rod 50H is shaped and configured to have a shape complementary to the shape of the volar aspect of a fracture cavity in a fracture of the distal radius, to assist in securing volar rod 50H in place when in use.

Figure 7A:
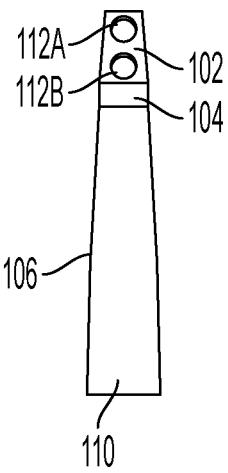
FIGS. 7A, 7B, 7C, 7D, 7E, and 7F show an example embodiment of a volar rod for use in the stabilization of fractures.
Figure 7B:
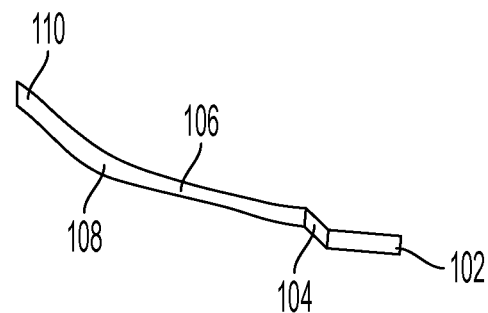
Figure 7C:
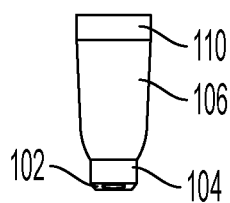
Figure 7D:
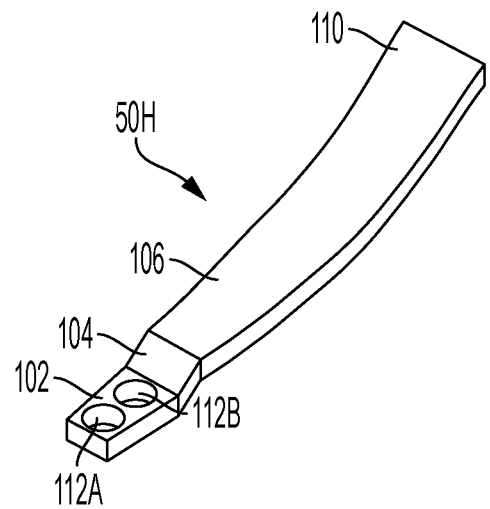
Figure 7E:
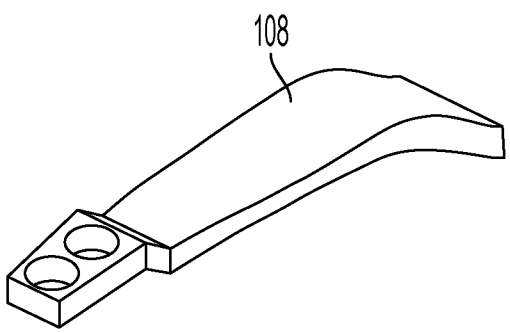
Figure 7F:
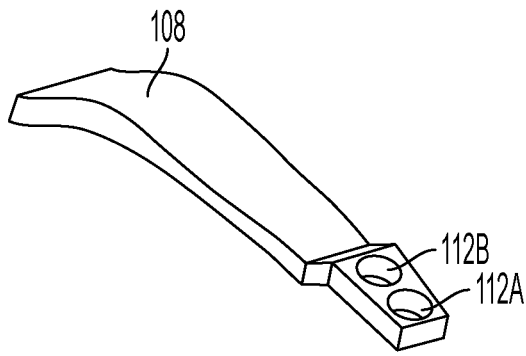

As best seen in the side view shown in FIG. 7B, proximal end portion 102 is angled slightly upwardly relative to a horizontal plane in the direction from its proximal end to its distal end, e.g. in the range of 2° to 10° including any value therebetween, e.g. 3°, 4°, 5°, 6°, 7°, 8° or 9°; middle portion 104 is angled more sharply upwardly relative to a horizontal plane in the direction from its proximal end to its distal end, e.g. in the range of 10° to 45°, including any value therebetween, e.g. 15°, 20°, 25°, 30°, 35° or 40°, and distal portion 106 is curved slightly upwardly relative to a horizontal plane in the direction from its proximal end to its distal end, curving to a bend 108 provided in a middle portion of distal portion 106, e.g. at an angle in the range of 2° to 15° including any value therebetween, e.g. 3°, 4°, 5°, 6°, 7°, 8°, 9°, 10°, 11°, 12°, 13° or 14°, and then more sharply curved upward relative to a horizontal plane in the direction from bend 108 to distal tip 110, e.g. at an angle in the range of 10° to 45°, including any value therebetween, e.g. 15°, 20°, 25°, 30°, 35° or 40°.

In some embodiments, including the illustrated embodiment, the distal portion 106 of volar rod 50H is slightly wider in the region of bend 108 and/or distal tip 110 than along other portions of its length. E.g. in some embodiments, the bend 108 and/or the distal tip 110 are in the range of 1% to 10% wider than the width of the remaining portions of distal portion 106, including any value therebetween, e.g. 2%, 3%, 4%, 5%, 6%, 7%, 8% or 9% wider.

In some embodiments, including the illustrated embodiment, the proximal end 102 of volar rod 50H and the middle portion 104 are narrower in width than distal portion 106. E.g. in some embodiments, proximal end 102 and middle portion 104 may have a width that is in the range of 10% to 50% of the average width of distal portion 106, including any value therebetween e.g. 15%, 20%, 25%, 30%, 35%, 40% or 45%.

In addition to being provided with surface features that enable it to conform to the shape of the volar aspect of a fracture cavity, volar rod 50H is also provided with structural features that allow it to be engaged with radial rod 50I described below. In the illustrated embodiment, volar rod 50H is provided with a pair of apertures 112A, 112B at its proximal end 102 that are sized and dimensioned to receive a corresponding projection provided on radial rod 50I as described below, and these corresponding apertures and projecting rod constitute structural features for engaging the two implants.

In the illustrated embodiment and by way of example only, volar rod 50H may be provided with an overall length of 31.5 mm, and may taper from its proximal end to its distal end in the range of about 3 mm to about 6 mm in width, and the length of middle portion 104 may be about 1.5 mm and the thickness of volar rod 50H may be about 1.5 mm.

With reference to FIGS. 8A, 8B, 8C, 8D and 8E, a further example embodiment of a rod 50I is illustrated. The dimensions described with reference to FIGS. 8A-8E are exemplary only and are not limiting. Rod 50I is a radial rod, i.e. is intended to be inserted along a radial aspect of a fracture cavity.

Rod 50I is provided with surface features that enable it to conform to the shape of the radial aspect of a fracture cavity into which rod 50I is intended to be inserted. In the illustrated embodiment, radial rod 50I has a proximal end 120, a middle portion 122 and a distal portion 124. Radial rod 50I is shaped and configured to have a shape complementary to the shape of the radial aspect of a fracture cavity in a fracture of the distal radius, to assist in securing radial rod 50I in place when in use.

Figure 8A:
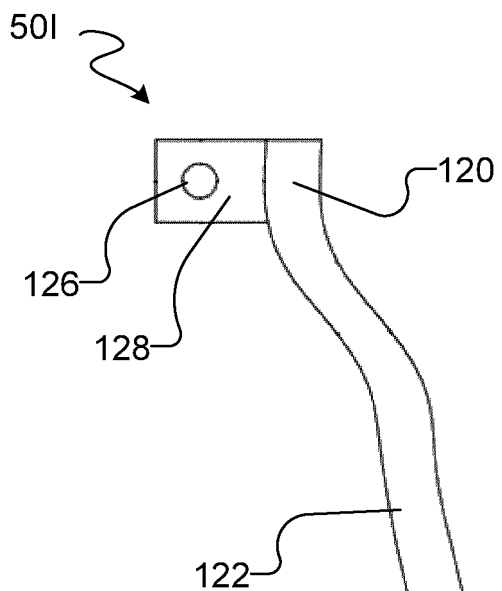
FIGS. 8A, 8B, 8C, 8D and 8E show an example embodiment of a radial rod for use in the stabilization of fractures.

In the illustrated embodiment, as best seen in the front view of FIG. 8A, radial rod 50I is angled laterally outwardly from its proximal to its distal end. Proximal end 120 of radial rod 50I is curved gently laterally outwardly from its proximal end in the distal direction (i.e. to the right in the front view of FIG. 8A), e.g. at an angle in the range of 10° to 45°, including any value therebetween, e.g. 15°, 20°, 25°, 30°, 35° or 40°. Middle portion 122 of radial rod 50I is also curved gently laterally outwardly from its proximal end in the distal direction, e.g. at an angle in the range of 10° to 45°, including any value therebetween, e.g. 15°, 20°, 25°, 30°, 35° or 40°. Distal portion 124 of radial rod 50I is also gently curved laterally outwardly in the distal direction, e.g. at an angle in the range of 10° to 45°, including any value therebetween, e.g. 15°, 20°, 25°, 30°, 35° or 40°.

Figure 8B:
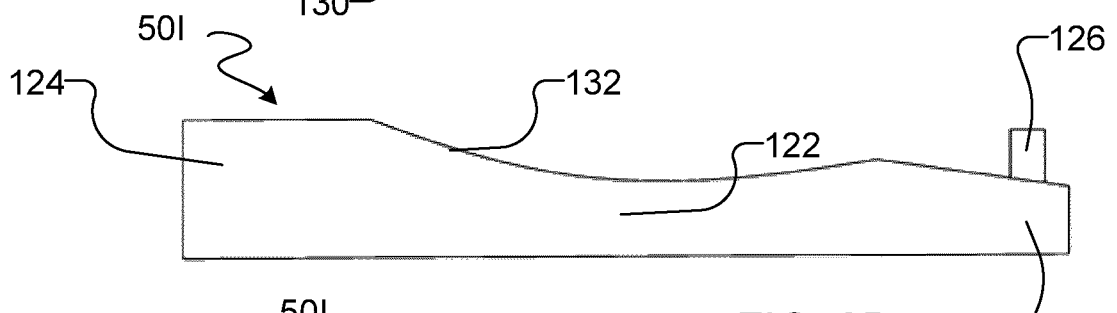
Figure 8C:
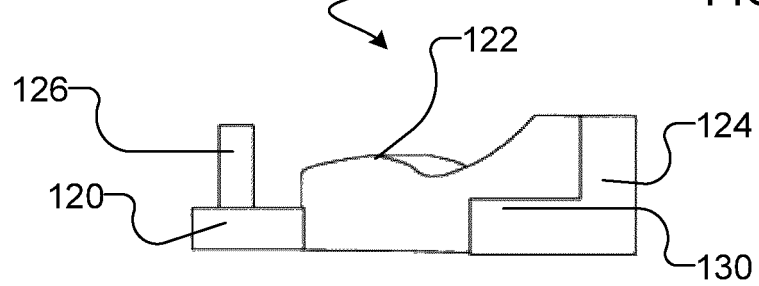
Figure 8D:
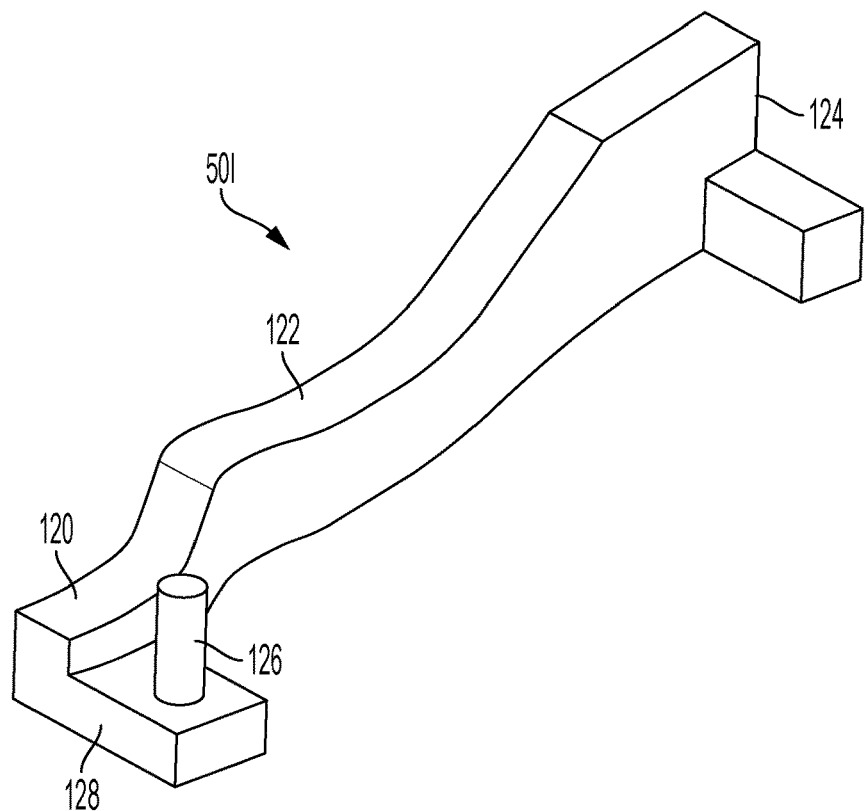
Figure 8E:
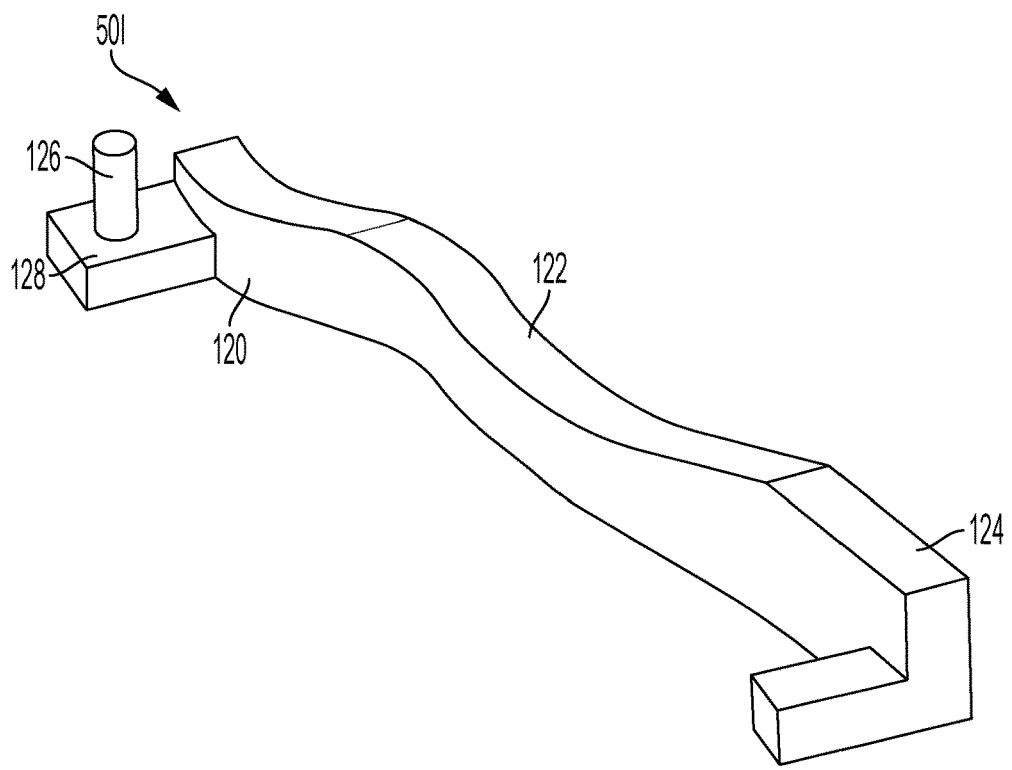

Also in the illustrated embodiment, as best seen in the side and perspective views of FIGS. 8B, 8D and 8E, an outer edge 132 of radial rod 50I is tapered inwardly from the distal end to the proximal end of radial rod 50I. In the illustrated embodiment, the outer edge 132 is generally straight along distal end 124, is arcuately curved slightly inwardly through middle portion 122, and tapers gently inwardly in the proximal direction at proximal end 120, for example at an angle in the range of 2° to 15° including any value therebetween, e.g. 3°, 4°, 5°, 6°, 7°, 8°, 9°, 10°, 11°, 12°, 13° or 14°.

In the illustrated embodiment, proximal end 120 of radial rod 50I is provided with a projection 126 that is shaped and configured to be rotatably engageable with either one of apertures 112A/112B provided in volar rod 50H. In the illustrated embodiment, projection 126 is provided on a lateral extension 128 that projects laterally from the proximal end 120 of radial rod 50I.

In some embodiments, radial rod 50I is rotatably engageable with volar rod 50H with a tight fit, meaning that while relative rotation of rods 50I and 50H can be achieved by the application of a moderate degree of force by a user, rods 50I and 50H inherently resist rotational movement of projection 126 within apertures 112A/112B unless a sufficient force is applied. That is, the tolerance between projection 126 and apertures 112A/112B is such that a sufficient degree of friction is present that rods 50I and 50H will only rotate relative to one another when a reasonable amount of force, e.g. 10-50 N or any value therebetween, e.g. 15, 20, 25, 30, 35, 40 or 45 N, is applied by a user.

Radial rod 50I is also provided with a laterally extending projection 130 at its distal portion 124. Without being bound by theory, laterally extending projection 130 can be used to help prevent or minimize rotation of radial rod 50I when inserted in a fracture cavity. Laterally extending projection 130 is thus an example of a surface feature that stabilizes an implant, in this case radial rod 50I, when the implant is inserted in a fracture cavity.

In one example embodiment and by way of example only, in some embodiments, projection 126 has a radius of approximately 1.25 mm, rod 50I has a maximum depth of about 5 mm at the distal portion 124 thereof, a thickness of about 2 mm, an overall axial height of about 32 mm, an overall width of about 16 mm, lateral extension 128 has an axial height of about 3 mm, and laterally extending projection 130 extends about 6 mm.

Figure 23:
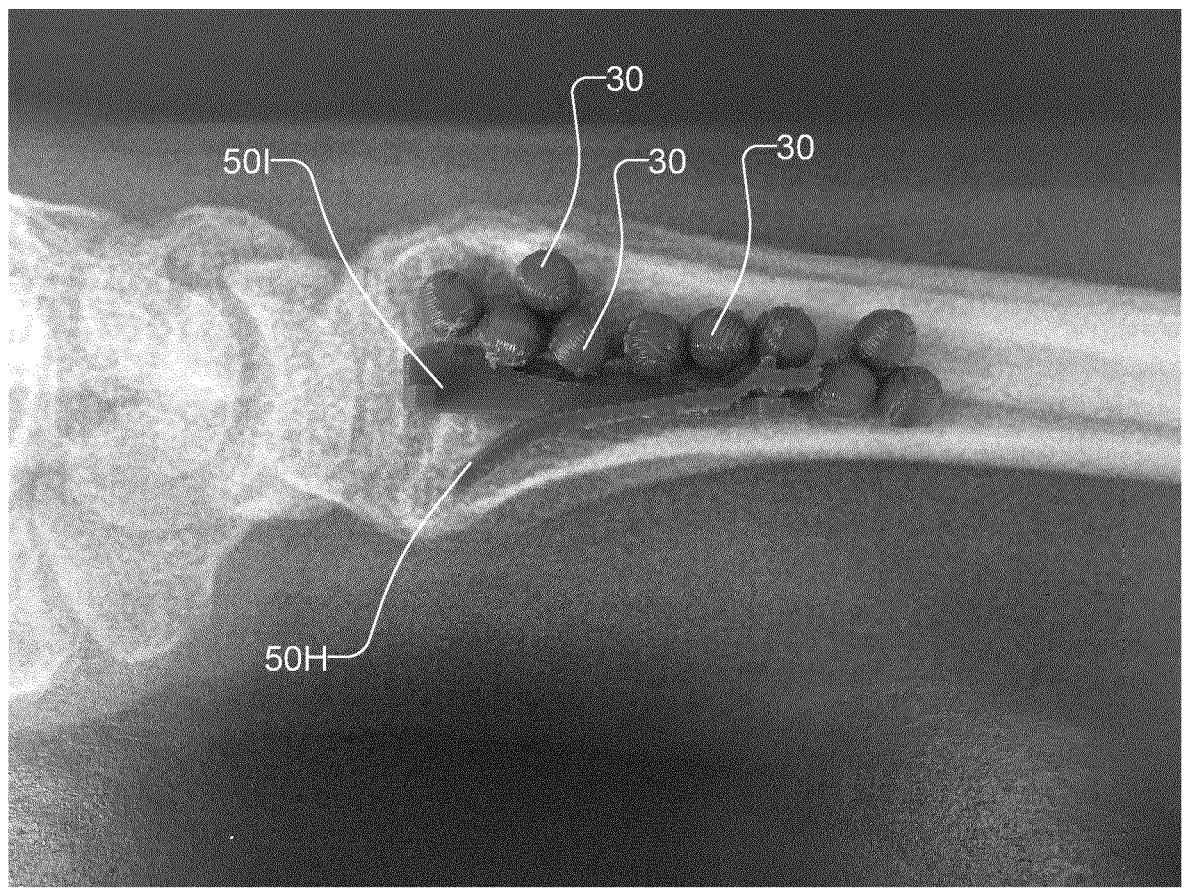
FIG. 23 is an image of exemplary embodiments of rods and spheres positioned on a lateral X-ray image of a fracture of the distal radius.
Figure 24:
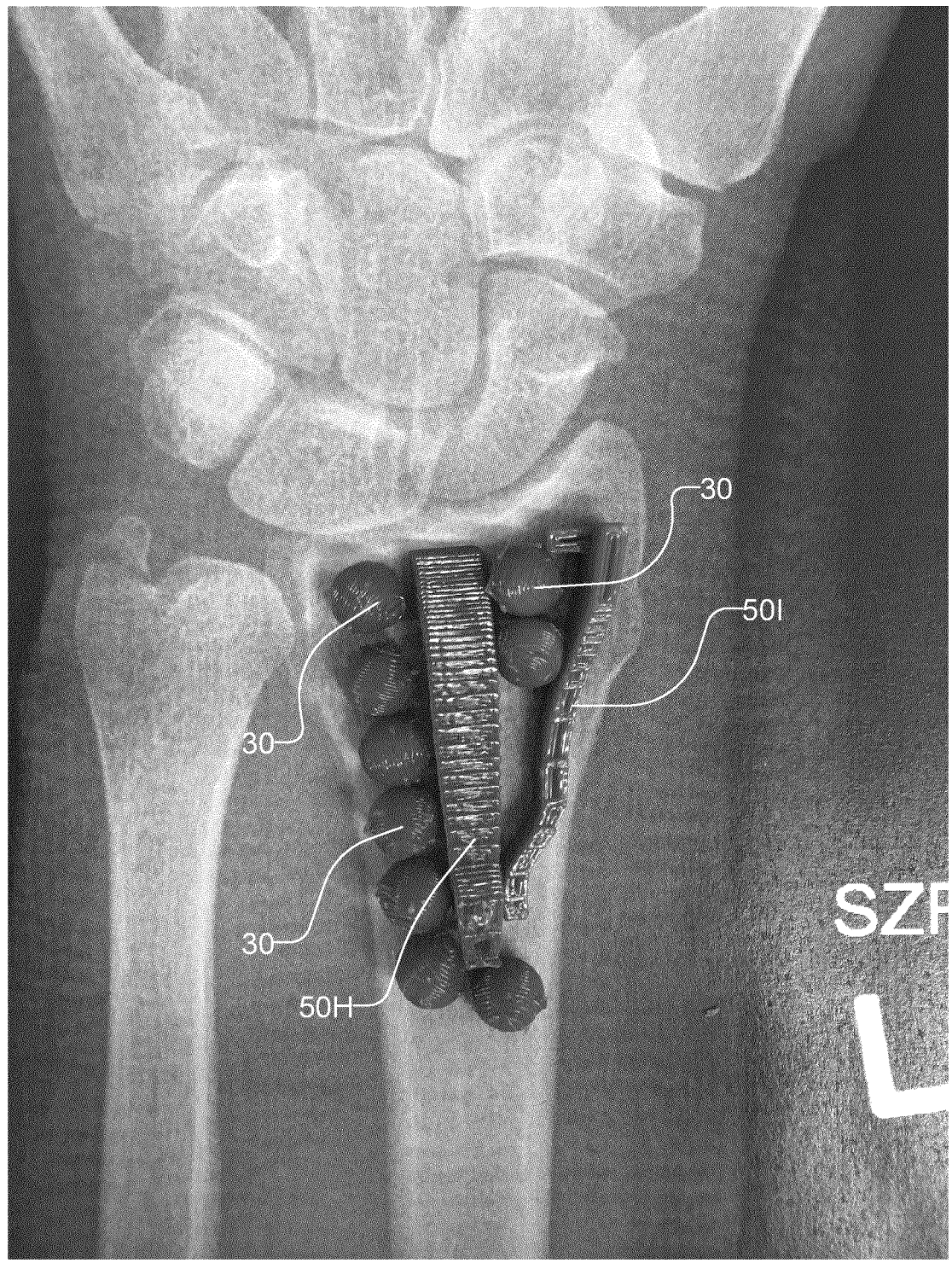
FIG. 24 is an image of exemplary embodiments of rods and spheres positioned on a posterioranterior X-ray image of a fracture of the distal radius.

Volar rod 50H and radial rod 50I are shaped to conform to the volar and radial aspects of the inner walls of the distal radius, and to be positioned generally orthogonally to one another in use, e.g. as shown in FIGS. 23 and 24. Providing a structural linkage between the volar rod and the radial rod in this fashion enhances the stability of the implant when positioned within the fracture cavity. Without being bound by theory, this may reduce movement of the orthobiologic inserts when in use, facilitating fracture healing.

Figure 9A:
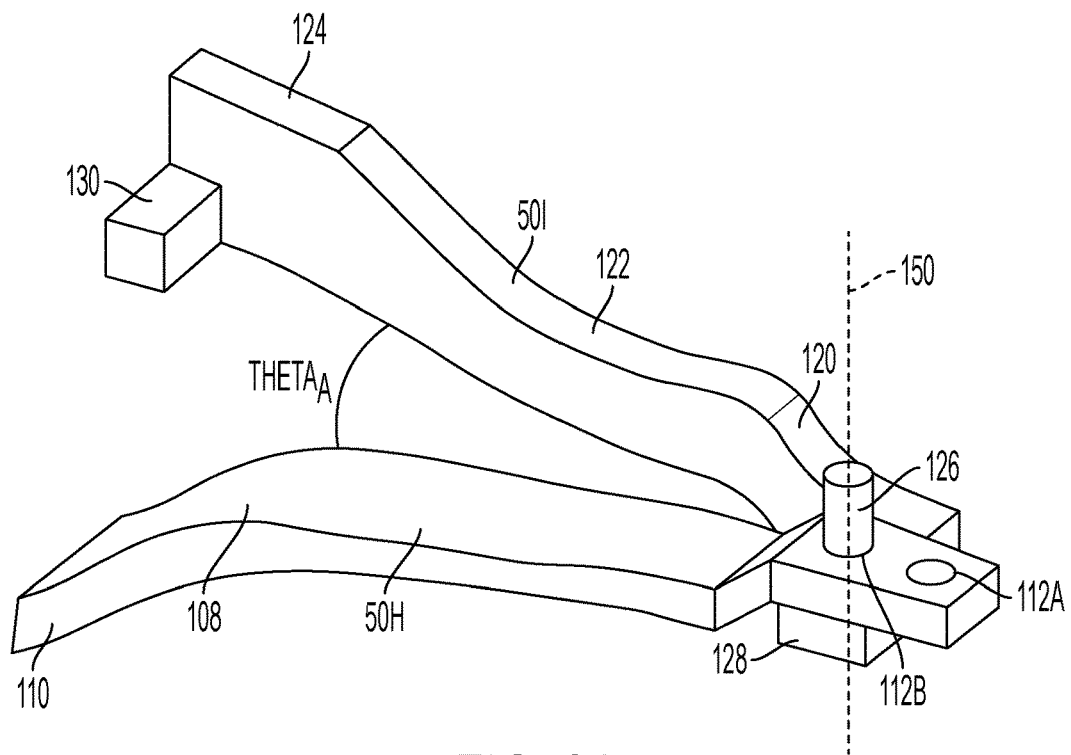
FIGS. 9A and 9B show perspective views of example embodiments of volar and radial rods for use in the stabilization of fractures that are coupled together so as to permit relative rotation of the two rods.
Figure 9B:
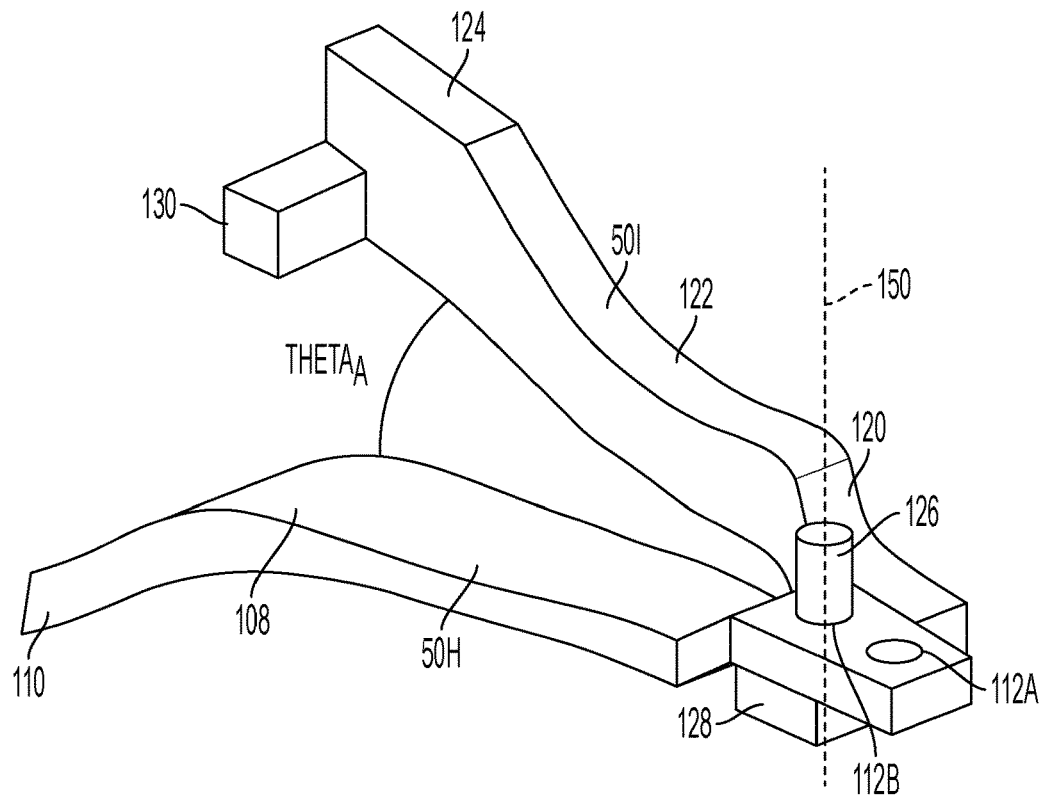

FIGS. 9A and 9B show an example embodiment of a volar rod 50H and a radial rod 50I that have been linked together via aperture 112B of volar rod 50H and projection 126 of radial rod 50I. Linked rods 50H and 50I are rotatable relative to one another about a central axis 150 that extends axially through projection 126. An angle $THETA_A$ is defined between rods 50H and 50I. Rods 50H and 50I are rotatable relative to one another to reduce angle $THETA_A$ to a minimum value in an insertion configuration in which rods 50H and 50I extend generally parallel to one another (to allow for ease of insertion into a fracture cavity), i.e. define a construct having a relatively narrow diameter, and to increase angle $THETA_A$ so that rods 50H and 50I extend generally orthogonally to one another in a deployed configuration, i.e. to define a construct having a diameter that is larger than the relatively narrow diameter of the insertion configuration.

In one example embodiment, the shape of the implants, such as rods 50H and 50I, is optimized by a repeated fit process in a model of a particular fracture cavity. For example, the shape of any given fracture cavity can be simulated in a cadaver specimen and/or in a plastic model of the fracture cavity. One or more than one implant can be inserted into the model fracture cavity, and the fit and stability of the implant(s) within the fracture cavity can be assessed. Based on the shape of the implant relative to the shape of the fracture cavity, structural changes can be made to the shape of the implant to ensure that the implant better conforms with the shape of the peripheral cortical bone against which it is intended to lie in the fracture cavity. For example, the angle, shape, configuration or width of the implant can be modified to optimize the shape of the implant to sit in place against the peripheral cortical bone against which it is intended to lie with a minimum degree of movement once the implant is in its desired location. If the implant is prone to moving in a particular manner, for example rotating out of a desired alignment, a structural feature (e.g. projection 130) can be added to the implant to prevent or minimize the likelihood that the implant will move in that particular undesired manner.

The repeated fit process in the model of a particular fracture cavity can be tested by making a series of models of proposed implants using an additive manufacturing technique such as 3D printing, testing the fit of those implants within the fracture cavity, and then revising the shape of the implants (for example by altering the angle, shape, configuration or width of the implant, or adding structural features to minimize motion of the implant within the fracture cavity) to optimize fit and stability within the fracture cavity. In some embodiments, the implants can be provided with structural features for coupling two or more implants together, to enhance the stability of the coupled implants within the fracture cavity, and the repeated fit process can be carried out using the two or more implants to optimize the shape and configuration of the two or more implants and the structural features for coupling the implants together. Similar principles can be applied to revise the shape and coupling mechanism to optimize fit and stability of the coupled implants within the fracture cavity by repeatedly testing the fit of the coupled implants within the model fracture cavity. While an example embodiment has been described herein in which rods 50H and 50I have been optimized for stability in fractures of the distal radius, the principles described herein are generally applicable to produce implants having shapes, configurations and engagement mechanisms optimized for use in other types of fractures.

In some embodiments, a set comprising a plurality of rods having two or more of the aforementioned configurations is provided. In one example embodiment, a plurality of short straight rods and a plurality of long curved and/or angled rods having one or more different angles of curvature are provided. In use, in some embodiments appropriate long curved rods having an appropriate degree of curvature to approximately match the conformation of the region of bone against which the long curved rod is to be implanted can be selected for use to line the periphery of a fracture cavity.

In use, in some embodiments, a plurality of short straight rods can be used to line the periphery of a fracture cavity, to avoid a need to select rods having an appropriate degree of curvature, and to avoid a need to position each rod in a specific location within the fracture cavity.

In some embodiments, rod 50 is porous. In some embodiments, rod 50 is microporous. In some embodiments, the pores in rod 50 have an average diameter on the order of 1 µm to about 100 µm or any value therebetween, including for example 5, 10, 15, 20, 25, 30, 35, 40, 45, 50, 55, 60, 65, 70, 75, 80, 85, 90 or 95 µm.

In some embodiments, the surface of the rods 50 has a rough finish or texture, as distinguished from a smooth or highly polished surface. In some embodiments, the rough finish of the surface of rods 50 arises as a result of the porous nature of the material used to form the rod. In some embodiments, surface treatments could be applied to provide a rough texture to the surface of rod 50. For example, in some embodiments, an implant such as rod 50 could be produced in a mold, and then the surface of the implant could be polished or slightly roughened in order to alter the texture of the surface of the implant.

Without being bound by theory, embodiments of the rods that have a rough finish or texture on the outer surface of the rod may minimize sliding of the implants once inserted into a fracture cavity, which may increase overall fracture stability.

In some embodiments, the rods are made from an orthobiologic material. In some embodiments, the rods are made from a non-resorbable material, e.g. biocompatible metal.

In use, rods such as rod 50 can be used to line the inner cortical wall (circumference) of the bone fracture, bridging the unstable zones, for example on the volar and dorsal aspects of a fracture. In some embodiments, hollow perforated orthobiologic spheres such as sphere 20 can be used to fill the cavity of the void in the bone fracture. In some embodiments, a plurality of rods 50 and spheres 20 are used together to stabilize a bone fracture.

As an example of how rods 50 and spheres 20 can be used together to stabilize a bone fracture, with reference to a fracture of the distal radius, in some embodiments, orthobiologic rods such as rods 50 are used to line the inner wall (circumference) of the distal radius, bridging unstable zones, especially, but not exclusively, on the radial and dorsal aspects. In some such embodiments, perforated hollow orthobiologic spheres such as spheres 20 are used to fill the remainder of the metaphyseal marrow cavity. Without being bound by theory, it is believed that the use of the rods is better to stabilize the circumference of the bone fracture, while use of porous hollow spheres to fill the rest of the fracture volume allows the natural processes of bone formation to proceed as efficiently as possible.

Figure 10:
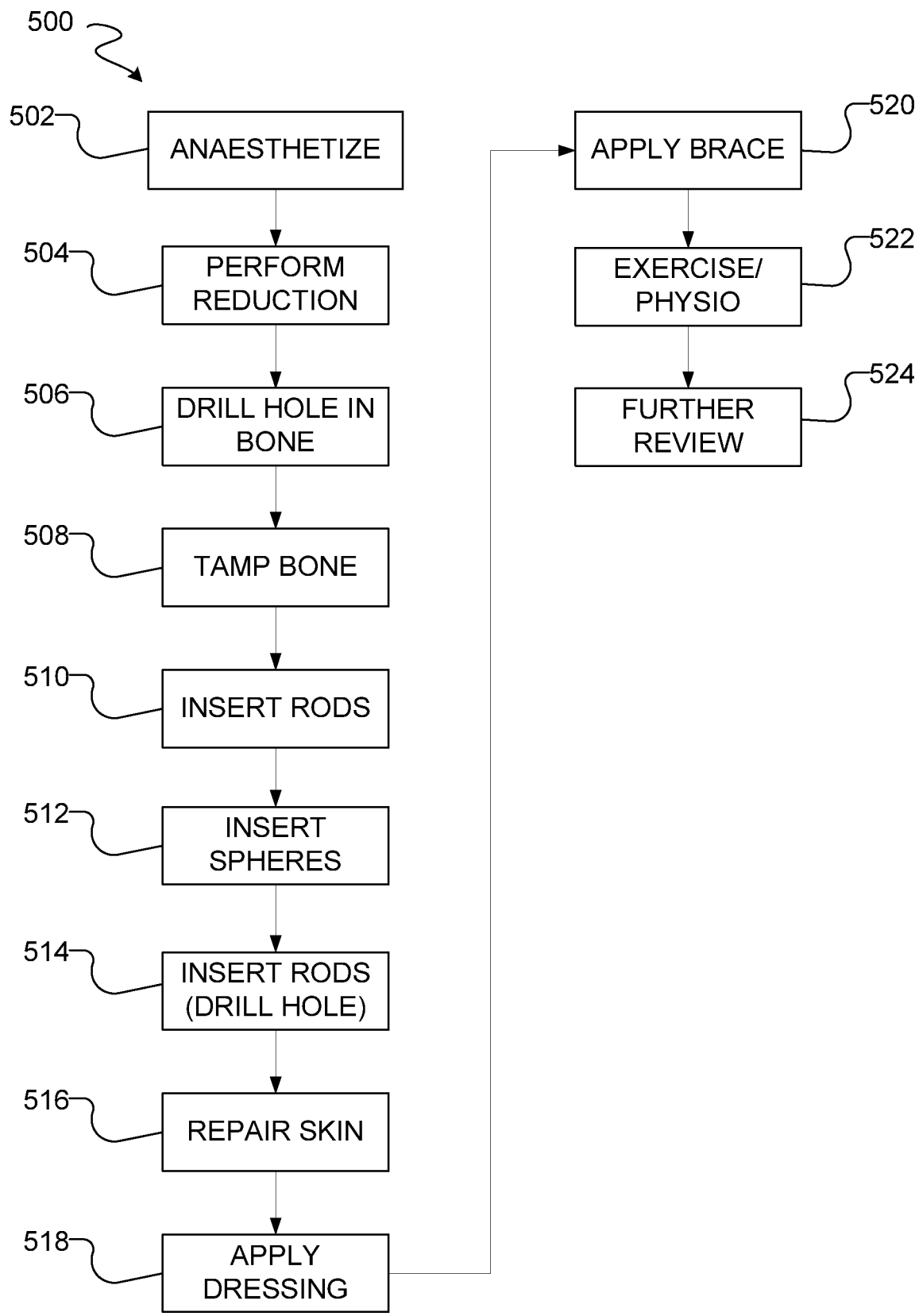
FIG. 10 is an example embodiment of a process for stabilizing a fracture using rods and spheres according to some exemplary embodiments.

In one example embodiment illustrated in FIG. 10, a process 500 for stabilizing a bone fracture is provided. First at 502, the area in which the fracture has been sustained is rendered anaesthetic by one or more anaesthethic techniques, e.g. freezing, as would be done for example in most cases where a broken bone requires reduction. Local anaesthesia is administered to the skin and soft tissues, and in some embodiments a supplemental vasoconstrictor such as epinephrine is also administered. At 504, reduction is then performed to restore the bone to approximately its original configuration. In some embodiments, fluoroscopy is used to confirm a satisfactory reduction. An incision is made in the skin and, in some embodiments, at 506 a small unicortical hole (for example, having a diameter of about 6.5 to 8.5 mm in some example embodiments) is drilled through the bone to facilitate insertion of orthobiologic rods and spheres according to example embodiments, for example rods 50 and spheres 20. Alternatively, in some embodiments, a slightly oblong hole (axial diameter longer than the transverse diameter) can be made by using K-wires (e.g. 0.045 inch) to perforate the bone along the perimeter of the oblong hole. The oblong piece of bone can be replaced at the end of the procedure, and turned slightly in order to lock it into position.

At 508, bone is tamped in any suitable manner (for example using a curved trumpet or tamp, for example a 6.5 mm curved tamp), to expand the fracture cavity within the bone for receiving the orthobiologic rods and/or spheres. In some embodiments, tamping reduces any intra-articular step deformity and reinforces the subchondral region with metaphyseal bone to prepare the fracture cavity to receive a plurality of orthobiologic implants. In some embodiments, radial and volar seating chisels are used to prepare the intramedullary bone slots for the radial and volar rods.

After the fracture cavity has been prepared, at 510 the desired number of orthobiologic rods are inserted within the cavity. In one example embodiment, the orthobiologic rods are aligned axially around the periphery of the cavity, to provide axial/peripheral stability to the fracture. In one example embodiment, a radial rod such as rod 50I is inserted first into the cavity, then a volar rod such as rod 50H is inserted into the fracture cavity, and the two rods are linked together by engaging the projection 126 of the radial rod 50I with a suitable one of the apertures 112A/112B on the volar rod. In alternative embodiments, a radial rod such as rod 50I is first engaged via its projection 126 to volar rod 50H via a suitable one of the apertures 112A/112B, and then the coupled radial rod and volar rod are inserted together into the fracture cavity. For example, in the illustrated embodiment, when volar rod 50H is engaged with radial rod 50I via projection 126 and apertures 112A or 112B, volar rod 50H and radial rod 50I are rotatable relative to one another, but are otherwise prevented from moving relative to one another. This allows volar rod 50H and radial rod 50I to be rotated into an insertion configuration so that the two rods are in generally parallel alignment, so that the assembly of volar rod 50H and radial rod 50I has a relatively narrow diameter, allowing for ready insertion into the fracture cavity. After insertion, volar rod 50H and radial rod 50I can be rotated relative to one another to a deployed configuration in which volar rod 50H and radial rod 50I extend generally orthogonally to one another, thereby minimizing the movement of the rod assembly within the fracture cavity.

In some embodiments, at 512 a plurality of orthobiologic spheres are inserted to fill the cavity. In some embodiments, at 514 one or more additional orthobiologic rods are inserted adjacent to the drill hole to provide a mechanical barrier to blood, marrow content, and sphere extrusion from within the intramedullary canal of the bone. Light pressure is maintained over the drill hole until the drill hole is dry. In some embodiments, a topical hemostatic agent is used to accelerate this process.

At 516, the skin is repaired to close the incision, and a light compressive dressing is applied at 518. A lightweight removable brace, that is optionally adjustable, is applied to the patient if appropriate for the location of the fracture at 520. In some embodiments, a bulky compression bandage is used instead of a removable brace. The patient can be prescribed an appropriate exercise program at 522, for example for the fingers and thumb, elbows and shoulder in the case of a radial fracture, to be conducted while wearing the brace or bandage, if appropriate. The patient can be further assessed clinically and/or radiographically at one or more subsequent intervals at 524 to assess recovery of the patient and healing of the fracture, respectively. Once the fracture has stabilized sufficiently (for example, one to four weeks after the fracture), active exercises to resume motion (e.g. wrist motion in the case of a fracture of the distal radius) can be initiated, if appropriate.

At the step of inserting the rods, in some example embodiments, a plurality of long curved and/or angled rods are introduced into the fracture cavity and are aligned axially around the periphery of the cavity. Each one of the long curved and/or angled rods is selected and positioned to have a degree of curvature or angle that approximately matches the conformation of the region of bone against which that particular rod is to be positioned.

In some example embodiments, a plurality of short, straight rods are used to line the periphery of the fracture cavity. Some such embodiments may provide a lesser degree of complexity for the practitioner (e.g. surgeon) than embodiments utilizing a plurality of long curved rods, as there may be situations where there is no need for the practitioner to select rods having a specific degree of curvature, or determine which rod should be placed at each particular location around the periphery of the fracture cavity in order to achieve stable facture fixation.

In some example embodiments, a combination of a plurality of long curved and/or angled rods and long straight or short straight rods could be used to line the periphery of the fracture cavity. Each one of the long curved and/or angled rods could be positioned to be adjacent to a region of bone having a degree of curvature or angle that generally matches the degree of curvature or angle of the rod. The spaces between each one of the so-positioned long curved and/or angled rods could be filled by inserting a plurality of straight (short straight or long straight) rods and aligning the straight rods axially with the curved and/or angled rods to line the periphery of the fracture cavity.

With reference to FIGS. 11 to 21, an example embodiment of a method for stabilizing a fracture of the distal radius is described in greater detail. The measurements written on the figures are by way of example only to illustrate possible dimensions of the fracture cavity, and are not limiting. Furthermore, one skilled in the art would be able to adapt the process for use in similar fractures, and the exemplary method is not limited to fractures of the distal radius.

Figure 11:
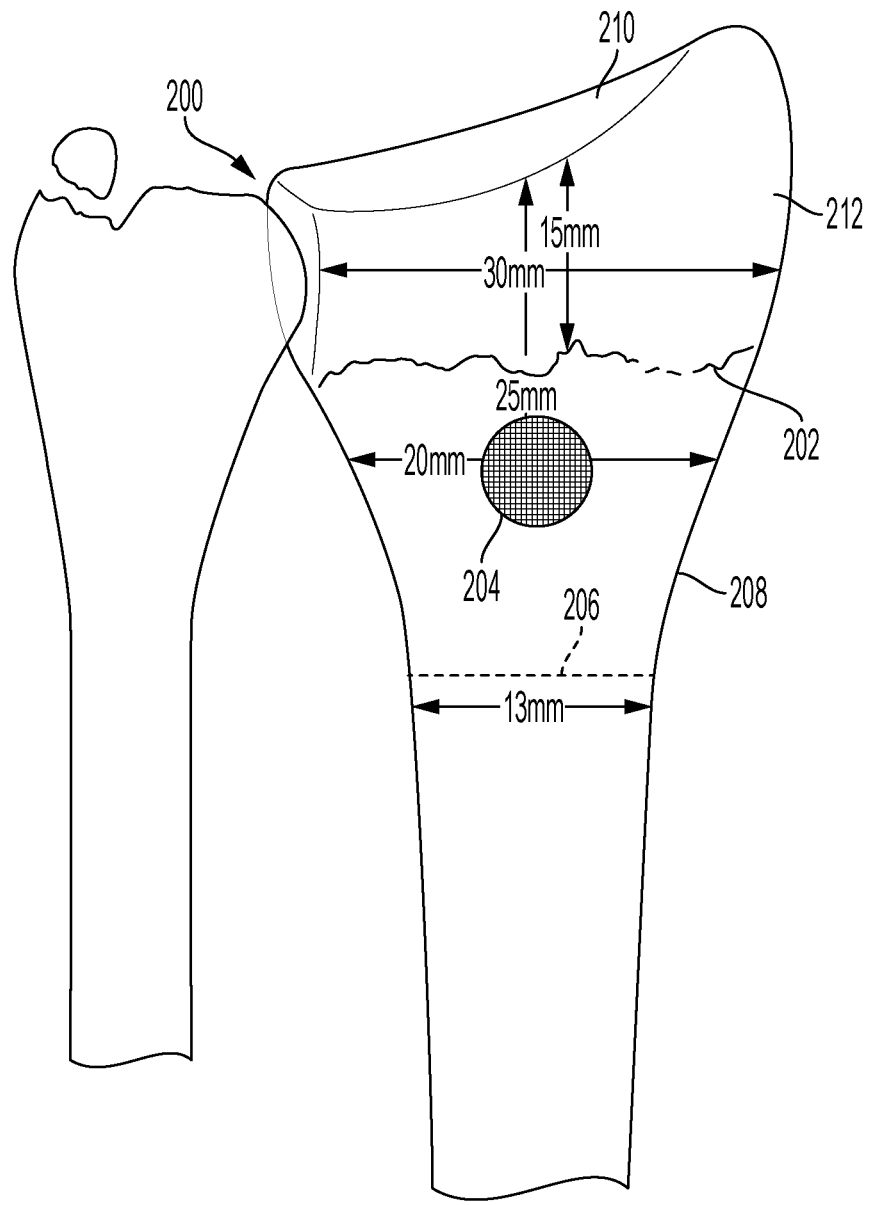
FIG. 11 is a sketch of a posterior-anterior view of a fractured distal radius illustrating the approximate position of a drill hole (proximal to the fracture) in a method of stabilizing a bone fracture according to one example embodiment.

FIG. 11 shows a distal radius 200 having a fracture line 202. After closed reduction of the fracture, a drill hole 204 is made in the bone intentionally proximal to the fracture site to avoid disturbance of the fracture soft tissue envelope, although in some embodiments the drill hole 204 can be made at the fracture site, to facilitate insertion of orthobiologic rods and spheres to fill the fracture cavity. Drill hole 204 may have any suitable diameter that is sufficiently large to allow insertion of tools and implants within bone, without being overly large. In some example embodiments, drill hole 204 has a diameter in the range of about 6 to about 10 mm, including any value therebetween, e.g. 6.5 mm, 7.0 mm, 7.5 mm, 8.0 mm, 8.5 mm, 9.0 mm or 9.5 mm.

Bone is tamped or otherwise prepared within the fracture void to expand the fracture cavity 212 that will be filled with orthobiologic rods and spheres. In some embodiments, bone is tamped to reduce any intra-articular step deformity and/or to reinforce the subchondral region with metaphyseal bone. In the illustrated embodiment, bone is tamped using a curved trumpet or tamp within the fracture cavity down to approximately the point indicated by line 206, which forms the base of the fracture cavity. Proximal to this point, further canal preparation is unnecessary. The fracture cavity 212 is thus defined between the inside surface of the peripheral edges 208 of the bone 200, base 206, and the upper surface of the distal radius 210.

Figure 12:
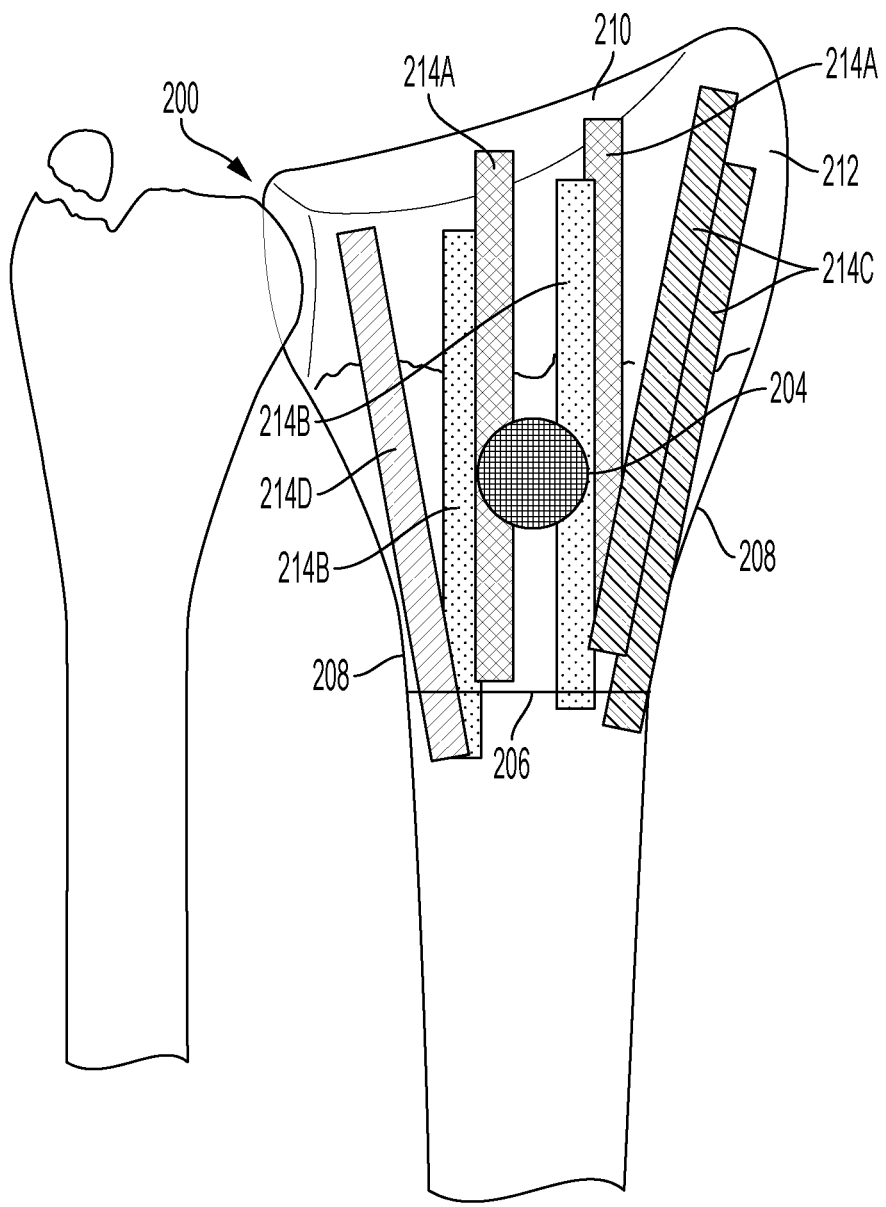
FIG. 12 is a sketch of a posterior-anterior view of the fractured distal radius of FIG. 11, illustrating schematically the insertion of a plurality of rods according to an example embodiment within the fracture cavity.

FIG. 12 is the same view as FIG. 11, illustrating schematically the insertion of a plurality of orthobiologic rods 214A, 214B, 214C and 214D, collectively referred to as rods 214 (which could be, for example, rods 50), within the fracture cavity. The orthobiologic rods 214 are inserted through the drill hole 204, and are aligned approximately axially around the periphery of the fracture cavity 212 using any suitable instrument, for example, a pair of forceps. Orthobiologic rods 214 extend generally axially within the fracture cavity (i.e. the height of rods 214 extends in approximately the same direction as the length of bone 200).

Orthobiologic rods 214A are dorsal rods (i.e. are located dorsally). Dorsal rods 214A are long rods, and are generally straighter along their longitudinal axes than rods designed for insertion adjacent the volar surface (i.e. volar rods 214B). In some embodiments, dorsal rods 214A have an angle or curvature of approximately 10 to 20 degrees. Orthobiologic rods 214B are volar rods (i.e. are located volarly), and are provided with a significant curvature away from their longitudinal axes, which enables the volar rods to conform to the flare of the distal radius. In some embodiments, orthobiologic rods 214B are provided with an elbow having a bend or one or more angled regions providing a total angle in the range of about 15 to 30 degrees. Orthobiologic rods 214C are radial rods (i.e. are located radially), and are provided with a slight bend away from their longitudinal axes, which enables the radial rods to conform to the mild flare of the distal radius. In some embodiments, orthobiologic rods 214C are provided with an elbow having a bend in the range of about 5 to 15 degrees. Orthobiologic rod 214D is an ulnar rod (i.e. is positioned ulnarly). Orthobiologic rod 214D is provided with a slight bend away from its longitudinal axis, which enables the ulnar rods to conform to the slight bend of the ulnar region of the distal radius. In some embodiments, orthobiologic rod 214D is provided with an elbow having a bend in the range of about 10 to 20 degrees.

Figure 13:
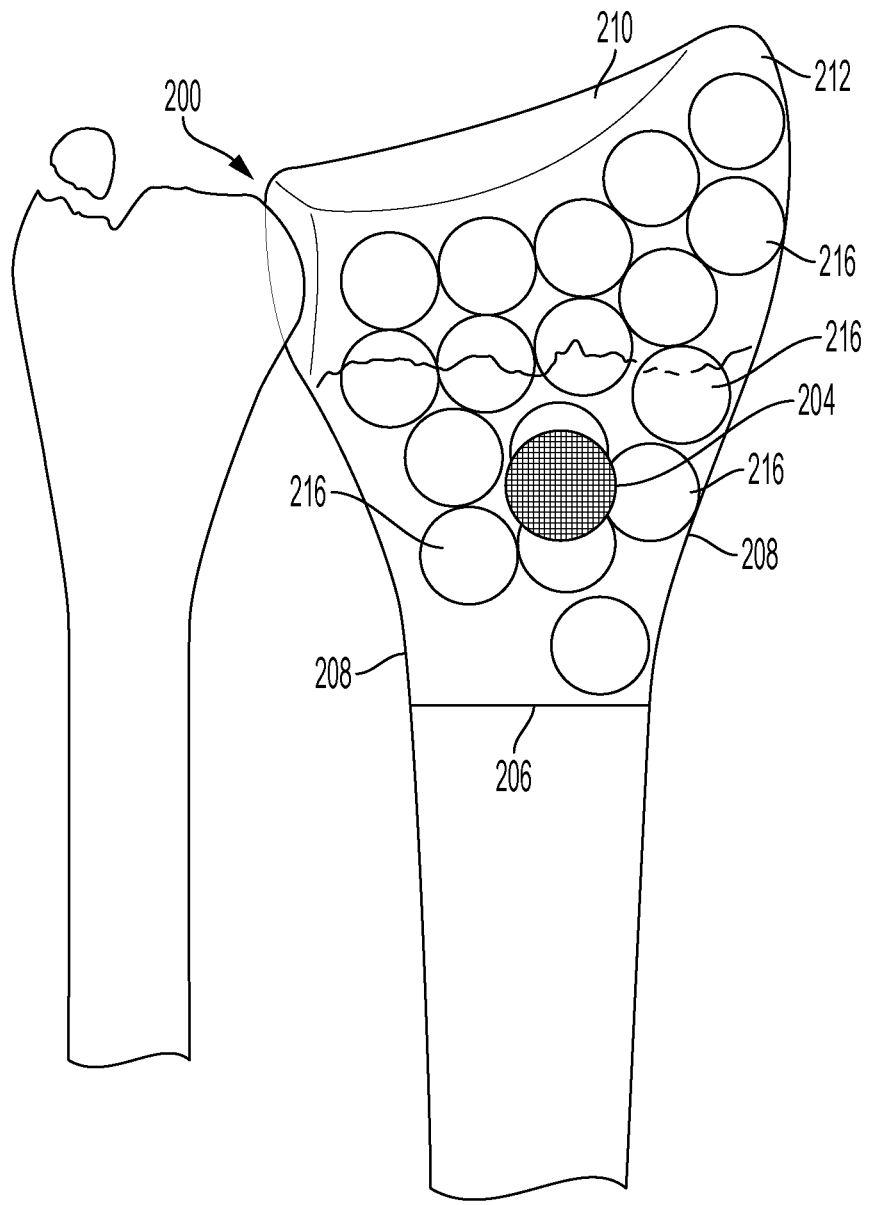
FIG. 13 is a sketch of a posterior-anterior view of the fractured distal radius of FIG. 11, illustrating schematically the insertion of a plurality of perforated hollow orthobiologic spheres according to an example embodiment within the fracture cavity.

FIG. 13 is the same view as FIG. 11, illustrating schematically the insertion of a plurality of perforated hollow orthobiologic spheres 216 (which could be, for example, spheres 20) within the fracture cavity. Orthobiologic rods 214 have been omitted from FIG. 13 for clarity but are shown in FIG. 14.

Figure 14:
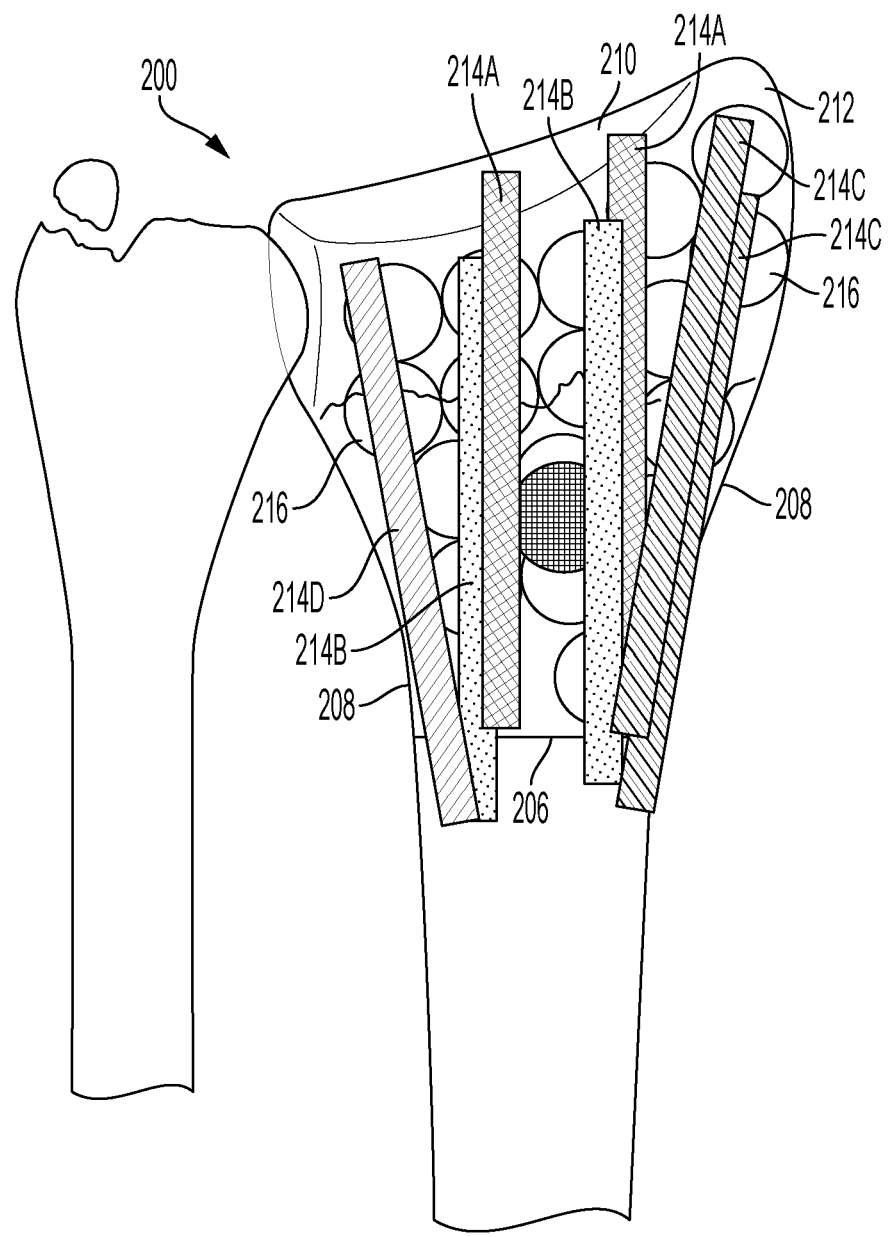
FIG. 14 is a sketch of a posterior-anterior view of the fractured distal radius of FIG. 11, illustrating schematically both the rods shown in FIG. 12 and the orthobiologic spheres shown in FIG. 13.
Figure 15:
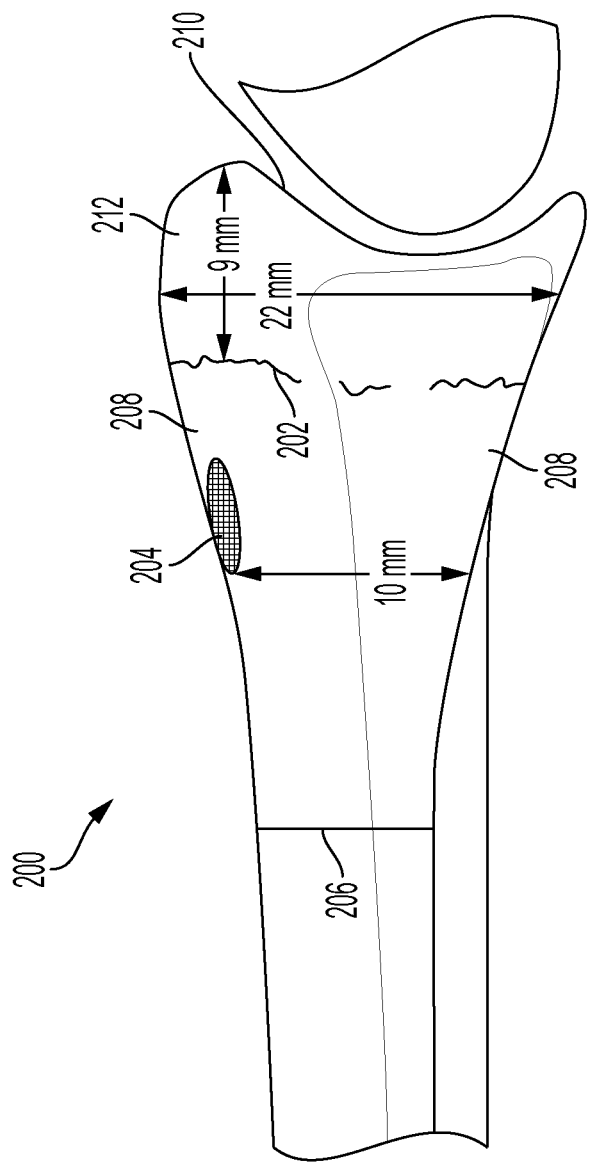
FIG. 15 is a sketch of a lateral view of the distal radial fracture of FIG. 11 along with the approximate position of a drill hole proximal to the fracture.
Figure 16:
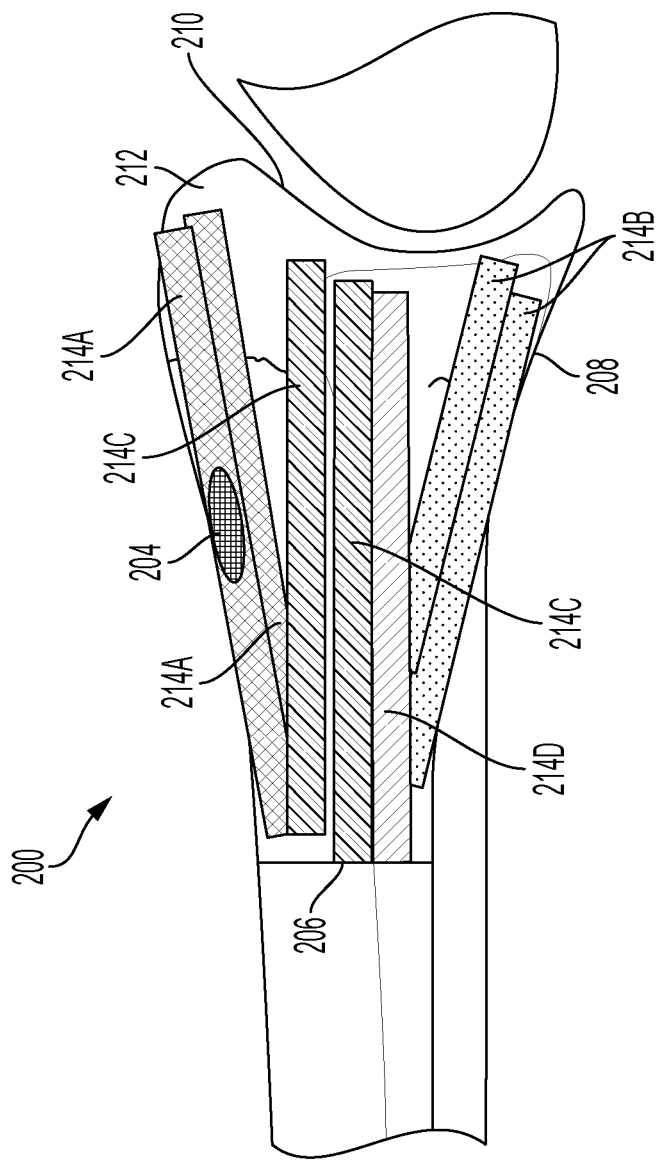
FIG. 16 is a sketch of a lateral view corresponding to FIG. 12.
Figure 17:
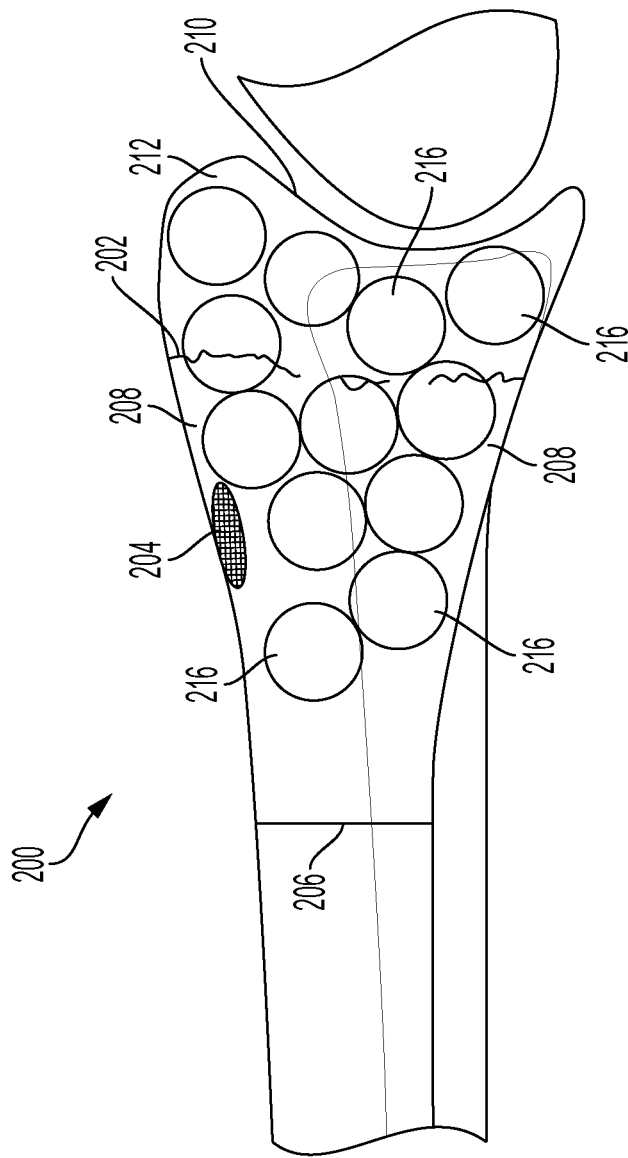
FIG. 17 is a sketch of a lateral view corresponding to FIG. 13.
Figure 18:
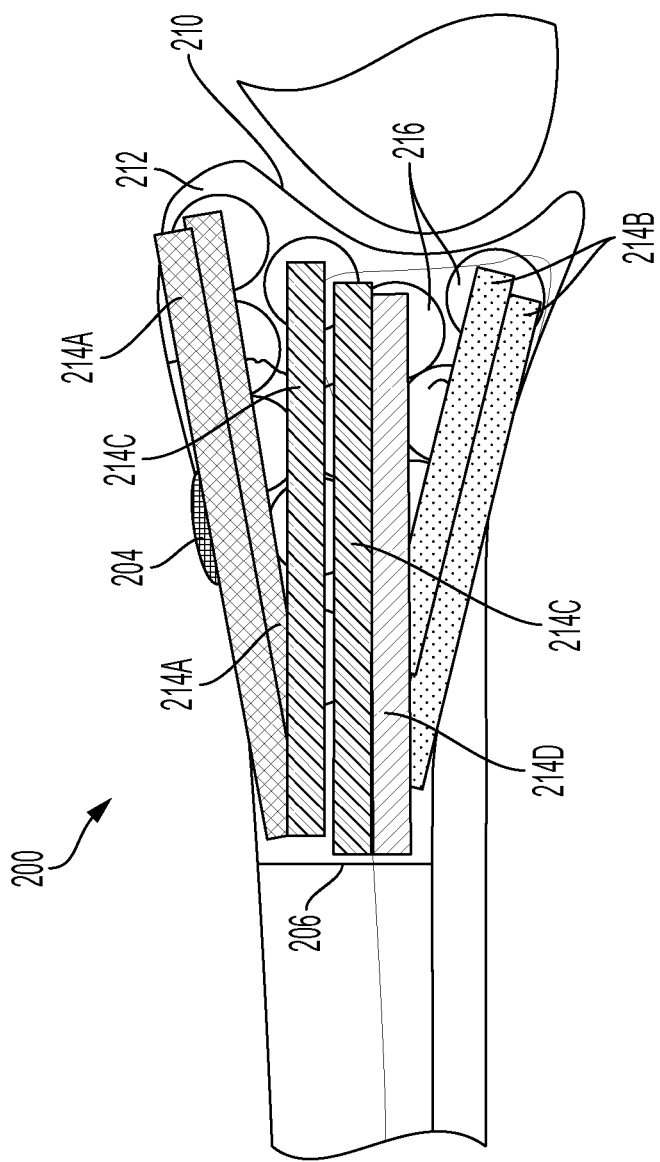
FIG. 18 is a sketch of a lateral view corresponding to FIG. 14.

FIG. 14 is the same view as FIG. 11, illustrating schematically the positioning of both the orthobiologic rods 214 of FIG. 12 and the perforated hollow orthobiologic spheres 216 of FIG. 13 within the fracture cavity.

FIGS. 15, 16, 17 and 18 are sketches of lateral views corresponding to FIGS. 11, 12, 13 and 14, respectively, wherein like features are shown with the same reference numerals.

Figure 19:
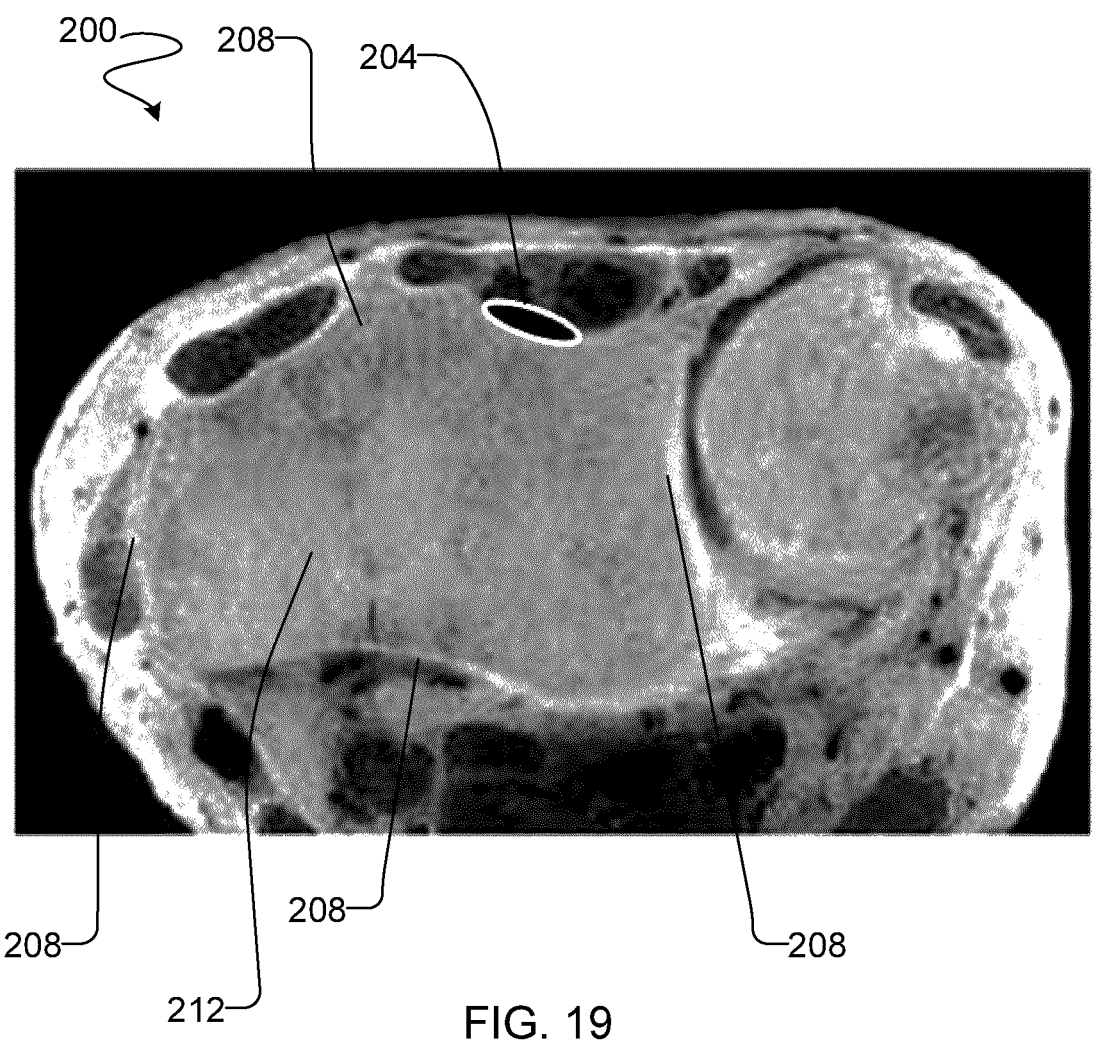
FIG. 19 is a transverse cross-sectional view of a distal radius looking down the long axis of the bone showing a potential dorsal location for an insertion hole to be drilled.
Figure 20:
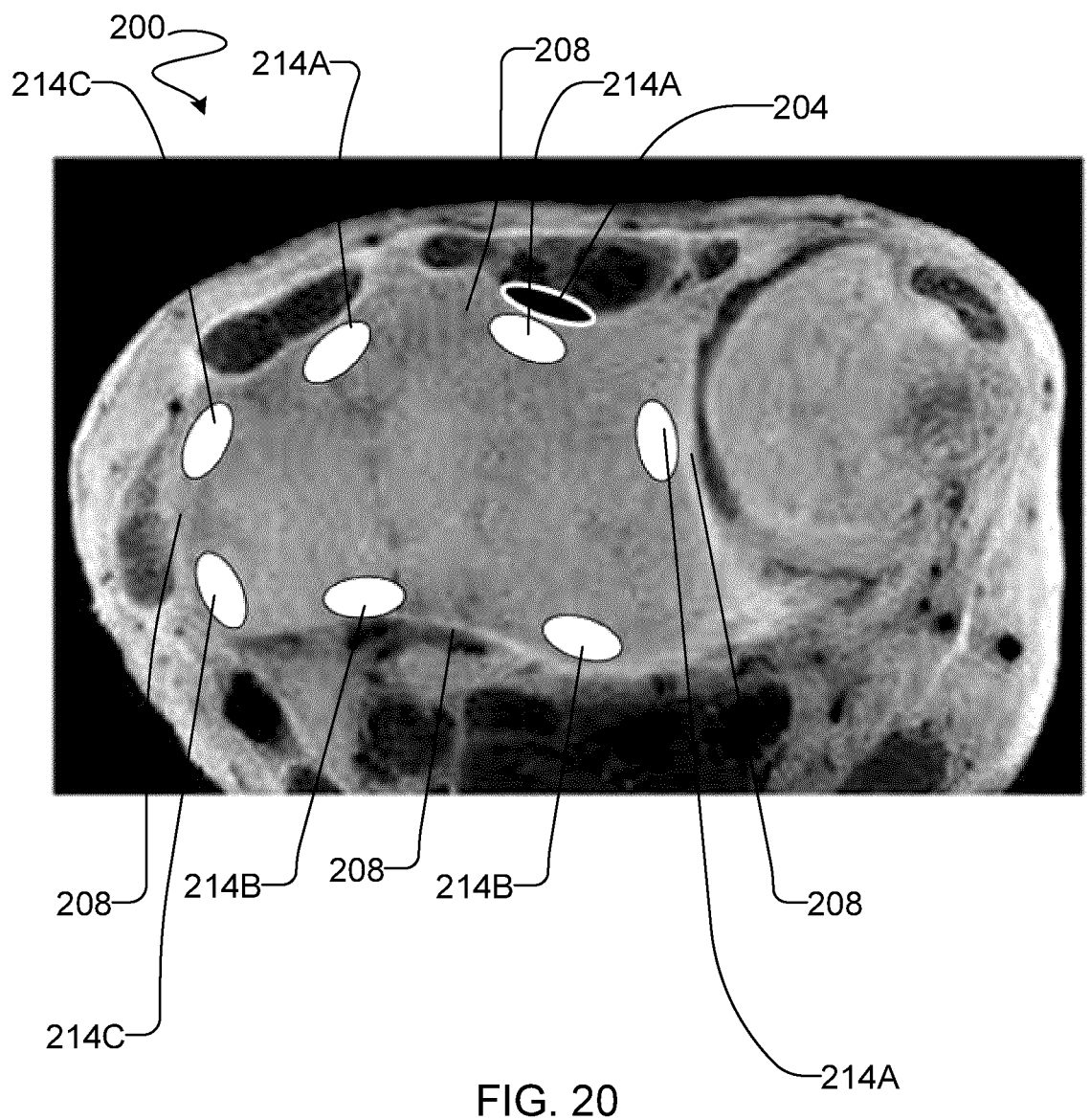
FIG. 20 is a transverse cross-sectional view of the image of FIG. 19 showing a schematic top view of the arrangement of a plurality of rods lining the inner cortical walls of the distal radius proximal and distal to the fracture, surrounding a hypothetical fracture void according to one example embodiment.
Figure 21:
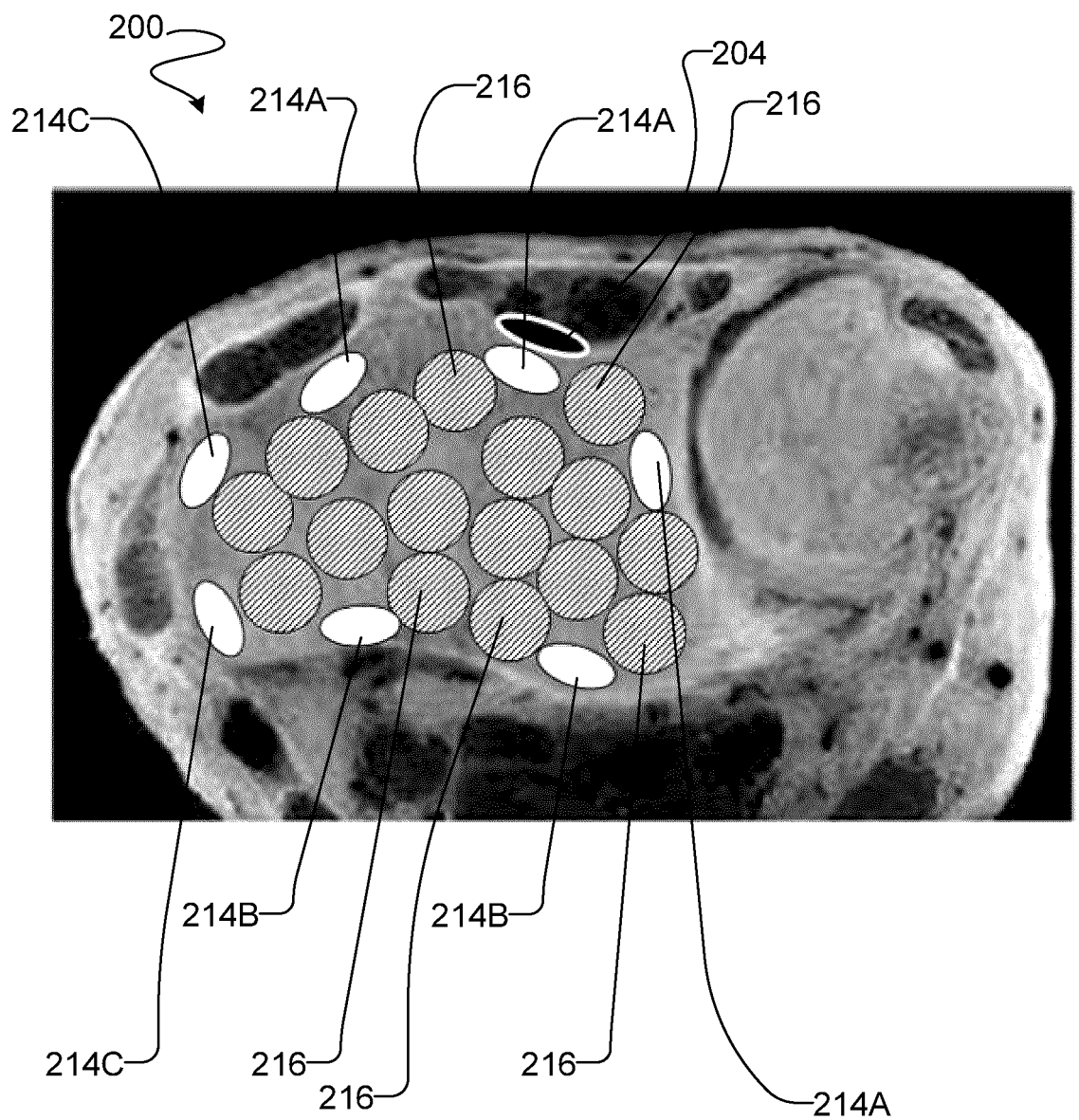
FIG. 21 is a transverse cross-sectional view of the image of FIG. 19 showing a schematic top view of the arrangement of a plurality of rods and perforated hollow orthobiologic spheres lining the inner cortical walls of the distal radius, and filling a hypothetical fracture void, respectively, proximal and distal to the fracture according to the example embodiment of FIG. 20.

FIGS. 19-21 illustrate schematically a transverse cross-sectional view looking down the longitudinal axis of the distal radius showing the placement of a plurality of orthobiologic rods and perforated hollow orthobiologic spheres within a fracture cavity of a hypothetical fracture. Features of FIGS. 19-21 that are the same as features previously described with reference to FIGS. 11-18 are shown with the same reference numeral.

FIG. 19 shows a transverse cross-sectional view of a distal radius 200. A fracture cavity 212 is defined between peripheral edges 208 of the bone. The approximate position of a dorsally located drill hole is illustrated schematically as 204.

As can be seen in FIG. 20, a plurality of orthobiologic rods 214A, 214B and 214C are positioned in approximately axial alignment around the peripheral edges 208 of the fracture cavity 212. Orthobiologic rods 214A, 214B and 214C extend generally longitudinally as peripherally as feasible within the bone medullary (i.e. fracture) cavity, so that the height of rods 214A, 214B and 214C is generally aligned with the longitudinal axis of distal radius 200.

As illustrated in FIG. 21, a plurality of hollow perforated orthobiologic spheres 216 fill the portions of fracture cavity 212 not filled by rods 214A, 214B and 214C.

Figure 22A:
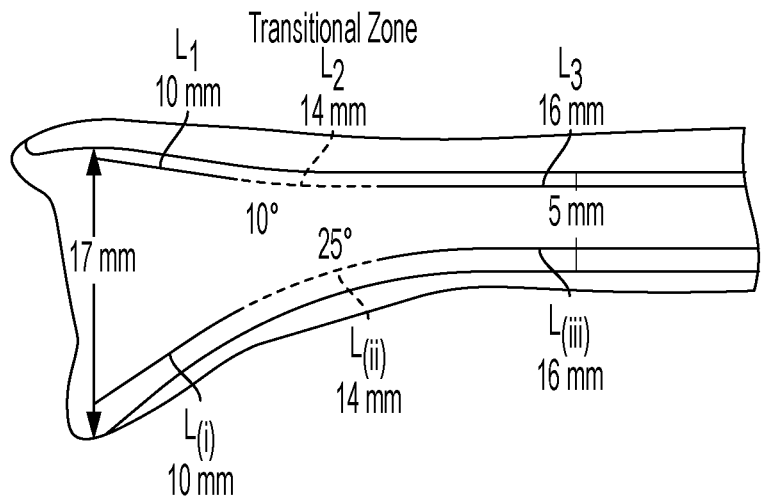
FIG. 22A is a sketch of a sagittal cross-sectional view of an example distal radius showing how the dimensions of rods can be configured to conform to the shape of the local peripheral cortical bone anatomy where the rod is to be implanted.
Figure 22B:
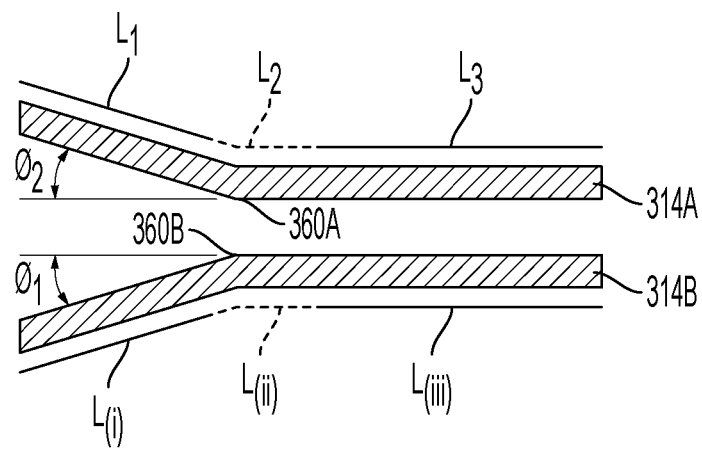
FIG. 22B is a sketch of a sagittal cross-sectional view of an example dorsal radius illustrating example embodiments of rods that are configured to conform to the shape of the local peripheral cortical bone anatomy of the regions illustrated in FIG. 22A.

With reference to FIGS. 22A and 22B, a further description of how a rod can be configured to conform to the local peripheral cortical bone of the location where the rod will be implanted in use is provided. FIG. 22A shows a sketch of a sagittal cross-sectional view of the distal radius. The dimensions presented on FIG. 22A are for the purposes of illustration only. In the illustrated embodiment, the hypothetical distal radius has a first portion having notional zones $L_1$, $L_2$ and $L_3$ of approximately 10 mm, 14 mm and 16 mm, respectively, with a transitional zone $L_2$ providing an angle of about 10° between zones $L_1$ and $L_3$; and a second portion having notional zones $L_{(i)}$, $L_{(ii)}$ and $L_{(iii)}$ of approximately 10 mm, 14 mm and 16 mm, respectively, with a transitional zone $L_{(ii)}$ providing an angle of about 25° between zones $L_{(i)}$ and $L_{(iii)}$.

With reference to FIG. 22B, orthobiologic rods 314A and 314B that are intended to be implanted against first portion $L_1$, $L_2$ and $L_3$ and second portion $L_{(i)}$, $L_{(ii)}$ and $L_{(iii)}$, respectively, are illustrated. Orthobiologic rod 314A is provided with a bent region 360A that provides an angle $\theta_2$ of approximately 10° between the portion of rod 314A that contacts region $L_3$ and the portion of rod 314A that contacts region $L_1$. In alternative embodiments, rod 314A could be provided with an angle $\theta_2$ of approximately 10-20°. Orthobiologic rod 314A is thus configured to generally match the shape of the region of bone in which it is intended to be implanted. Orthobiologic rod 314B is similarly configured to generally match the shape of the region of bone in which it is intended to be implanted, being provided with a bent region 360B that provides rod 314B with an angle $\theta_1$ of approximately 25° between the portion of rod 314B that contacts regions $L_{(i)}$ and the portion of rod 314B that contacts region $L_{(iii)}$. In alternative embodiments, rod 314B could be provided with an angle $\theta_1$ of approximately 15-30°.

In some embodiments, each of first portion $L_1$, $L_2$ and $L_3$ and second portion $L_{(i)}$, $L_{(ii)}$ and $L_{(iii)}$ have a total combined height of approximately 40 mm (in the illustrated embodiment, each of $L_1$ and $L_{(i)}$ have a length of approximately 10 mm, each of $L_2$ and $L_{(ii)}$ have a length of approximately 14 mm, and each of $L_3$ and $L_{(iii)}$ have a length of approximately 16 mm). Thus, in some example embodiments, rods 314A and 314B have a total height on the order of approximately 40 mm to correspond with the total length of the first and second portions, and bent regions 360A, 360B are shaped and positioned so that straight portions of rods 314A and 314B, respectively can contact as much of regions $L_1$ and $L_3$ or $L_{(i)}$ and $L_{(iii)}$ as possible.

In one example embodiment, approximately six orthobiologic rods are introduced into a fracture cavity and distributed with a pair of forceps so that two orthobiologic rods are provided volarly, one is provided ulnarly, one is provide radially, and another two are provided dorsally. The number of orthobiologic rods that are used and their position can be adjusted depending on the nature and location of the bone fracture to be stabilized. In one example embodiment, the six orthobiologic rods are made from Norian™ SRS™.

In another example embodiment, three orthobiologic rods are provided as volar floor rods, two orthobiologic rods are provided as radial wall rods, one orthobiologic rod is provided as an ulnar wall rod, and two orthobiologic rods are provided as dorsal rods. In one example embodiment, the orthobiologic rods are made from Norian™ SRS™.

In another example embodiment illustrated in FIGS. 23 and 24, a volar rod 50H and a radial rod 50I are shown superimposed together with a plurality of spheres 30 superimposed on a lateral X-ray image of a fracture of a distal radius (FIG. 23) and superimposed on a posterioranterior X-ray image of the fracture of the distal radius (FIG. 24). In the illustrated embodiment, the shape of radial rod 50I has been selected to conform to the shape of the peripheral cortical bone on the radial aspect of the fracture cavity, and the shape of volar rod 50H has been selected to conform to the shape of the peripheral cortical bone on the volar aspect of the fracture cavity. The projection 126 on radial rod 50I has been engaged with aperture 112B on volar rod 50H so that the proximal ends of radial rod 50I and volar rod 50H are rotatable with respect to one another but are otherwise prevented from moving relative to one another. The remaining void space within the fracture cavity has been filled by the insertion of a plurality of spheres, which could be any of the embodiments of spheres described herein, e.g. spheres 20, 30, 30A, 30B or 40.

In some embodiments, the implants can be antibiotic-eluting. In some embodiments, either or both of the orthobiologic rods or orthobiologic spheres used are antibiotic eluting. Because the orthobiologic material used to form the implants is porous, the implants can be impregnated with a suitable antibiotic that can be released within the bone. Examples of antibiotics that can be used in accordance with some embodiments of the present invention include cephalosporins and aminoglycosides.

In some embodiments, the patient is an older individual. In some embodiments, the patient is over the age of fifty, over the age of fifty-five, over the age of sixty, over the age of sixty-five, over the age of seventy, over the age of seventy-five, or over the age of eighty. In some embodiments, the patient is a woman.

In some embodiments, methods as described above and/or orthobiologic rods and/or spheres are used in the stabilization of any type of bone fracture where the provision of a filler to fill the fracture void will be beneficial to prevent loss of reduction. In some embodiments, methods as described above and/or orthobiologic rods and/or spheres are used in the stabilization of any type of bone fracture that requires only a filler to fill the fracture void, and does not require other means of stabilization (for example, surgically inserted metal plates, screws, rods and pins). In some embodiments, methods as described above and/or orthobiologic rods and/ or spheres are used in the stabilization of metaphyseal fractures. In some embodiments, methods as described above and/or orthobiologic rods and/or spheres as described herein are used in the stabilization of fractures of the distal radius, proximal ulna (olecranon), calcaneus, proximal tibia, distal tibia, distal humerus, proximal humerus, distal femur, talus or cuboid bones. In some embodiments, methods as described above and/or orthobiologic rods and/or spheres as described herein are adapted to stabilize fractures in smaller bones.

EXAMPLES

Some example embodiments of the invention are further described with reference to the following examples, which are intended to be illustrative and not limiting in nature.

Example 1.0

Calculation of Reasonable Range of Diameters for Orthobiologic Spheres

A potential range of diameters that can be used for the orthobiologic spheres according to some embodiments was calculated, using typical dimensions of a distal radius as an example. The shape of the distal radius is trapezoidal, and representative typical external dimensions are approximately 2.8 cm wide distally and 2 cm proximally, 2.6 cm deep distally and 1.4 cm proximally, and approximately 2 cm long. Empty, this would represent volumetrically nearly 10 cm$^3$ externally. The internal volume of this trapezoid is estimated to approximate 5 cm$^3$. The volume of spherical implants of various diameters is presented in the table below. Assuming a random insertion of implants (e.g. as would reasonably be expected when using an inexact insertion technique that does not result in uniform packing of the spheres), the maximum number of spheres that one could introduce into an empty 5 cc area, adopting a Kepler Conjecture ratio of 0.65, for each of the sphere diameters is presented in the table below (Table 1).

TABLE 1

Number of spheres of varying diameters that could be accommodated in a typical distal radius fracture.

| Sphere diameter (cm) | 0.4 | 0.45 | 0.5 | 0.55 | 0.6 | 0.65 | 0.7 | 0.75 | 0.8 |
|---|---|---|---|---|---|---|---|---|---|
| Volume (cc) (4/3πr$^3$) | 0.034 | 0.046 | 0.067 | 0.084 | 0.113 | 0.142 | 0.180 | 0.222 | 0.268 |
| # of Spheres 5 cc/volume (cc) × 0.65 | 96 | 71 | 49 | 39 | 29 | 23 | 18 | 15 | 12 |

For a sphere, the volume is calculated as 4/3πr$^3$. Thus, a hollow sphere having a relatively larger radius will have a larger volume relative to the amount of material required to form the shell of the sphere than will a hollow sphere having a relatively smaller radius. Accordingly, to minimize the amount of orthobiologic material used to construct the spheres, the diameter (which is twice the radius, r), should be maximized, while the shell wall thickness should be minimized. However, it is also desirable to have a reasonable number of spheres for insertion into a fracture void. If the spheres are too small, it may be inconvenient to introduce large numbers of spheres into the fracture void. However, if the spheres are too large, it may be difficult to introduce the spheres into the fracture void through a small (e.g. approximately 1 cm) incision, and further the packing of larger spheres within the fracture void may be too loose to provide a reasonable degree of stabilization. Accordingly, it is anticipated that for the example case of a fracture of the distal radius, a sphere size in the range of a diameter of between about 5.5 mm and about 7.5 mm or any value therebetween, e.g. 6.0, 6.5 or 7.0 mm, would be suitable.

A range of potentially suitable diameters for any particular bone fracture could be determined by either engaging in studies such as computerized tomography (CT) scans to determine the anticipated void volume within a fracture of the bone, or engaging in studies on cadavers to assess a reasonable range of potentially suitable diameters.

Example 2.0

Evaluation of Load Carrying Capacity of Different Sphere Designs Using Finite Element and Statistical Methods The load carrying capacity of different designs of hollow spheres with different diameter, thickness, and hole-size (parameters shown in FIG. 25A) were evaluated using finite element analysis. Statistical analysis was performed to indicate the importance of each variable, and its effects on load carrying capacity of spheres. Solid spheres were found to support more load than other designs. Some cases of perforated spheres, also, exhibited noticeable load carrying capacity. Perforated spheres, with careful design, have the potential to be used instead of solid spheres. 6-hole and 4-hole spheres' results were comparable to each other. 6-hole spheres, however, supported more load. In all designs, diameter was the most important variable, and had the most effect on the load carrying capacity of spheres. Perforated sphere designs may be of interest in some embodiments over solid sphere designs, given that bone can grow inside the empty spaces within the perforated sphere, which may enhance fracture healing.

Four different sphere designs were analyzed: (1) 4-hole with four interconnected perforations (e.g. as shown in FIG. 1C), (2) 6-hole with six interconnected perforations (e.g. as shown in FIG. 1D), (3) solid spheres, and (4) spheres with six discontinuous perforations (e.g. as shown in FIG. 1E).

In the 4-hole design, the holes or perforations are equidistant from one another. In order to achieve that, the 3 bottom holes need to be in 109.5 degrees from one on top, and 120 degrees from each other (FIG. 1C). Another way to imagine this design is to imagine cutting a caltrop from inside a sphere. The axes of holes pass the center of sphere.

The 6-hole design (FIG. 1D) follows a more straightforward concept. All holes are equidistant form each other, and the angle between them is 90 degrees. Like the 4-hole design, all holes pass the center of sphere.

The perforated design (FIG. 1E) takes the idea of using 6-holes, and addresses the mechanical weakness that they may create. Since a greater number of holes may increase bone ingrowth, 6 holes may be preferable in comparison to 4 in some embodiments. Holes that completely pass through the sphere weaken its core. In order to limit that weakness, in the tested perforated design, the holes do not go all reach the center, but rather only perforate the spheres at a certain depth (2 mm in this example).

2.1. Finite Element Model

Figure 25A:
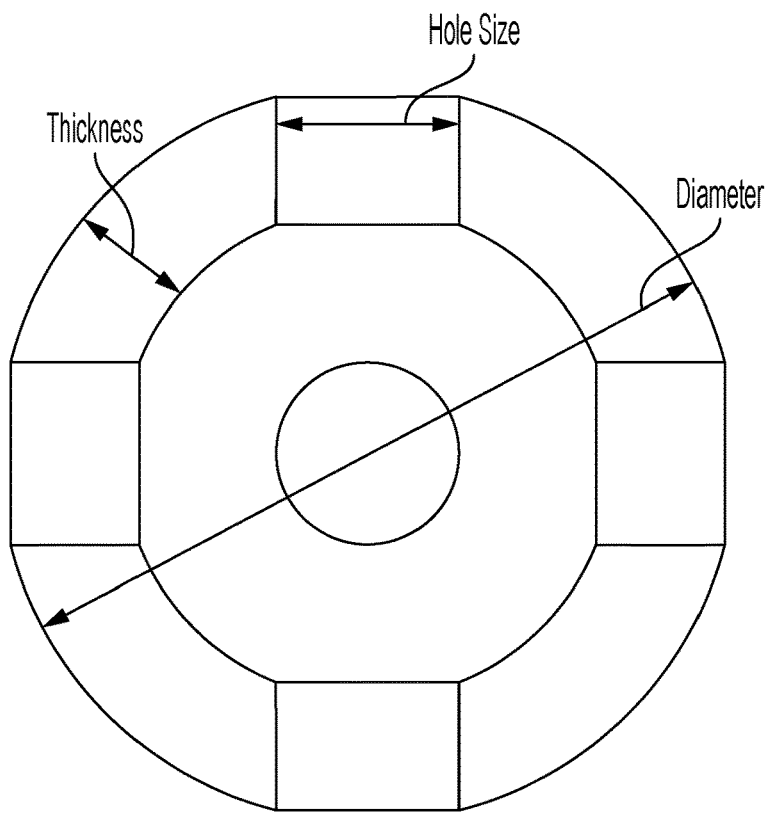
FIG. 25A shows the parameters of thickness, hole size and diameter that were tested in one exemplary embodiment.

In general, "thickness", "diameter of spheres", and "hole-diameter" were chosen as design parameters (as illustrated in FIG. 25A). Different values were assigned to these design parameters, which are shown in Table 2, and separate models were created. All combinations of design parameters were created, which results in 18 separate models for 6-hole design, 18 models for 4-hole design, 3 models for solid, and 3 models for perforated spheres. Hole-size in all perforated designs was kept constant at 2 mms.

TABLE 2

Different levels of design parameters.

| Diameter (mm) | Thickness (mm) | Hole-size (mm) |
|---|---|---|
| 5.5 | 1 | 1.5 |
| 6 | 1.5 | 2 |
| 6.5 | 2 | |

In order to calculate the maximum force between spheres in real life conditions, a simplified model of radius was created based on the work of Pietruszczak et al. [4]. Finite element (FE) method was used to assess the load carrying capacity of different designs. The methodology for assessing the load carrying capacity of spheres was to apply the calculated force at one end of the sphere, while fixing the other side of it (FIG. 25B, in which the applied force is shown on the image on the left, and the fixed support is shown on the image on the right).

In this example, the spheres are made out of Norian™ SRS Rotary Mix. Norian™ is brittle; therefore, Brittle Coulomb Mohr (BCM) was used for evaluating the ability of the spheres to bear load. The safety factor calculated from BCM failure criterion will be used to distinguish the effects of each variable (diameter, hole size, and wall thickness) on the load carrying capacity of the spheres. For this analysis, the higher the safety factor, the more load it can support.

Figure 25B:
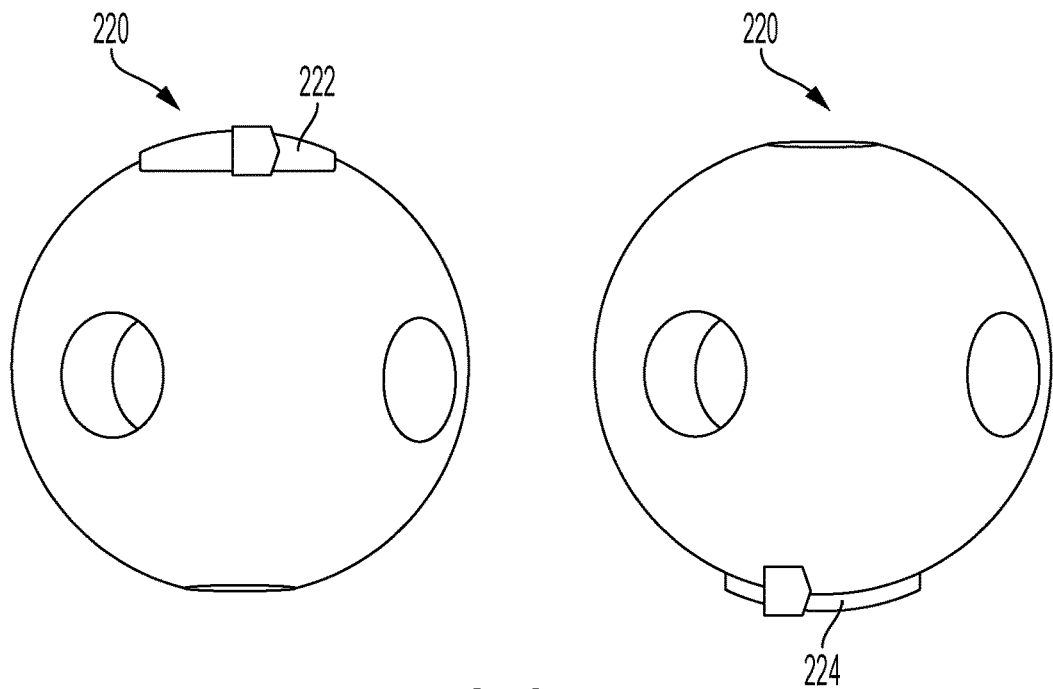
FIG. 25B is a figure showing schematically the boundary conditions of the finite element models used to evaluate sphere failure in one example. For this finite element model, a compressive load was applied simulating physiologic loading.

As shown on the left side of FIG. 25B, the top surface of an exemplary sphere 220 was modeled as a flat surface 222. This creates the worst case scenario. The ups and downs of the real radius distribute the load to the shell (e.g. the outer perimeter of the sphere will transfer a portion of a load applied on a distal side to the medial and lateral sides), whereas in the modeled flat surface, most of the load will be transferred to spheres.

In this example, a ramped quasi-static load of 300 N was applied to the radius. 180 N (mimicking the effect of scaphoid) was applied to one side on the surface, while 120 N (mimicking lunate) was applied to the other side (shown as fixed support 224 in FIG. 25B).

These values were chosen based on previous research in this field [4-7]. The output of this setup would be the maximum amount of force between spheres, and this value was used to assess the load carrying capacity of different designs and spheres.

2.2. Statistical Analysis

In order to evaluate whether a single factor stands out from the others with respect to load carrying capacity, and to evaluate how the interdependence of factors (e.g. between thickness and diameter) affects the load carrying capacity of the spheres, a full factorial design considering all three factors was performed. The significance of each factor, as well as their interactions were studied.

The data from each factorial design (4-hole and 6-hole) were analyzed using a general linear analysis of variance (ANOVA), which is equivalent to performing multiple linear regression [8]. ANOVA specifies the percentage contribution of each design parameter (factor) to total sum of squares of the responses. These were used to identify the significance of different factors.

2.3 Results of Finite Element Analysis

Figure 26A:
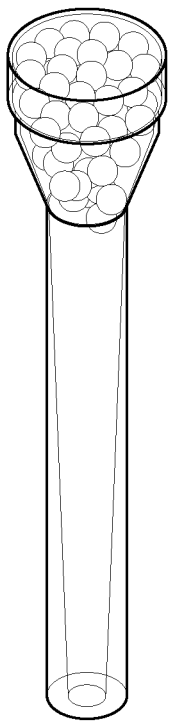
FIGS. 26A, 26B and 26C show the parameters used for another finite element analysis. In this model, which was a simplified representation of the radius filled with spheres, the radius was loaded with a proportion of load transmitted through the scaphoid and lunate contact regions of the distal radius.
Figure 26B:
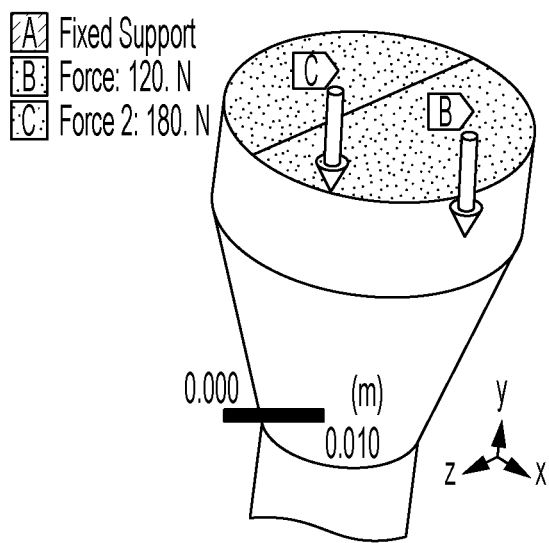
Figure 26C:
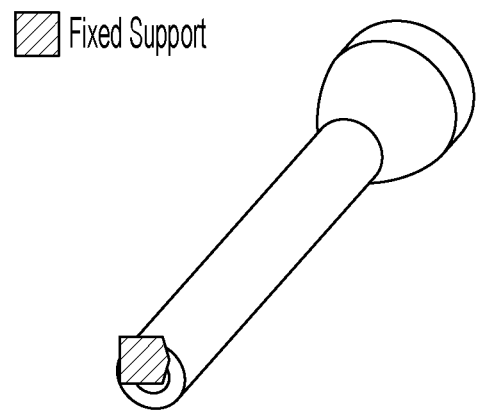

The finite element model, shown in FIGS. 26A, 26B and 26C was used to calculate forces between spheres. Panel A shows the finite element model used to calculate the forces between the spheres, and Panels B and C show the finite element model used to calculate the safety factor of spheres. The maximum amount of 27 N is observed when 300 N was applied to the surface of the radius. This value was used to calculate the load carrying capacity of different spheres, based on BCM failure criterion.

Figure 27:
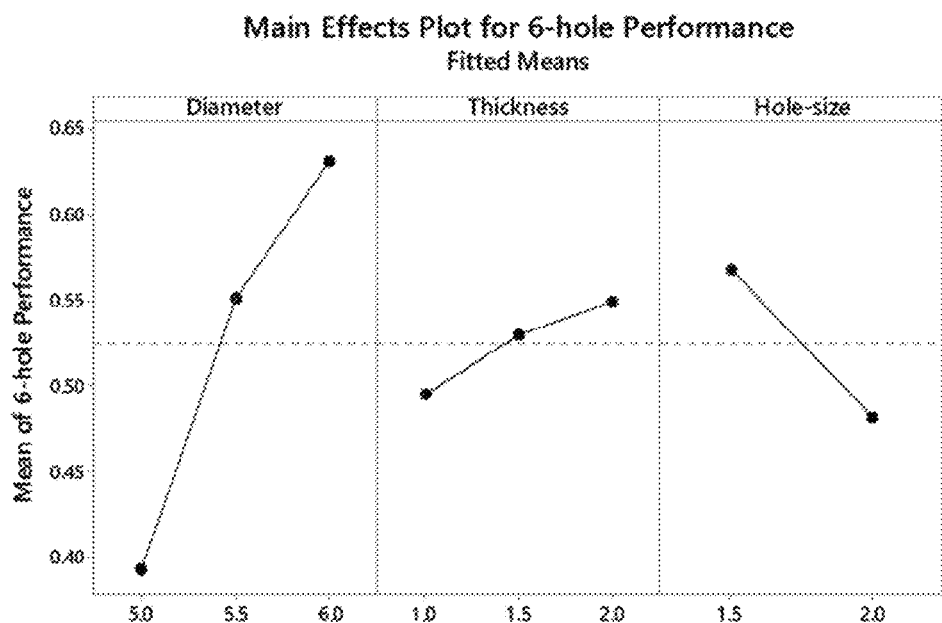
FIG. 27 is a figure showing the performance of an exemplary embodiment of a 6-hole perforated hollow sphere. For this analysis, performance was characterized in terms of the Brittle Coulomb Mohr (BCM) safety factor, where a higher number equates with an ability to support more load.

Table 3 shows the results of the 6-hole design, using ANSYS workbench finite element software package. The mean effect of each design parameter is shown in FIG. 27. The diameter has the most prominent effect on the results. Higher values of diameter and thickness increase the value of safety factor, while lower values of hole-size have the mentioned effect. In FIG. 27, X axis shows levels of each factor, and Y axis shows BCM safety factors. In this example, hollow perforated spheres were tested.

TABLE 3

Results of finite element analysis for the 6-hole design (all dimensions in mm).

| Diameter | Thickness | Hole-size | 6-hole Safety Factor |
|---|---|---|---|
| 5 | 1 | 1.5 | 0.47274 |
| 5 | 1 | 2 | 0.373 |
| 5 | 1.5 | 1.5 | 0.504074 |
| 5 | 1.5 | 2 | 0.234363 |
| 5 | 2 | 1.5 | 0.540814 |
| 5 | 2 | 2 | 0.234363 |
| 5.5 | 1 | 1.5 | 0.522259 |
| 5.5 | 1 | 2 | 0.491518 |
| 5.5 | 1.5 | 1.5 | 0.587851 |
| 5.5 | 1.5 | 2 | 0.549629 |
| 5.5 | 2 | 1.5 | 0.607888 |
| 5.5 | 2 | 2 | 0.549925 |
| 6 | 1 | 1.5 | 0.573962 |
| 6 | 1 | 2 | 0.541962 |
| 6 | 1.5 | 1.5 | 0.639296 |
| 6 | 1.5 | 2 | 0.668999 |
| 6 | 2 | 1.5 | 0.66574 |
| 6 | 2 | 2 | 0.699444 |

ANOVA was used to determine the significance of factors, and is shown in Table 4. Diameter has a P-value less than 0.001. The P-values of thickness and hole-size are 0.247 and 0.033, respectively. Based on the results, diameter is the most significant variable, followed by hole size. The linear regression model for 6-hole design has the R-squared of 71.8%, and Adjusted-R-squared of 65.8%.

TABLE 4

ANOVA for tested 6-hole sphere design.
Dependent Variable: 6-hole Performance

| Source | Type III Sum of Squares | df | Mean Square | F | Sig. |
|---|---|---|---|---|---|
| Corrected Model | .212[a] | 3 | .071 | 11.900 | .000 |
| Intercept | .024 | 1 | .024 | 3.962 | .066 |
| Diameter | .170 | 1 | .170 | 28.677 | .000 |
| Thickness | .009 | 1 | .009 | 1.461 | .247 |
| Hole-size | .033 | 1 | .033 | 5.563 | .033 |
| Error | .083 | 14 | .006 | | |
| Total | 5.265 | 18 | | | |
| Corrected Total | .295 | 17 | | | |

[a]R Squared = .718 (Adjusted R Squared = .658)

Figure 28:
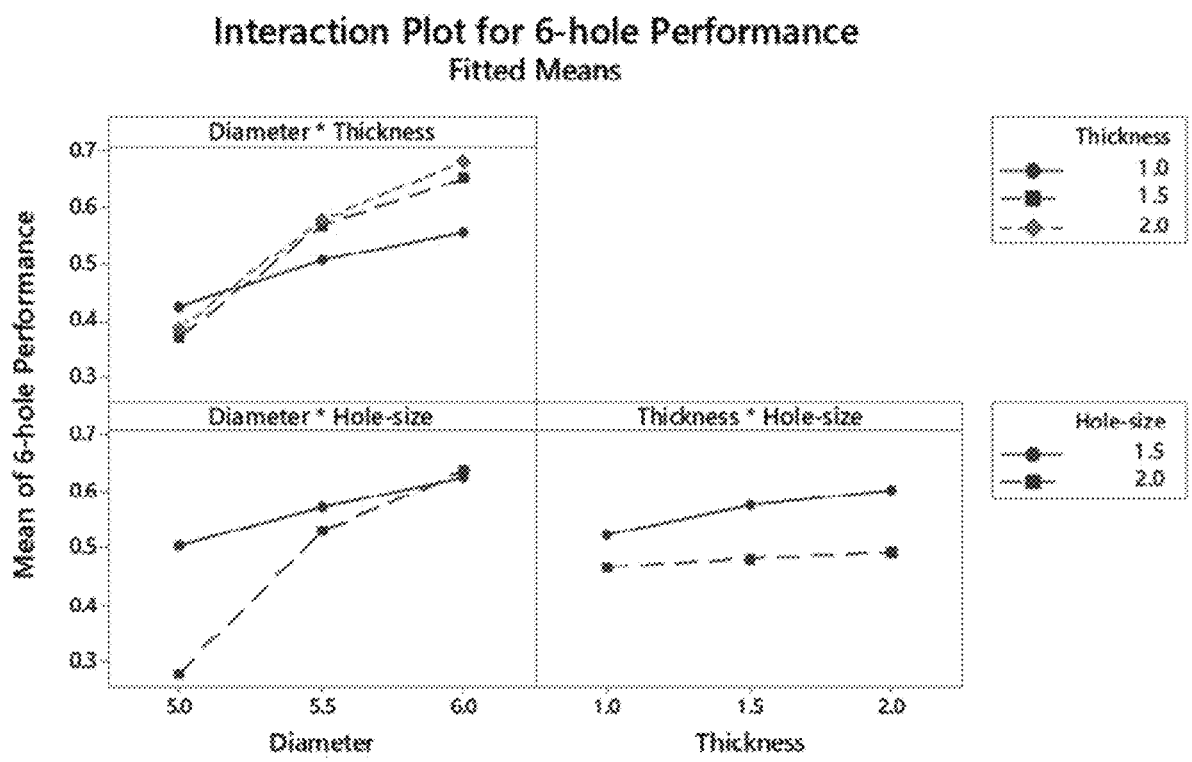
FIG. 28 is a figure showing the interaction of variables relating to sphere performance for an exemplary embodiment of a 6-hole perforated hollow sphere. Parallel lines mean no interaction.

FIG. 28 shows the interactions of variables for the tested 6-hole design. The variables are independent from each other if the lines are parallel to each other, and they follow a same pattern. Based on these plots, thickness and hole-size are the only variables that are independent from each other. Interdependence is observed between diameter-thickness, and diameter-hole size.

The same diagrams are shown for the tested 4-hole design. The results of the 4-hole design are presented in Table 5 and FIG. 29. In this design, thickness is the most prominent factor followed by diameter. The BCM safety factor increases with the increase in thickness and diameter.

TABLE 5

Results of finite element analysis for the tested 4-hole design (all dimensions in mm).

| Diameter | Thickness | Hole-size | 4-hole Safety Factor |
|---|---|---|---|
| 5 | 1 | 1.5 | 0.372814442 |
| 5 | 1 | 2 | 0.344021878 |
| 5 | 1.5 | 1.5 | 0.477073597 |
| 5 | 1.5 | 2 | 0.406777371 |
| 5 | 2 | 1.5 | 0.500406907 |
| 5 | 2 | 2 | 0.406777371 |
| 5.5 | 1 | 1.5 | 0.450777327 |
| 5.5 | 1 | 2 | 0.305233028 |
| 5.5 | 1.5 | 1.5 | 0.470888418 |
| 5.5 | 1.5 | 2 | 0.481073593 |
| 5.5 | 2 | 1.5 | 0.542480939 |
| 5.5 | 2 | 2 | 0.470221752 |
| 6 | 1 | 1.5 | 0.433666233 |
| 6 | 1 | 2 | 0.373258886 |
| 6 | 1.5 | 1.5 | 0.570777207 |
| 6 | 1.5 | 2 | 0.482629147 |
| 6 | 2 | 1.5 | 0.582406825 |
| 6 | 2 | 2 | 0.582629047 |

ANOVA of the tested 4-hole design is shown in Table 6. Thickness has a P-value less than 0.001, and is the most significant design parameter in 4-hole design. The P-value of diameter is 0.001, and the P-value of hole-size is 0.003.

TABLE 6

ANOVA for tested 4-hole design.
Tests of Between-Subjects Effects
Dependent Variable: 4-hole Performance

| Source | Type III Sum of Squares | df | Mean Square | F | Sig. |
|---|---|---|---|---|---|
| Corrected Model | .093[a] | 3 | .031 | 24.033 | .000 |
| Intercept | 1.026E−6 | 1 | 1.026E−6 | .001 | .978 |
| Diameter | .022 | 1 | .022 | 17.289 | .001 |
| Thickness | .054 | 1 | .054 | 41.852 | .000 |
| Holesize | .017 | 1 | .017 | 12.957 | .003 |
| Error | .018 | 14 | .001 | | |
| Total | 3.896 | 18 | | | |
| Corrected Total | .111 | 17 | | | |

[a]R Squared = .837 (Adjusted R Squared = .803)

Figure 30:
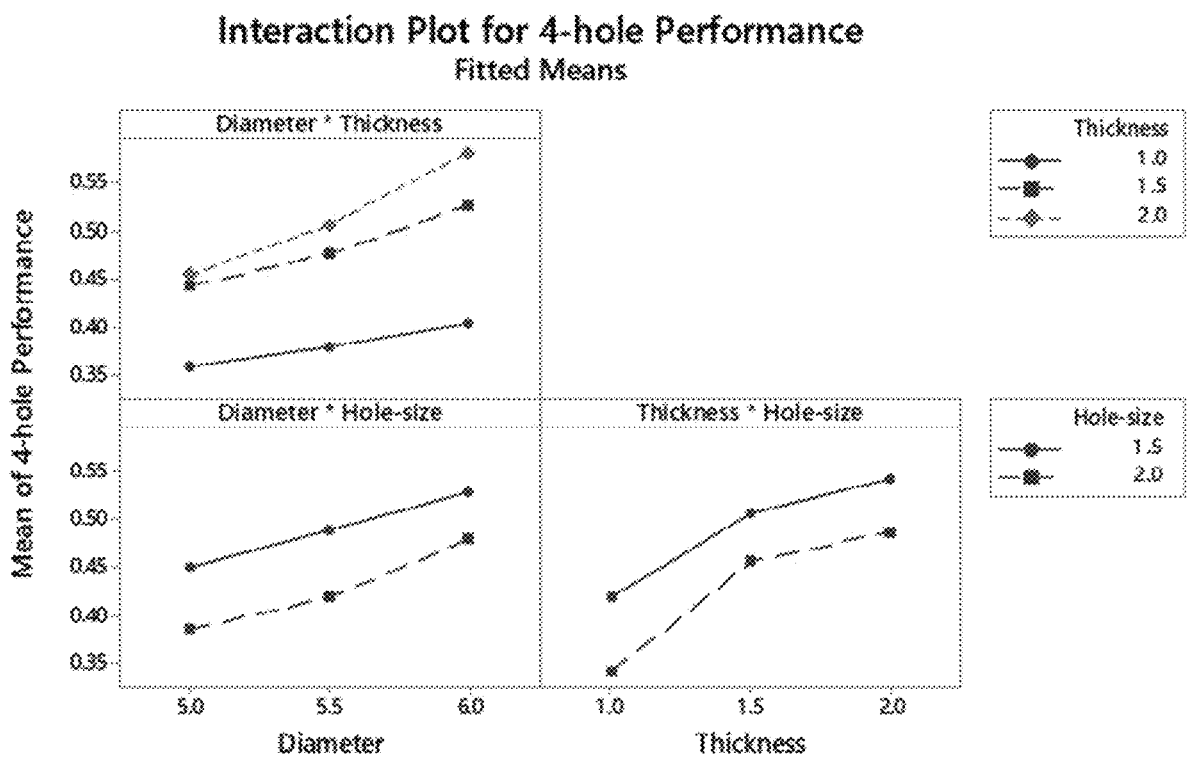
FIG. 30 is a figure showing the interaction of variables relating to sphere performance for an exemplary embodiment of a 4-hole perforated hollow sphere. Parallel lines mean no interaction.

FIG. 30 shows the interactions of design parameters for 4-hole design. Almost all of the lines are parallel to each other, and all of variables are independent from each other in this design. The most interdependency is observed between diameter and thickness.

Figure 31:
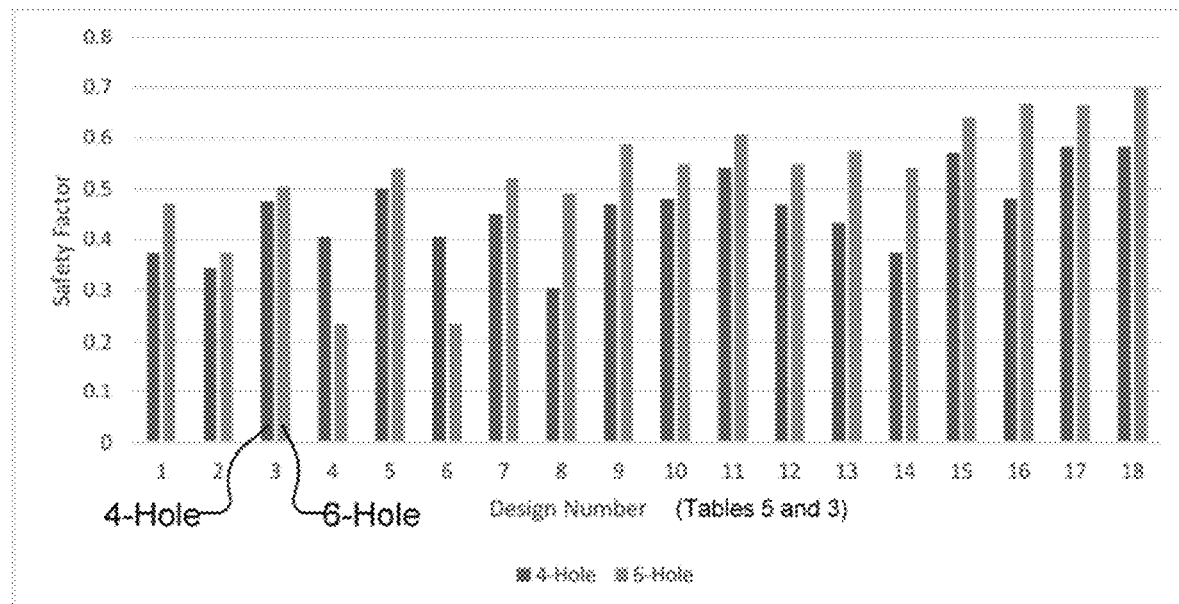
FIG. 31 is a chart showing a comparison of the safety factor of the tested 4-hole and 6-hole perforated hollow sphere designs with otherwise equivalent parameters.

In order to compare 4-hole design with 6-hole, results of Table 4 and Table 5 were drawn in FIG. 31. Generally, the 6-hole design displayed better safety factors. The Y axis of FIG. 31 is safety factor, and the X axis is the number of the design which corresponds to each horizontal row (i.e. rows 1-18) of Table 4 and Table 5. The largest difference between the 4-hole design, and the 6-hole design reaches relative value of 61% (design number 8: diameter=5.5 mm, thickness=1 mm, and hole-size=2 mm). The least difference is 5.6% for design number 3 with diameter of 5, thickness of 1.5, and hole-size of 1.5 mm.

Figure 32:
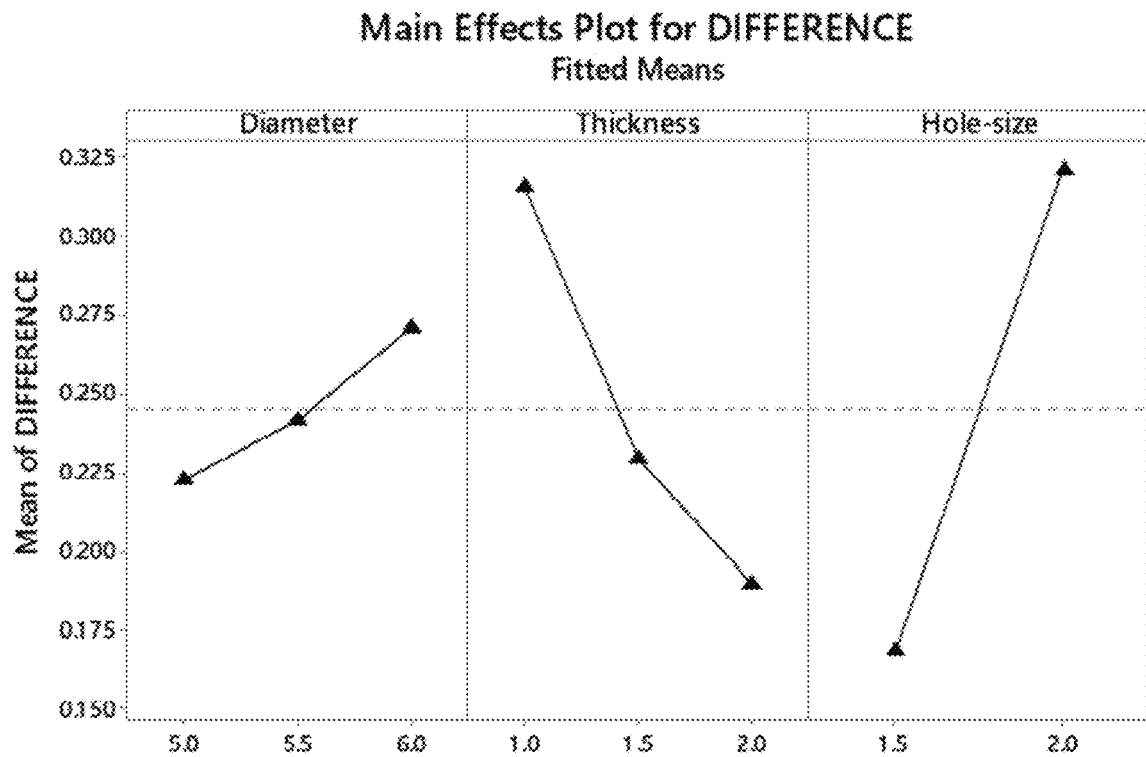
FIG. 32 is a plot of the effect of design parameters on the difference between tested 4-hole and 6-hole continuously perforated sphere designs.

FIG. 32 shows the effect of design parameters on the difference between safety factors of 6-hole and 4-hole designs. Higher values of hole-size and diameter, and lower values of thickness lead to higher difference between 4-hole and 6-hole safety factors. Hole-size is the most significant factor in this regard followed closely by thickness. Y axis is the relative difference in safety factor, between 4-hole and 6-hole designs.

The results of solid and perforated spheres are shown in Table 7. Solid spheres have the highest safety factors among other designs ranging from 1.8 (for diameter of 5 mm) to 2.9 (for 6 mm). Perforated spheres safety factors range from 0.17 to 0.97.

TABLE 7

Safety factors of solid spheres and discontinuously perforated spheres with hole size of 2 mm.

| Diameter (mm) | Solid spheres | Perforated spheres |
|---|---|---|
| 5 | 1.8 | 0.171 |
| 5.5 | 2.24 | 0.366 |
| 6 | 2.88 | 0.968 |

Figure 33:
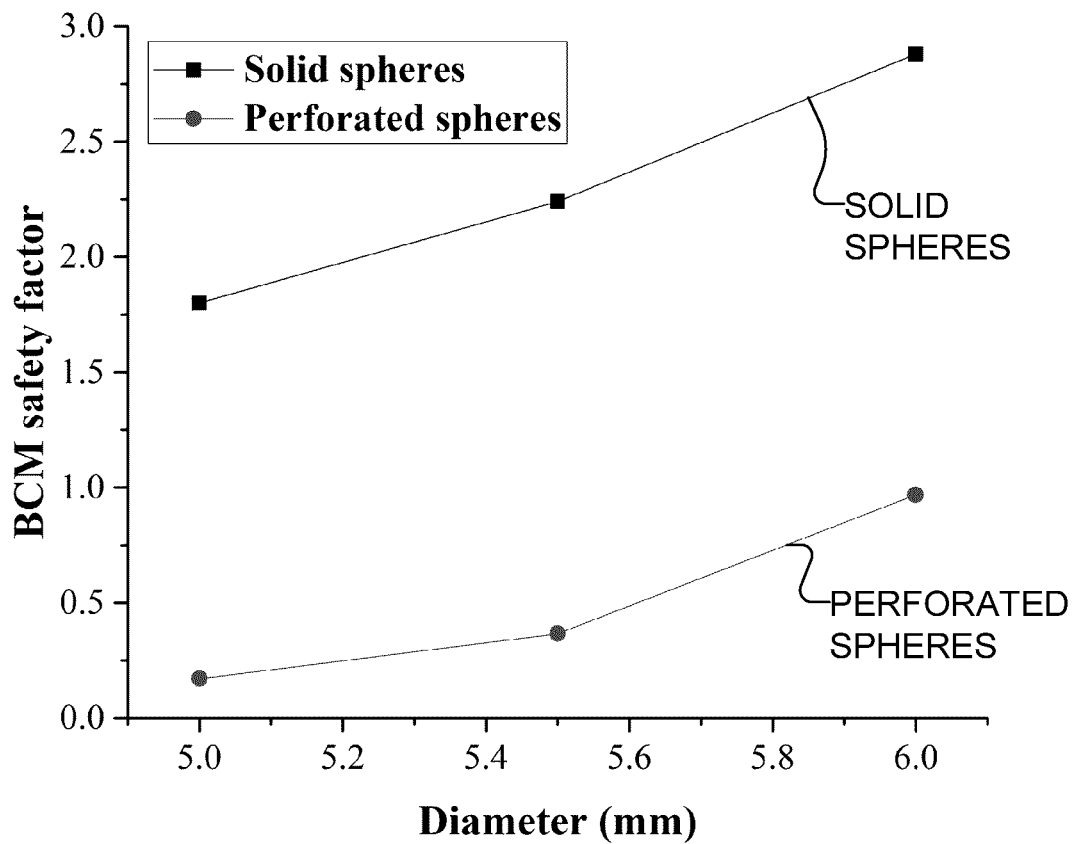
FIG. 33 is a comparison of the safety factors of solid spheres and discontinuously perforated spheres with a hole size of 2 mm.

A comparison between the perforated spheres with hole-size of 2 mm, and solid spheres is demonstrated in FIG. 33. Safety factors of perforated spheres decreased between 34% (for diameter of 6 mm) to 10% (diameter of 5 mm) relative to solid spheres.

2.4 Discussion of Finite Element Analysis Results for Spheres

The aim of this example was to identify the mechanical load carrying capacity of different sphere designs. Furthermore, the importance of different design parameters was investigated with the use of statistical factorial design. A combination of parameters was implemented, and finite element analysis was used to calculate the relative load carrying capacity of spheres.

Generally, the more material that is present in a sphere design, the more load that it can support before failure. Higher values of diameter and thickness add more bulk to a sphere, therefore, they result in higher safety factors. Lower hole-size subtracts less material from spheres, and same rule applies to them. This is true for both 4-hole and 6-hole designs, which can be observed in both FIGS. 27 and 29.

In terms of interaction between design parameters, no compelling interaction is observable for 4-hole design, but some interaction effect is observable in analysis of the 6-hole design. In general, it is desirable for factors not to have any interaction with each other. If two independent variables interact, the effect of one differs depending on the level of the other variable. As shown in FIG. 30, lines of thickness—diameter and thickness—hole size are almost parallel, which means there is no interaction between them. Diameter—thickness lines can also be regarded as parallel. In 6-hole design, except thickness—hole size, interaction effect is visible among other variables. This means, for example, thickness has a different effect on the load carrying capacity of the sphere, when the diameter is low, in comparison to when the diameter is high.

6-hole spheres generally supported more load than the corresponding 4-hole design. Without being bound by theory, this might be due to the loading regime that was used in this example. Load was applied to one end of the spheres while the other end was fixed. Since the axes of the holes in 4-hole design are located with an angle to the normal plane of the applied forces, higher stress values were induced to critical regions in the 4-hole spheres. Solid spheres have the highest safety factors among all designs. This is to be expected since solid spheres provide the most bulk, and there is no imperfection by design, in their nature. Perforated spheres are the second best design in terms of safety factors. They have the potential to perform better than 6-hole and 4-hole designs. However, even highest perforated sphere safety factor (d=6 mm) is almost half the lowest of solid sphere safety factor (d=5 mm) in this study.

In the tested 6-hole design, diameter is the most statistically significant factor among other variables, with a P-value less than 0.001. This indicates that changing the diameter has the most noticeable effect on the load carrying capacity of the spheres. Hole-size is the second most significant variable with the P-value of 0.033. In the tested 4-hole design, thickness has a P-value less than 0.001, and is the most significant variable. Diameter has also a P-value of 0.001, and is very close to that of thickness. In both designs, diameter plays a significant role in the ability of the spheres to support load.

The differences between safety factors of the tested 4-hole and 6-hole designs can be observed from FIG. 31. The largest and smallest amount of difference between the designs has been also determined. However, the effect of each design parameter (e.g. diameter) on the difference between 4-hole and 6-hole safety factors cannot be conclusively taken from this data. In order to do this, another factorial analysis is performed on the differences between 4-hole and 6-hole safety factors (difference between the 4-hole and 6-hole bars in FIG. 31), which is show in FIG. 32.

Figure 29:
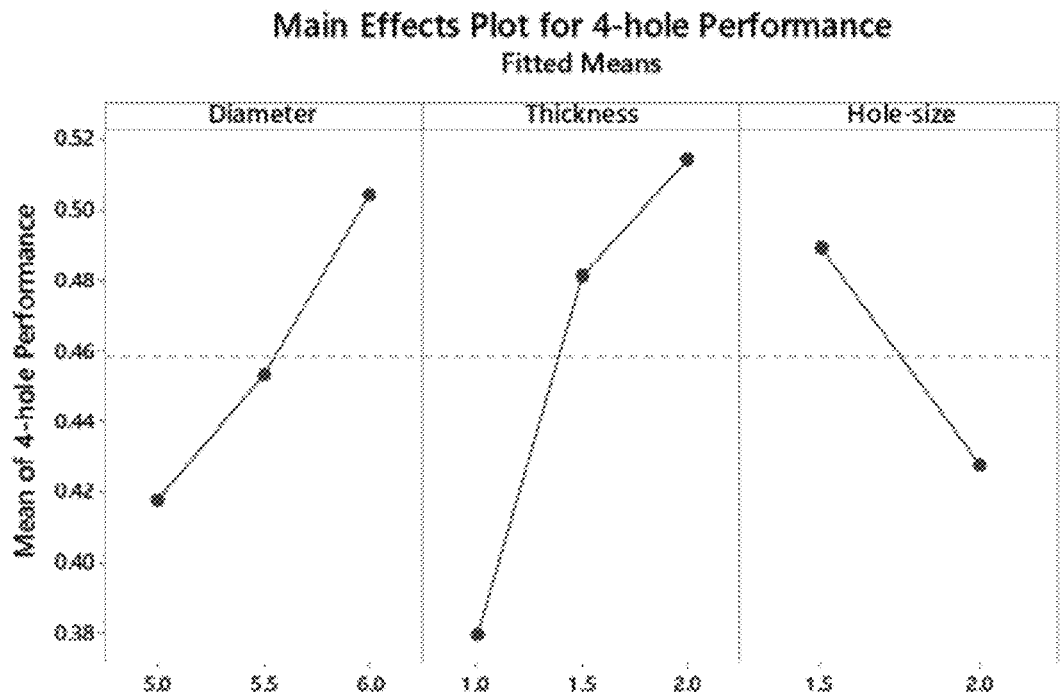
FIG. 29 is a figure showing the performance of an exemplary embodiment of a 4-hole perforated hollow sphere.

The results shown in FIG. 27 or 29 illustrate how changes in design parameters will affect the safety factors of spheres. FIG. 32, however, shows in which levels of factors (e.g. diameter of 5 or 6 mm), changing the design will affect the outcome the most. As an example, a sphere with higher diameter, lower thickness, and higher hole-size is more sensitive to a change in design, and any change in design will result in more changes in the load carrying capacity of the sphere than a sphere with lower diameter, higher thickness, and lower hole-size.

Load carrying capacity was evaluated using BCM safety factor. Safety factors below 1 are regarded as failure of material under load. Based on this result, and the BCM failure criterion, only solid spheres withstand the loading regime used in this study, and perforated spheres come close to it. In order to evaluate the forces between spheres in real life, a simplified model of a radius with flat top surface was used. This represents the worst case scenario, and in real life, the spheres may withstand the load. However, the ratio of safety factors between different designs is independent of the applied load. Therefore, based on these results, it is predicted that solid spheres, followed by perforated spheres, are the optimal designs with respect to the consideration of load carrying capacity.

Another limitation on finding the forces between spheres with the method used in this example is that it is dependent on the position of spheres inside the bone. In this example, one random layout of spheres was chosen. The results could change with different layouts. The simplified model used in this example also does not represent the real condition of bone. Furthermore, the effects of cyclic loading, and fatigue failure were not incorporated in the model.

This study evaluated the load carrying capacity of different designs of spheres using a finite element method. Solid spheres proved to support the most load. Perforated spheres have also demonstrated an ability to support load. 6-hole spheres, in general, supported more load than 4-hole spheres. For a more accurate estimate of safety factors, more lifelike models of bone can be used (i.e. subject specific models). Nevertheless, it is expected that the trends in relative safety factors of the spheres tested in this example would be relatively consistent when tested across different models.

Example 3.0

Proposed Protocol for Stabilization of a Fracture of the Distal Radius

An example protocol that could be used to stabilize a fracture of the distal radius is presented below. The protocol is based on establishing fracture stability at the initial clinical encounter, for example upon the patient's presentation after sustaining the fracture to an Emergency Department or the like.

Fracture reduction is achieved in the usual manner, and maintained by finger traction. The skin over the dorsal distal radius is prepared and draped in a small surgical field. Local anaesthesia is administered to the skin and soft tissues in the dorsal midline immediately proximal to the fracture. Fluoroscopy can be used to confirm a satisfactory reduction. The skin is marked with a marking pen just proximal to the fracture dorsocentrally, and an approximately 1-3 cm incision is made over the planned site of the radial drill hole. An entry drill hole is made, first with a small drill, and then enlarged with serially larger drills to achieve a pre-determined suitable diameter. For example, a 7.5 mm hole is drilled through the fracture site and a 7.5 mm curved trumpet, bone plants and implants can be introduced so that the surgery can be completed through this single access site.

In this example, approximately five orthobiologic rods according to an example embodiment are introduced and distributed in the fracture void with a pair of forceps: two volarly, one ulnarly, one radially and another dorsoradially. Multiple hollow perforated orthobiologic spheres according to another example embodiment are introduced with either forceps or a curved blunt plunger until the metaphysis is filled proximal and distal to the fracture site, and the fracture reduction is maintained without traction. Just before the last few spheres are inserted, a further orthobiologic rod is introduced immediately adjacent to the entry drill hole. Without being bound by theory, the use of an additional orthobiologic rod adjacent to the drill entry hole may provide a mechanical block to lessen post-procedural bleeding. After the last spheres have been placed, in some embodiments a final orthobiologic rod according to an example embodiment is positioned over the mouth of the drill hole.

The skin is repaired, a light compressive dressing is applied, and a lightweight, adjustable and removable wrist brace is applied. No cast is used. The patient is provided with an in-splint exercise program (i.e. exercises conducted while wearing the brace) for the fingers, elbow, shoulder and neck.

Example 4.0

Proposed Protocol for Stabilization of a Fracture of the Distal Radius

A second example protocol that could be used to stabilize a fracture of the distal radius is presented below. Fracture reduction is achieved and sustained by finger traction. Fluoroscopy is used to confirm a satisfactory reduction.

The skin is marked with a marking pen over the fracture dorsocentrally. Marking can be guided by fluoroscopy, if necessary. A second mark is made on the skin approximately 1 cm proximally of the first mark.

An arm or forearm tourniquet may be applied and inflated to 250 mm Hg immediately prior to skin incision. The skin is prepared and draped in a small surgical field. Local anaesthesia is administered, with or without a supplemental vasoconstrictor such as epinephrine, to the skin and soft tissues in the dorsal midline over the two skin marks. A hematoma block is performed at the fracture site. An approximately 1-3 cm incision is made over the more proximal of the two skin markings. The superficial fascia is incised, and the underlying extensor tendons are exposed and retracted. The floor of the extensor compartment is exposed, i.e. the dorsal distal radius.

An approximately 2.5 mm hole is drilled through the dorsal cortex of the radius, at approximately a 30 degree angle from the vertical, directed distally. The hole is sequentially expanded with larger drill bits up to a diameter of approximately 7.5 mm. A 6.5 mm curved tamp is introduced through the drill hole and used to reduce any intra-articular step deformity and to reinforce the subchondral region with metaphyseal bone to prepare the cavity to receive orthobiologic implants.

A plurality of porous orthobiologic rods as described herein are introduced into the fracture cavity. Two volar rods are introduced first, then one ulnar rod, and then one radial rod. A plurality of perforated hollow orthobiologic spheres as described herein are introduced into the fracture cavity using either forceps or a curved blunt plunger until the metaphysis is filled proximal and distal to the fracture site, and the fracture reduction is maintained without traction. Just before the last few perforated hollow orthobiologic spheres are inserted, two dorsal rods are introduced into the fracture cavity and distributed with a pair of forceps immediately adjacent the drill entry hole. After the last few perforated hollow orthobiologic spheres have been placed, two dorsal porous orthobiologic rods are positioned to lie over the mouth of the drill hole. In alternative embodiments, the long dorsal rods can be positioned to fill not only their function of stabilizing the distal radius, but also to perform the function of this proximal mechanical barrier. Without being bound by theory, it is believed that the solid segment provided by these rods provides a mechanical block to lessen post-procedural bleeding.

The skin is repaired and a light compressive dressing is applied. Either a bulky compression bandage or a lightweight, adjustable and removable wrist brace is applied. No cast is used. An in-splint exercise program is instituted for the fingers, elbow, shoulder and neck.

Example 5.0

Proposed Protocol for Stabilization of a Fracture of the Distal Radius

A third example protocol that could be used to stabilize a fracture of the distal radius is presented below. Fracture reduction is achieved and sustained by finger traction. Fluoroscopy is used to confirm a satisfactory reduction.

The skin is marked with a marking pen over the fracture dorsocentrally. Marking can be guided by fluoroscopy, if necessary. A second mark is made on the skin approximately 1 cm proximally of the first mark.

An arm or forearm tourniquet is applied and inflated to 250 mm Hg immediately prior to skin incision. The skin is prepared and draped in a small surgical field. Local anaesthesia is administered, with or without a supplemental vasoconstrictor such as epinephrine, to the skin and soft tissues in the dorsal midline over the two skin marks. A hematoma block is performed at the fracture site. An approximately 1-3 cm incision is made over the more proximal of the two skin markings. The superficial fascia is incised, and the underlying extensor tendons are exposed and retracted. The floor of the extensor compartment is exposed, i.e. the dorsal distal radius.

An approximately 2.5 mm hole is drilled through the dorsal cortex of the radius, at approximately a 30 degree angle from the vertical, directed distally. The hole is sequentially expanded with larger drill bits to a diameter of approximately 7.5 mm. A 6.5 mm curved tamp is introduced through the drill hole and used to reduce any intra-articular step deformity and to reinforce the subchondral region with metaphyseal bone to prepare the cavity to receive orthobiologic implants. Rod-specific seating chisels may be used to prepare the bed for the radial and volar rods.

A radial rod such as rod 50I is inserted into the resultant cavity, followed by a volar rod such as rod 50H. The two rods are linked together by engaging the projection 126 of the radial rod 50I with a suitable one of the apertures 112A/112B on the volar rod 50H. A plurality of orthobiologic spheres as described herein, for example perforated hollow orthobiologic spheres, are introduced into the fracture cavity using either forceps or a curved blunt plunger until the metaphysis is filled proximal and distal to the fracture site, and the fracture reduction is maintained without traction.

In an alternative embodiment, a radial rod such as rod 50I is first engaged with a volar rod such as rod 50H outside the fracture cavity, prior to insertion into the fracture cavity. For example, in one example embodiment, the projection 126 of the radial rod 50I is rotatably engaged with a suitable one of the apertures 112A/112B on the volar rod 50H. The linked rods are then rotated into an insertion configuration in which radial rod 50I and volar rod 50H extend generally parallel to one another (and consequently the combined assembly of radial rod 50I and volar rod 50H has a relatively narrow diameter that allows for insertion into the fracture cavity), and the linked rods are then inserted together into the resultant cavity. Once the linked rods 50H, 50I have been inserted into the fracture cavity, the two rods are rotated to an installed or deployed configuration in which radial rod 50I extends generally orthogonally to volar rod 50H (and consequently the combined assembly of radial rod 50I and volar rod 50H has a wider diameter than in the insertion configuration that provides for stability within the fracture cavity). A plurality of orthobiologic spheres as described herein, for example perforated hollow orthobiologic spheres, are introduced into the fracture cavity using either forceps or a curved blunt plunger until the metaphysis is filled proximal and distal to the fracture site, and the fracture reduction is maintained without traction.

The skin is repaired and a light compressive dressing is applied. Either a bulky compression bandage or a lightweight, adjustable and removable wrist brace is applied. No cast is used. An in-splint exercise program is instituted for the fingers, elbow, shoulder and neck.

Example 6.0

Proposed Post-Operative Recovery and Assessment Protocol

The patient can optionally be clinically and radiographically reviewed after week 1 by removing the dressing and x-raying the distal radius. The patient can also be reviewed clinically and radiographically at weeks 2, 3, 4 and 6, or at any other suitable interval as determined by the treating practitioner.

The patient can be provided with active, unresisted exercises for the wrist and forearm at week 3 or 4 depending on the clinical course. In some embodiments, such exercises are started once it is determined that fracture stability has been achieved. For example, fracture stability can be assessed by serial x-rays, and assessment of a patient's swelling and pain to determine if fracture stability has been achieved. In some embodiments, fracture stability may be achieved as early as one to three weeks post-fracture.

At week 9, the patient can be reviewed clinically, which may include for example a patient-rated wrist evaluation, evaluation of clinical features of the wrist and forearm range of motion and grip strength; and radiographically, which may include measures of radial inclination, ulnar variance and volar/dorsal tilt; evaluation of the fate of the implanted orthobiologic hollow perforated spheres and rods; and progress or attainment of fracture healing/union. The distal radius can be x-rayed. Soft tissue stretching and muscle strengthening exercises can be started for the hand, wrist and arm. Depending on the clinical and radiographic progress of the patient, these exercises might be started as early as four weeks post-fracture.

At week 12, the patient can be reviewed clinically, which may include for example a patient-rated wrist evaluation, evaluation of clinical features of the wrist and forearm range of motion and grip strength; and radiographically, which may include measures of radial inclination, ulnar variance and volar/dorsal tilt; evaluation of the fate of the implanted orthobiologic hollow perforated spheres and rods; and progress or attainment of fracture healing/union. The distal radius can be x-rayed to assess progress or attainment of fracture healing/union.

At weeks 26 and/or 52, the patient can be reviewed clinically, which may include for example a patient-rated wrist evaluation, evaluation of clinical features of the wrist and forearm range of motion and grip strength; and radiographically, which may include measures of radial inclination, ulnar variance and volar/dorsal tilt; evaluation of the fate of the implanted orthobiologic hollow perforated spheres and rods; and progress or attainment of fracture healing/union. The distal radius can be x-rayed to assess the fate of the implanted orthobiologic hollow perforated spheres and rods.

Example 7.0

Exemplary Protocol for distal Radial Fracture Fixation Surgical Technique

The patient's injured forearm and wrist are splinted, and an ice pack over the distal radius is secured The patient is placed supine on a stretcher/bed. A radiolucent arm board is secured to the stretcher/bed to support the arm. A tourniquet is applied to the upper arm, the timing of inflation left to the surgeon's discretion as to when, and if, to inflate. The fluoroscopy unit is positioned to facilitate PA and lateral imaging during the procedure. Pre-procedural PA and lateral images are obtained and stored.

Apply finger-traps to the thumb and middle finger, extended by ropes over the edge of the armboard and 10 lbs (~4 kg) weight is suspended from each rope. Remove the splint supporting the fracture. Prepare and drape the skin in the surgical field, extending circumferentially from the level of the metacarpophalangeal joints and thumb base to the mid-forearm. If the procedure is to be performed under local anaesthesia, the skin and soft tissues over the dorsal midline skin marking is infiltrated with the anaesthetic of choice, and a hematoma block at the distal radius fracture site is accomplished. Fluoroscopy is used to confirm a satisfactory reduction. Appropriate manipulation can be used to improve the reduction, as necessary.

Draw a 4-centimeter straight dorsal central midline skin mark, distally from the level of the transverse distal radial fracture (guided by fluoroscopy, if necessary), in a proximal direction. Inflate tourniquet to 250 mm of mercury immediately prior to the skin incision. Make a 2.5 cm. incision over the most proximal segment of the skin marking. Incise the superficial fascia, expose and retract the underlying extensor tendons of the 4th compartment. Expose the floor of the extensor compartment, the dorsal distal radius. Drill a 2.5 mm hole through the dorsal cortex of the radius, approximately 1.5 cm. proximal to the fracture, and inclined 30 degrees from the vertical, directed distally. Sequentially expand the hole with larger drill bits to a diameter of 7.5 mm.

Introduce the 6.5 mm curved tamp; use the tamp to: (a) redistribute the remaining soft cancellous bone of the distal radius to the periphery; (b) reduce depressed osteoarticular fracture fragments to correct post closed reduction intra-articular step deformity; and (c) reinforce the subchondral region with metaphyseal bone. Insert the radial rod seating chisel, using a mallet to prepare the channel along the radial aspect of the radial styloid. The same chisel, or the volar seating chisel, may also be used to correct any residual volar/dorsal displacement of the distal radial fragment and/or ulnar displacement of the radial shaft. Remove the chisel. Insert the volar rod seating chisel, using a mallet to prepare the channel along the volar aspect of the distal radius. Remove the chisel.

Introduce the radial rod (e.g. rod 50I), with the peg (e.g. projection 126) proximal and central. It should be stable. Confirm satisfactory position with fluoroscopy. Insert the volar rod (e.g. rod 50H), and seat the peg hole (e.g. one of apertures 112A, 112B) associated with the optimal position of the volar rod (confirmed by fluoroscopy) onto the peg of the radial rod. Introduce multiple spheres with either forceps or a curved blunt plunger until the metaphysis is filled proximal and distal to the fracture site.

Remove the weights, and assess quality of the fracture reduction with repeat PA and lateral fluoroscopic imaging. Once the fracture reduction and fixation are achieved, inject into the dorsal drill hole a calcium phosphate paste (or analog) to re-establish a stable physical barrier between the intramedullary canal and the extensor tendons. Deflate the tourniquet, apply pressure for approximately two minutes, and then cauterize subcutaneous vessels as necessary (unlikely). Repair the skin. Apply a light compressive dressing. Apply either a bulky compression bandage or a lightweight, adjustable and removable wrist brace (no cast). Institute an in-splint exercise program for the fingers, elbow, shoulder and neck.

Post-operatively: At 10 days post-op: Review the patient clinically and radiographically: remove the dressing and sutures (as needed), and perform PA and lateral x-rays of the distal radius. If the x-rays show: (a) no loss of reduction, then if (i) patient is comfortable and has full active ROM of the fingers, start active, unresisted exercises for the wrist and forearm; use a supportive splint for any lifting or carrying activities, and at night; and review at 3 weeks. If (ii) patient is still uncomfortable or has incomplete active range-ofmotion (ROM) of the fingers, re-apply a removable forearm-based wrist support, focus rehabilitation on restoration of full finger ROM, and repeat clinical and radiographic evaluation at 3 weeks post-op. If x-rays show (b) minimal loss of reduction: re-apply a removable forearm-based wrist support, focus rehabilitation on restoration of full finger ROM, and repeat clinical and radiographic evaluation at 3 weeks post-op. If x-rays show (c) an unacceptable loss of reduction, consider open reduction and internal fixation.

At 3 weeks post-op: Review the patient clinically and radiographically: assess finger and thumb motion, and perform PA and lateral x-rays of the distal radius. If the x-rays show: (a) no/minimal loss of reduction, then if (i) patient is comfortable and has full active ROM of the fingers, start, or continue, unresisted exercises for the wrist and forearm; repeat clinical and radiographic evaluation at 6 weeks post-op. If (ii) patient is still uncomfortable or has incomplete active ROM of the fingers the focus of ongoing treatment should be on formal physiotherapy for combined passive and active finger mobilization, coupled with appropriate pain management, and active assisted ROM of the wrist and forearm; use a supportive splint for any lifting or carrying activities, and at night; repeat clinical and radiographic evaluation at 6 weeks post-op. If x-rays show an unacceptable loss of reduction, consider open reduction and internal fixation.

At 6 weeks post-op: Review the patient clinically and radiographically: assess finger and thumb, wrist and forearm motion, and perform PA and lateral x-rays of the distal radius. If the x-rays show: (a) no/minimal loss of reduction, and advancing union, then if (i) if the patient is comfortable and has full active ROM of the fingers, and comfortable wrist and forearm motion, start a graduated strengthening program of resisted exercises for the wrist and forearm; use a supportive splint for any lifting or carrying activities. If (ii) patient is still uncomfortable or has incomplete active ROM of the fingers, the focus of ongoing treatment should be on formal physiotherapy for combined passive and active finger mobilization, coupled with appropriate pain management, active assisted ROM of the wrist and forearm, as well as a graduated strengthening program of resisted exercises for the wrist and forearm; use of a supportive splint for any lifting or carrying activities. If x-rays show (b) an unacceptable loss of reduction, consider open reduction and internal fixation.

At 12 weeks post-op: Review the patient clinically and radiographically: assess finger, thumb, wrist and forearm motion, and grip strength; perform PA and lateral x-rays of the distal radius to confirm that fracture healing has been achieved.

It is anticipated that early restoration and maintenance of the fracture reduction as can be achieved through use of protocols as described above may minimize residual deformity, increase patient satisfaction, diminish the risk of complications related to loss of reduction, eliminate the need for late correction of clinical deformity, accelerate the return of normal function, diminish the extent to which patients are compelled to remain away from work, and reduce the direct attributable cost of care of these very common fractures.

The foregoing protocols are also applicable to other metaphyseal fractures as well as to fractures of the distal radius, and it could be modified as necessary for use with other types of bone fractures.

In at least one clinical situation of which one of the inventors is aware, the injection of Norian™ SRS™ into a calcaneal fracture without casting produced a clinically desirable outcome. Accordingly, one skilled in the art could soundly predict that the use of a bone void filler can be used to promote improved healing of bone fractures.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within the scope of the claims given the broadest interpretation consistent with the specification as a whole.

Without limiting the foregoing, various embodiments encompass a plurality of aspects, some of which are further defined below.

A. An implant for stabilizing a bone fracture, the implant comprising a perforated hollow sphere of orthobiologic material.

B. An implant for stabilizing a bone fracture, the implant comprising a solid sphere of orthobiologic material with at least one perforation formed therein.

C. An implant for stabilizing a bone fracture as defined in aspect B, the implant comprising at least two interconnected perforations.

D. An implant for stabilizing a bone fracture, the implant comprising:
a hollow sphere having a shell made from orthobiologic material; and
a plurality of perforations through the shell.

E. An implant as defined in aspect D, wherein the perforations comprise apertures.

F. An implant as defined in any one of the preceding aspect, comprising four perforations or six perforations.

G. An implant as defined in any one of the preceding aspects, wherein the diameter of the sphere is in the range of about 5.5 to about 7.5 mm; wherein the diameter of the sphere is in the range of about 7.5 to about 10 mm; wherein the diameter of the sphere is in the range of about 2.0 to about 5.5 mm; and/or wherein the thickness of the shell of the sphere is in the range of about 0.5 to about 1 mm.

H. An implant as defined in any one of the preceding aspects, wherein the shape of the sphere is somewhat irregular, uneven or asymmetrical.

I. An implant for stabilizing a bone fracture, wherein the implant comprises a rod.

J. An implant as defined in aspect I, wherein the rod is generally cylindrical in shape;
wherein the rod has a generally elliptical cross-section across its axial height; and/or
wherein the rod has axially-opposite tapered ends.

K. An implant as defined in either one of aspects I or J, wherein the rod is curved or angled along its longitudinal axis.

L. An implant as defined in aspect K, wherein the degree of curvature of the rod along its longitudinal axis is selected to correspond to a degree of curvature or flare of a portion of bone against which the rod is intended to be inserted.

M. An implant as defined in any one of the preceding aspects, wherein the rod has a height in the range of about 25 to about 50 mm, a length in the range of about 2 mm to about 4 mm, and a width in the range of about 2 mm to 4 mm; and optionally wherein the rod has a length in the range of about 2 mm and a width in the range of about 4 mm.

N. An implant as defined in any one of the preceding aspects, wherein the rod comprises a short straight rod having a height in the range of about 25 to about 30 mm and is generally straight along its axial height.

O. An implant as defined in any one of aspects I to L, wherein the rod comprises a long curved rod having a height in the range of about 35 to about 50 mm and a curvature in the range of about 10 degrees to about 30 degrees along its axial height; wherein the curvature optionally comprises an elbow located approximately 35 mm from a distal end of the rod.

P. An implant as defined in any one of aspects I to L, wherein the rod comprises a long angled rod having a height in the range of about 35 to about 50 mm and an overall angle in the range of about 10 degrees to about 30 degrees along its axial height; wherein the overall angle is optionally provided by the sum of angles provided by two bends; and wherein the two bends are optionally located at approximately 10 mm and 25 mm, respectively from a first distal end of the rod.

Q. An implant for stabilizing a bone fracture comprising a rod having a shape configured to be complementary to a shape of the local peripheral cortical bone adjacent to which the rod is to be deployed within the bone fracture.

R. An implant as defined in aspect Q, further comprising structural features to minimize movement of the rod in its deployed position, wherein the structural features optionally comprise a projection for limiting rotational movement of the rod in its deployed position.

S. An implant for stabilizing a bone fracture comprising:
 a first rod having a shape configured to be complementary to a shape of the local peripheral cortical bone adjacent to which the first rod is to be deployed within the bone fracture;
 a second rod having a shape configured to be complementary to a shape of the local peripheral cortical bone adjacent to which the second rod is to be deployed within the bone fracture;
 the first rod and the second rod being provided with complementary engaging features so that the first rod and the second rod can be structurally linked together to limit relative movement of the first and second rods when deployed within the bone fracture.

T. An implant as defined in aspect S, wherein the complementary engaging features allow relative rotation of the first rod and the second rod, and wherein the first rod and the second rod are rotatable between an insertion configuration, in which the first and second rods extend generally parallel to one another, and a deployed configuration, in which the first and second rods extend generally orthogonal to one another.

U. An implant as defined in any one of aspects S or T, wherein the complementary engaging feature on the first rod comprises a projection, and wherein the complementary engaging feature on the second rod comprises an aperture dimensioned to receive the projection with a tight fit.

V. An implant as defined in aspect U, wherein:
 the first rod comprises a radial rod shaped and configured to be positioned against a radial aspect of the fracture cavity; and
 the second rod comprises a volar rod shaped and configured to be positioned against a volar aspect of the fracture cavity.

W. An implant as defined in aspect V, wherein:
 the radial rod comprises a proximal end having a gentle lateral outward curve from its proximal end in the distal direction, a middle portion having a gentle lateral outward curve in the distal direction, and a distal portion having a gentle lateral outward curve in the distal direction, wherein optionally an outer edge of the radial rod tapers inwardly from the distal end of the radial rod to the proximal end of the radial rod; and/or
 the volar rod comprises a proximal end that is angled slightly upwardly relative to a horizontal plane in a direction from its proximal end to its distal end, a middle portion that is angled more sharply upwardly relative to the horizontal plane in a direction from its proximal end to its distal end relative to the proximal end of the volar rod, and a distal portion that is curved slightly upwardly relative to the horizontal plane in a direction from its proximal end to its distal end.

X. An implant as defined in any one of the preceding aspects, wherein the rod comprises an orthobiologic material.

Y. An implant as defined in any one of the preceding aspects, where the rod comprises a biocompatible metal.

Z. An implant as defined in any one of the preceding aspects, wherein the orthobiologic comprises a ceramic, wherein the ceramic optionally comprises calcium phosphate, and wherein the calcium phosphate optionally comprises a Norian™ bone graft substitute, hydroxyapatite, biphasic calcium phosphate, or α- or β-tricalciumphosphate.

AA. An implant as defined in any one of the preceding aspects, wherein the orthobiologic is porous, and wherein the orthobiologic is optionally microporous.

BB. An implant as defined in any one of the preceding aspects, wherein the rod comprises a bone graft substitute material, wherein the bone graft substitute material optionally comprises coralline hydroxyapatite, a collagen-based matrix, a mineralized collagen matrix, calcium phosphate, calcium sulfate, calcium carbonate, demineralized bone matrix, fibers prepared using demineralized bone matrix, bioactive glass, a hydroxyapatite/calcium carbonate composite, and/or suitable polymers or copolymers.

CC. An implant as defined in any one of the preceding aspects, wherein at least the outer surface of the implant comprises a rough surface.

DD. An implant as defined in any one of the preceding aspects, wherein the rod is solid, or wherein the rod comprises one or more apertures therein.

EE. A method for stabilizing a bone fracture using an implant, the method comprising:
 inserting at least two rods into a fracture cavity within the bone to stabilize peripheral portions of the fracture cavity; and
 inserting a plurality of orthobiologic spheres into the fracture cavity.

FF. A method as defined in aspect EE, further comprising providing an insertion hole in the area of the bone fracture, wherein the insertion hole is optionally provided by drilling through the bone at the bone fracture, and wherein the insertion hole optionally has a diameter in the range of 7 to 10 mm.

GG. A method as defined in any one of the preceding aspects, wherein inserting the at least two rods comprises aligning at least some of the at least two rods around the periphery of the cavity.

HH. A method as defined in aspect GG, wherein inserting the at least two rods comprises aligning a plurality of short straight rods around the periphery of the cavity.

II. A method as defined in aspect GG, wherein inserting the at least two rods comprises inserting a plurality of long curved rods around the periphery of the cavity in axial alignment and placing each one of the plurality of long curved rods adjacent a region of bone having a degree of curvature that generally matches the degree of curvature of the rod.

JJ. A method as defined in aspect GG, wherein inserting the at least two rods comprises inserting a plurality of long angled rods around the periphery of the cavity in axial alignment and placing each one of the plurality of long angled rods adjacent a region of bone having an angle of curvature that generally matches the angle of the long angled rod.

KK. A method as defined in any one of the preceding aspects, wherein inserting the plurality of orthobiologic spheres comprises filling the fracture cavity with the plurality of orthobiologic spheres.

LL. A method as defined in any one of the preceding aspects, further comprising inserting one or more rods adjacent the insertion hole.

MM. A method as defined in any one of the preceding aspects, wherein the rods comprise rods as defined in any one of the preceding aspects; and/or wherein the spheres comprise spheres as defined in any one of the preceding aspects.

NN. A method as defined in any one of the preceding aspects, wherein the step of inserting at least two rods in the fracture cavity comprises structurally linking two of the at least two rods together to minimize movement of the linked rods relative to one another when deployed in the fracture cavity.

OO. A method as defined in aspect NN, where the linked rods are structurally linked after insertion into the fracture cavity.

PP. A method as defined in aspect NN, wherein the linked rods are structurally linked prior to insertion into the fracture cavity.

QQ. A method as defined in aspect PP, wherein the linked rods are rotatable when structurally linked together so that the linked rods can be rotated between an insertion configuration in which the linked rods extend generally parallel to one another and a deployed configuration in which the linked rods extend generally orthogonal to one another.

RR. A method as defined in any one of the preceding aspects, wherein the linked rods are structurally linked by inserting a projection on a first one of the linked rods into a corresponding aperture on a second one of the linked rods.

SS. A method as defined in any one of the preceding aspects, wherein the bone fracture comprises a bone fracture that requires only a filler to fill the fracture void.

TT. A method as defined in any one of the preceding aspects, wherein the bone fracture comprises a metaphyseal fracture.

UU. A method as defined in any one of the preceding aspects, wherein the bone fracture comprises a fracture of the distal radius, calcaneus, proximal tibia, or proximal humerus.

VV. A method as defined in any one of the preceding aspects, wherein the bone fracture comprises a fracture of a distal radius, and wherein inserting the plurality of orthobiologic rods comprises placing two orthobiologic rods volarly, one orthobiologic rod ulnarly, one orthobiologic rod radially, and one or two orthobiologic rods dorsally.

WW. A method as defined in any one of the preceding aspects, wherein the bone fracture comprises a fracture of a distal radius, and wherein inserting the plurality of orthobiologic rods comprises placing one orthobiologic rod on the volar floor, two orthobiologic rods on the radial wall, two orthobiologic rods dorsally, and one orthobiologic rod on the ulnar wall.

XX. A method of optimizing the shape and configuration of an implant for use in stabilizing a fracture wherein the implant is to be positioned adjacent a particular surface of a fracture cavity defined by the fracture, the method comprising the steps of:
preparing a model of the implant using an additive manufacturing method;
inserting the model of the implant to a deployed configuration against the particular surface of the fracture in a model of the fracture cavity;
evaluating fit and stability of the model of the implant against the particular surface of the fracture in the model of the fracture cavity;
adjusting a shape of the model of the implant to enhance stability of the model of the implant in the deployed configuration to produce a revised model of the implant;
preparing the revised model of the implant using the additive manufacturing method;
inserting the revised model of the implant in the deployed configuration within the model of the fracture cavity; and
evaluating fit and stability of the revised model of the implant against the particular surface of the fracture in the model of the fracture cavity.

YY. A method as defined in aspect XX, wherein the additive manufacturing method comprises 3D printing.

ZZ. A method as defined in either one of aspects XX or YY, wherein the model of the fracture cavity comprises a cadaver specimen or a plastic model.

AAA. A method as defined in any one of the preceding aspects, wherein the fracture comprises a distal radial fracture, wherein the implant comprises a rod, and wherein the particular surface of the fracture cavity comprises a distal surface or a volar surface of the distal radial fracture.

BBB. A method as defined in any one of the preceding aspects, comprising simultaneously optimizing the shape and configuration of two implants, wherein the two implants are provided with structural features for linking the two implants.

CCC. An implant for stabilizing a fracture cavity having the shape and configuration shown in FIGS. 7A-7F.

DDD. An implant for stabilizing a fracture cavity having the shape and configuration shown in FIGS. 8A-8E.

REFERENCES

The following references are cited herein. Each reference cited in this specification is incorporated herein by reference in its entirety.

[1] Court-Brown C M, Caesar B. Epidemiology of adult fractures: a review. Injury 2006; 37:691-7.
[2] Lichtman D M, Bindra R R, Boyer M I, Putnam M D, Ring D, Slutsky D J, et al. Treatment of distal radius fractures. J Am Acad Orthop Surg 2010; 18:180-9.
[3] Shauver M J, Yin H, Banerjee M, Chung K C. Current and future national costs to medicare for the treatment of distal radius fracture in the elderly. J Hand Surg Am 2011; 36:1282-7.
[4] Pietruszczak S, Gdela K, Webber C E, Inglis D. On the assessment of brittle-elastic cortical bone fracture in the distal radius. Eng Fract Mech 2007; 74:1917-27. doi: http://dx.doi.org/10.1016/j.engfracmech.2006.06.005.
[5] Schuind F, Cooney W P, Linscheid R L, An K N, Chao E Y S. Force and pressure transmission through the normal wrist. A theoretical two-dimensional study in the posteroanterior plane. J Biomech 1995; 28:587-601. doi: 10.1016/0021-9290(94)00093-J.

[6] Majima M, Horii E, Matsuki H, Hirata H, Genda E. Load Transmission Through the Wrist in the Extended Position. J Hand Surg Am 2008; 33:182-8. doi:10.1016/j.jhsa.2007.10.018.
[7] Edwards W B, Troy K L. Finite element prediction of surface strain and fracture strength at the distal radius. Med Eng Phys 2012; 34:290-8. doi:http://dx.doi.org/10.1016/j.medengphy.2011.07.016.
[8] Dar F H, Meakin J R, Aspden R M. Statistical methods in finite element analysis. J Biomech 2002; 35:1155-61. doi:10.1016/S0021-9290(02)00085-4.

What is claimed is:

1. An implant for insertion into a fracture cavity to stabilize a bone fracture, the implant comprising a first rod having a curved or angled configuration, wherein a degree of curvature of the first rod along a longitudinal axis of the first rod or an angular configuration of the first rod along the longitudinal axis of the first rod is selected to correspond to a degree of curvature or flare of a portion of bone within the fracture cavity against which the first rod is intended to be inserted;
the first rod further comprising a component for engaging with a second rod to be deployed within the fracture cavity to minimize movement of the first rod in its deployed position.

2. An implant as defined in claim 1, wherein the first rod has a shape configured to be complementary to a shape of local peripheral cortical bone adjacent to which the first rod is to be deployed within the bone fracture.

3. An implant as defined in claim 2, the first rod further comprising structural features to minimize movement of the first rod in its deployed position.

4. An implant as defined in claim 3, wherein the structural features comprise a projection for limiting rotational movement of the first rod in its deployed position, the projection being configured to engage against the adjacent local peripheral cortical bone when the first rod is in its deployed configuration.

5. An implant as defined in claim 2, wherein the first rod is a volar rod shaped and configured to be positioned against a volar aspect of the fracture cavity, wherein the first rod comprises a proximal end that is angled slightly upwardly at a first angle relative to a horizontal plane in a direction from the proximal end of the first rod to a distal end of the first rod, a middle portion that is angled upwardly at a second angle relative to the horizontal plane in a direction from the proximal end of the first rod to the distal end of the first rod, the second angle being greater than the first angle, and a distal portion that is curved slightly upwardly relative to the horizontal plane in a direction from the proximal end of the first rod to the distal end of the first rod.

6. An implant as defined in claim 2, wherein the first rod is a radial rod shaped and configured to be positioned against a radial aspect of the fracture cavity, wherein the first rod comprises a proximal end having a gentle lateral outward curve from its proximal end in a distal direction, a middle portion having a gentle lateral outward curve in the distal direction, and a distal portion having a gentle lateral outward curve in the distal direction.

7. The implant as defined in claim 6, wherein an outer edge of the first rod tapers inwardly from a distal end of the first rod to the proximal end of the first rod.

8. An implant as defined in claim 1, wherein the implant comprises an orthobiologic material or a biocompatible metal.

9. An implant as defined in claim 8, wherein the orthobiologic is porous.

10. An implant as defined in claim 1, wherein the implant comprises a bone graft substitute material.

11. An implant as defined in claim 1, wherein at least an outer surface of the first rod comprises a rough surface; and/or wherein the first rod is solid, or wherein the first rod comprises one or more apertures therein.

12. A kit comprising one or more implants as defined in claim 1 and one or more perforated hollow spheres, solid spheres with at least one perforation formed therein, or solid spheres.

13. A method for stabilizing a bone fracture using an implant, the method comprising:
inserting an implant as defined in claim 1 into a fracture cavity within a bone to stabilize peripheral portions of the fracture cavity; and
inserting a plurality of spherical implants into the fracture cavity.

14. A method as defined in claim 13, wherein the step of inserting an implant into the fracture cavity comprises structurally linking the first rod with the second rod to minimize movement of the two linked rods relative to one another when deployed in the fracture cavity.

15. An implant for stabilizing a bone fracture having a fracture cavity, the implant comprising:
a first rod having a shape configured to be complementary to a shape of the local peripheral cortical bone adjacent to which the first rod is to be deployed within the fracture cavity; and
a second rod having a shape configured to be complementary to a shape of the local peripheral cortical bone adjacent to which the second rod is to be deployed within the fracture cavity;
the first rod and the second rod being provided with complementary engaging features so that the first rod and the second rod can be structurally linked together in an assembly to limit relative movement of the first and second rods when deployed within the fracture cavity;
the complementary engaging features allowing relative rotation of the first rod and the second rod, and wherein the first rod and the second rod are rotatable between an insertion configuration, in which an angle defined between the first and second rods has a minimum value, and a deployed configuration in which the angle defined between the first and second rods is greater than the minimum value.

16. An implant as defined in claim 15, wherein the complementary engaging features allow relative rotation of the first rod and the second rod, and wherein the first rod and the second rod are rotatable between an insertion configuration in which the assembly of the first and second rods has a first diameter, and a deployed configuration, in which the assembly of the first and second rods has a second diameter that is greater than the first diameter.

17. An implant as defined in claim 15, wherein the complementary engaging feature on the first rod comprises a projection, and wherein the complementary engaging feature on the second rod comprises an aperture dimensioned to receive the projection with a tight fit.

18. An implant as defined in claim 15, wherein:
the first rod comprises a radial rod shaped and configured to be positioned against a radial aspect of the fracture cavity; and
the second rod comprises a volar rod shaped and configured to be positioned against a volar aspect of the fracture cavity.

19. An implant as defined in claim 18, wherein:
the first rod comprises a proximal end having a gentle lateral outward curve from its proximal end in the distal direction, a middle portion having a gentle lateral outward curve in a distal direction, and a distal portion having a gentle lateral outward curve in the distal direction.

20. The implant as defined in claim 18, wherein the second rod comprises a proximal end that is angled slightly upwardly at a first angle relative to a horizontal plane in a direction from the proximal end of the second rod to a distal end of the second rod, a middle portion that is angled more sharply upwardly at a second angle relative to the second rod horizontal plane in a direction from the proximal end of the second rod to the distal end of the second rod, the second angle being greater than the first angle, and a distal portion that is curved slightly upwardly relative to the second rod horizontal plane in a direction from the proximal end of the second rod to the distal end of the second rod.

* * * * *